US008475506B1

(12) United States Patent
Bendett et al.

(10) Patent No.: US 8,475,506 B1
(45) Date of Patent: Jul. 2, 2013

(54) VCSEL ARRAY STIMULATOR APPARATUS AND METHOD FOR LIGHT STIMULATION OF BODILY TISSUES

(75) Inventors: Mark P. Bendett, Kirkland, WA (US); Jonathon D. Wells, Seattle, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 1317 days.

(21) Appl. No.: 12/191,301

(22) Filed: Aug. 13, 2008

Related U.S. Application Data

(60) Provisional application No. 60/964,634, filed on Aug. 13, 2007, provisional application No. 61/081,732, filed on Jul. 17, 2008.

(51) Int. Cl.
*A61N 5/06* (2006.01)

(52) U.S. Cl.
USPC .............................................. 607/89; 607/88

(58) Field of Classification Search
USPC .......................................................... 607/89
See application file for complete search history.

(56) References Cited

U.S. PATENT DOCUMENTS

| | | |
|---|---|---|
| 4,064,872 A | 12/1977 | Caplan |
| 4,215,694 A | 8/1980 | Isakov et al. |
| 4,296,995 A | 10/1981 | Bickel |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |

(Continued)

FOREIGN PATENT DOCUMENTS

WO    WO 0025112    5/2000

OTHER PUBLICATIONS

Infrared (IR) wavelength definition_Wikipedia (2012).*
Augustine, George J., "Combining patch-clamp and optical methods in brain slices", "Journal of Neuroscience Methods", 1994, pp. 163-169, vol. 54.
Banghart, Matthew, et al., "Light-activated ion channels for remote control of neuronal firing", "Nature Neuroscience", Nov. 21, 2004, pp. 1381-1386, vol. 7, No. 12.
Boyden, Edward S., et al., "Millisecond-timescale, genetically targeted optical control of neural activity", "Nature Neuroscience", Sep. 2005, pp. 1263-1268, vol. 8, No. 9.
Bureau, Ingrid, et al., "Precise Development of Functional and Anatomical Columns in the Neocortex", "Neuron", Jun. 10, 2004, pp. 789-801, vol. 42.

(Continued)

*Primary Examiner* — Yong Chu
(74) *Attorney, Agent, or Firm* — David J. King; Jonathan M. Rixen; Lemaire Patent Law Firm, P.L.L.C.

(57) ABSTRACT

An apparatus and method using an array of VCSELs operable to emit light at one or more wavelengths, pulse-repetition rates, pulse durations, pulse powers, pulse energies, and/or light-distribution spatial and/or temporal patterns, that are effective to stimulate or photostimulate human or other animal tissue, and in particular, nerve tissue. In some embodiments, the invention provides an implantable device that includes an array having a plurality of VCSELs in a spatial pattern suitable to stimulate or photostimulate a plurality of different areas of tissue (e.g., a plurality of different nerves). In some embodiments, the device is instead partially implantable. In some embodiments, the device is instead external to the body of the animal.

20 Claims, 19 Drawing Sheets

U.S. PATENT DOCUMENTS

| | | | |
|---|---|---|---|
| 6,074,411 A | 6/2000 | Lai et al. | |
| 6,104,957 A | 8/2000 | Alo et al. | |
| 6,110,195 A | 8/2000 | Xie et al. | |
| 6,152,882 A | 11/2000 | Prutchi | |
| 6,171,239 B1 | 1/2001 | Humphrey | |
| 6,184,542 B1 | 2/2001 | Alphonse | |
| 6,224,969 B1 | 5/2001 | Steenbergen et al. | |
| 6,246,892 B1 | 6/2001 | Chance | |
| 6,257,759 B1 | 7/2001 | Witonsky et al. | |
| 6,258,082 B1 | 7/2001 | Lin | |
| 6,263,221 B1 | 7/2001 | Chance et al. | |
| 6,267,779 B1 | 7/2001 | Gerdes | |
| 6,272,367 B1 | 8/2001 | Chance | |
| 6,284,078 B1 | 9/2001 | Witonsky et al. | |
| 6,294,109 B1 | 9/2001 | Ratna et al. | |
| 6,301,279 B1 | 10/2001 | Garbuzov et al. | |
| 6,310,083 B1 | 10/2001 | Kao et al. | |
| 6,312,451 B1 | 11/2001 | Streeter | |
| 6,314,324 B1 | 11/2001 | Lattner et al. | |
| 6,324,429 B1 | 11/2001 | Shire et al. | |
| 6,330,388 B1 | 12/2001 | Bendett et al. | |
| 6,339,606 B1 | 1/2002 | Alphonse | |
| 6,353,226 B1 | 3/2002 | Khalil et al. | |
| 6,358,272 B1 | 3/2002 | Wilden | |
| 6,363,188 B1 | 3/2002 | Alphonse | |
| 6,417,524 B1 | 7/2002 | Alphonse | |
| 6,444,313 B1 | 9/2002 | Ono et al. | |
| 6,456,866 B1 | 9/2002 | Tyler et al. | |
| 6,459,715 B1 | 10/2002 | Khalfin et al. | |
| 6,475,800 B1 | 11/2002 | Hazen et al. | |
| 6,488,704 B1 | 12/2002 | Connelly et al. | |
| 6,493,476 B2 | 12/2002 | Bendett | |
| 6,505,075 B1 | 1/2003 | Weiner | |
| 6,542,530 B1 | 4/2003 | Shieh et al. | |
| 6,542,772 B1 | 4/2003 | Chance | |
| 6,546,291 B2 | 4/2003 | Merfeld et al. | |
| 6,556,611 B1 | 4/2003 | Khalfin et al. | |
| 6,564,076 B1 | 5/2003 | Chance | |
| 6,592,611 B1 | 7/2003 | Zawada | |
| 6,630,673 B2 | 10/2003 | Khalil et al. | |
| 6,636,678 B1 | 10/2003 | Bendett et al. | |
| 6,639,930 B2 | 10/2003 | Griffel et al. | |
| 6,669,379 B2 | 12/2003 | Janosik et al. | |
| 6,669,765 B2 | 12/2003 | Senga et al. | |
| 6,688,783 B2 | 2/2004 | Janosik et al. | |
| 6,690,873 B2 | 2/2004 | Bendett et al. | |
| 6,735,474 B1 | 5/2004 | Loeb et al. | |
| 6,735,475 B1 | 5/2004 | Whitehurst et al. | |
| 6,744,548 B2 | 6/2004 | Abeles | |
| 6,746,473 B2 | 6/2004 | Shanks et al. | |
| 6,748,275 B2 | 6/2004 | Lattner et al. | |
| 6,823,109 B2 | 11/2004 | Sasaki et al. | |
| RE38,670 E | 12/2004 | Asah et al. | |
| 6,836,685 B1 | 12/2004 | Fitz | |
| 6,871,084 B1 | 3/2005 | Kingsley et al. | |
| 6,902,528 B1 | 6/2005 | Garibaldi et al. | |
| 6,909,826 B2 | 6/2005 | Cai et al. | |
| 6,921,413 B2 | 7/2005 | Mahadevan-Jansen et al. | |
| 6,953,341 B2 | 10/2005 | Black | |
| 6,956,650 B2 | 10/2005 | Boas et al. | |
| 6,989,023 B2 | 1/2006 | Black | |
| 7,003,353 B1 | 2/2006 | Parkhouse | |
| 7,004,645 B2 | 2/2006 | Lemoff et al. | |
| 7,006,749 B2 | 2/2006 | Illich et al. | |
| 7,010,341 B2 | 3/2006 | Chance | |
| 7,010,356 B2 | 3/2006 | Jog et al. | |
| 7,031,363 B2 * | 4/2006 | Biard et al. | 372/45.01 |
| 7,040,805 B1 | 5/2006 | Ou et al. | |
| 7,068,878 B2 | 6/2006 | Crossman-Bosworth et al. | |
| 7,069,083 B2 | 6/2006 | Finch | |
| 7,079,900 B2 | 7/2006 | Greenburg et al. | |
| 7,085,300 B2 | 8/2006 | Werner et al. | |
| 7,095,770 B2 | 8/2006 | Johnson | |
| 7,116,886 B2 | 10/2006 | Colgan et al. | |
| 7,131,968 B2 | 11/2006 | Bendett et al. | |
| 7,139,603 B2 | 11/2006 | Chance | |
| 7,156,866 B1 | 1/2007 | Riggs et al. | |
| 7,160,289 B2 | 1/2007 | Cohen | |
| 7,177,081 B2 | 2/2007 | Tomita et al. | |
| 7,190,993 B2 | 3/2007 | Sharma et al. | |
| 7,194,063 B2 | 3/2007 | Dilmanian et al. | |
| 7,225,028 B2 | 5/2007 | Della Santina et al. | |
| 7,231,256 B2 | 6/2007 | Wahlstrand et al. | |
| 7,244,253 B2 | 7/2007 | Neev | |
| 7,302,296 B1 | 11/2007 | Hoffer | |
| 7,311,722 B2 | 12/2007 | Larsen | |
| 7,324,852 B2 | 1/2008 | Barolat et al. | |
| 7,329,251 B2 | 2/2008 | Yamada et al. | |
| 7,337,004 B2 | 2/2008 | Classen et al. | |
| 7,351,241 B2 | 4/2008 | Bendett et al. | |
| 7,391,561 B2 | 6/2008 | Di Teodoro et al. | |
| 7,402,167 B2 | 7/2008 | Nemenov | |
| 7,488,341 B2 | 2/2009 | Merfeld | |
| 7,647,112 B2 | 1/2010 | Tracey et al. | |
| 7,736,382 B2 | 6/2010 | Webb et al. | |
| 7,747,318 B2 | 6/2010 | John et al. | |
| 7,756,588 B2 | 7/2010 | Jog et al. | |
| 7,776,631 B2 | 8/2010 | Miles | |
| 7,787,170 B2 | 8/2010 | Patel et al. | |
| 7,797,029 B2 | 9/2010 | Gibson et al. | |
| 7,801,601 B2 | 9/2010 | Maschino et al. | |
| 7,803,454 B2 | 9/2010 | Toepel | |
| 7,833,257 B2 | 11/2010 | Walsh, Jr. et al. | |
| 7,873,085 B2 | 1/2011 | Babushkin et al. | |
| 7,883,535 B2 | 2/2011 | Cantin et al. | |
| 7,883,536 B1 | 2/2011 | Bendett et al. | |
| 7,899,512 B2 | 3/2011 | Labadie et al. | |
| 7,914,842 B1 | 3/2011 | Greenberg et al. | |
| 8,012,189 B1 * | 9/2011 | Webb et al. | 607/89 |
| 2001/0021287 A1 | 9/2001 | Jewell et al. | |
| 2002/0002391 A1 | 1/2002 | Gerdes | |
| 2003/0165171 A1 | 9/2003 | Jewell | |
| 2003/0236458 A1 | 12/2003 | Hochman | |
| 2004/0225339 A1 | 11/2004 | Yaroslavsky et al. | |
| 2005/0099824 A1 | 5/2005 | Dowling et al. | |
| 2005/0143789 A1 | 6/2005 | Whitehurst et al. | |
| 2005/0216072 A1 | 9/2005 | Mahadevan-Jansen et al. | |
| 2006/0161218 A1 | 7/2006 | Danilov | |
| 2006/0167564 A1 | 7/2006 | Flaherty et al. | |
| 2006/0276861 A1 | 12/2006 | Lin | |
| 2007/0036493 A1 | 2/2007 | Brenner et al. | |
| 2007/0053996 A1 | 3/2007 | Boyden et al. | |
| 2007/0054319 A1 | 3/2007 | Boyden et al. | |
| 2007/0060984 A1 | 3/2007 | Webb et al. | |
| 2007/0191906 A1 | 8/2007 | Iyer et al. | |
| 2007/0260297 A1 | 11/2007 | Chariff | |
| 2007/0261127 A1 | 11/2007 | Boyden et al. | |
| 2008/0009748 A1 | 1/2008 | Gratton et al. | |
| 2008/0077198 A1 | 3/2008 | Webb et al. | |
| 2008/0077200 A1 | 3/2008 | Bendett et al. | |
| 2008/0086206 A1 | 4/2008 | Nasiatka et al. | |
| 2008/0161697 A1 | 7/2008 | Chance | |
| 2008/0183247 A1 | 7/2008 | Harding | |
| 2009/0030327 A1 | 1/2009 | Chance | |
| 2009/0054954 A1 | 2/2009 | Foley et al. | |
| 2009/0076115 A1 | 3/2009 | Wharton et al. | |
| 2009/0163982 A1 | 6/2009 | deCharms | |
| 2009/0177255 A1 | 7/2009 | Merfeld | |
| 2009/0210039 A1 | 8/2009 | Boyden et al. | |
| 2010/0049180 A1 | 2/2010 | Wells et al. | |
| 2010/0145418 A1 | 6/2010 | Zhang et al. | |
| 2010/0184818 A1 | 7/2010 | Wharton et al. | |

OTHER PUBLICATIONS

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U, et al., "Precisely Localized LTD in the Neocortex Revealed by Infrared-Guided Laser Stimulation.", "Science", Oct. 1, 1999, pp. 110-113, vol. 286.

Eder, Matthias, et al., "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, p. 1108-1114, vol. 54, No. 6(1).

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

Allegre, et al., "Stimulation in the rat of a nerve fiber bundle by a short UV pulse from an excimer laser", "NeuroScience Letters ", 1994, pp. 261-264, vol. 180.

Arridge, et al., "The theoretical basis for the determination of optical pathlengths in tissue: temporal and frequency analysis", "Phys. Med. Biol. ", 1992, pp. 1531-1560, vol. 37.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Chance, et al., "Comparison of time-resolved and—unresolved measurements of deoxyhemoglobin in brain", "Proc. Nati. Acad. Sci. USA", Jul. 1988, pp. 4971-4975, vol. 85.

Fork, Richard L., "Laser Stimulation of Nerve Cells in Aplysia", "Science, New Series", Mar. 5, 1971, pp. 907-908, vol. 171, No. 3974.

Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, pp. e299, No. 3, Publisher: www.plosone.org.

Huang, Ying-Ying, et al., "Biphasic Dose Response in Low Level Light Therapy", "Dose-Response", 2009, pp. 358-383, vol. 7.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, pp. 021008 , vol. 12, No. 2.

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , pp. 064036, vol. 10, No. 6.

Princeton Lightwave (Company), "High Power Multimode Laser Arrays", "www.princetonlightwave.com/content/pli_high_power_multimode_laser_arrays.pdf", Dec. 24, 2005 downloaded.

Princeton Lightwave (Company), "High Power Water Cooled Laser Stack", "http://www.princetonlightwave.com/content/pli_high_power_multimode_laser_stacks.pdf", Oct. 24, 2005 downloaded.

Princeton Lightwave (Company), "High Power Single Element Laser", "www.princetonlightwave.com/content/HP%20Single%20Element%20Laser%20version%202.pdf", 2005 (downloaded).

Rolfe, "In Vivo Near-Infrared Spectroscopy", "Annu. Rev. Biomed. Eng.", 2000, pp. 715-754 , vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng ", 2003, pp. 227-35, vol. 11, No. 3.

Teudt, et al., "Optical Stimulation of the Facial Nerve: A New Monitoring Technique?", "The Laryngoscope", 2007, pp. 1641-1647, vol. 117, No. 9.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

* cited by examiner

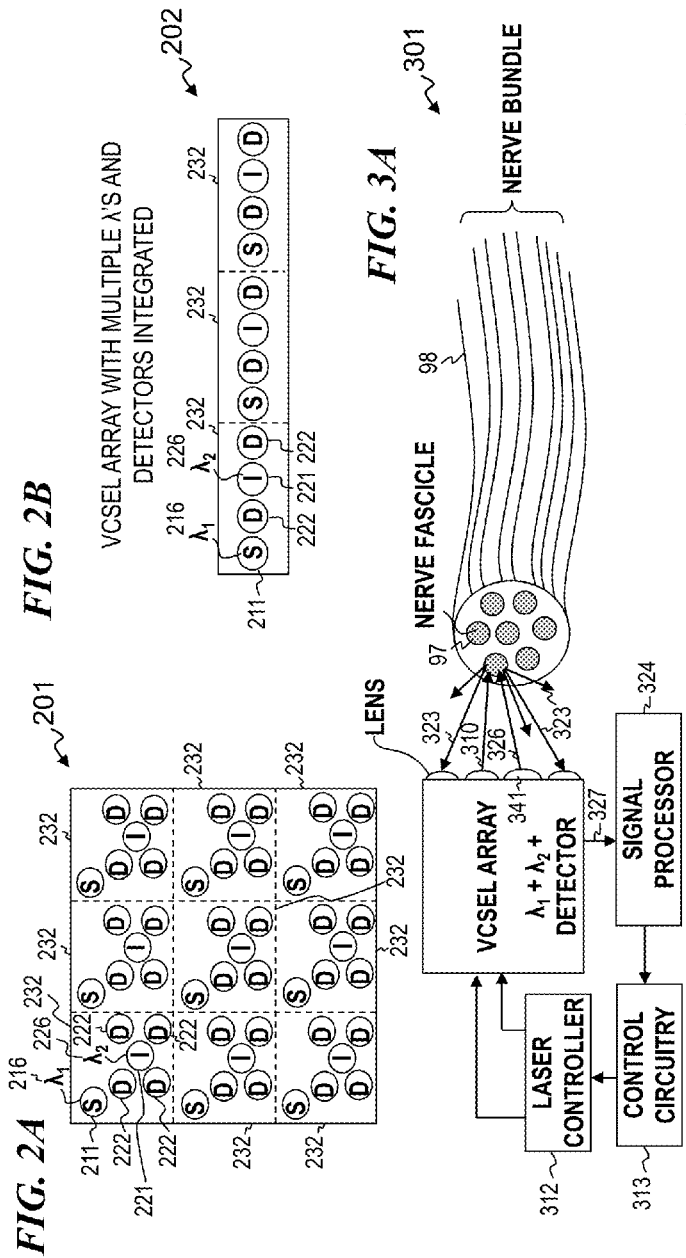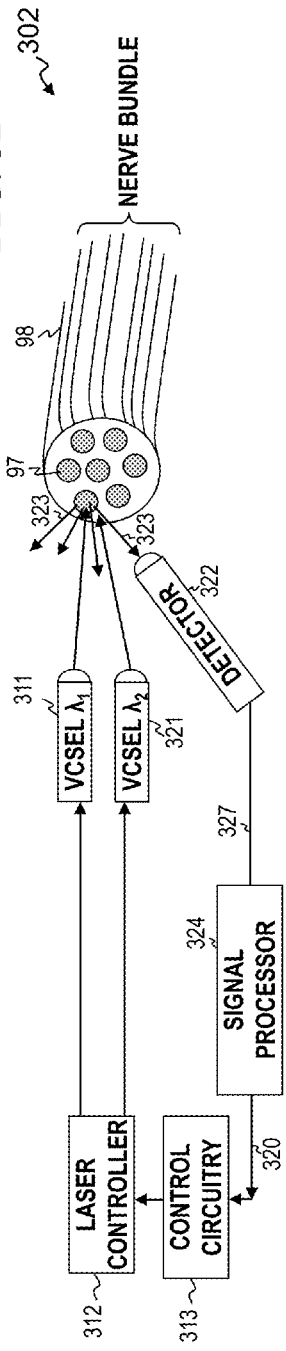

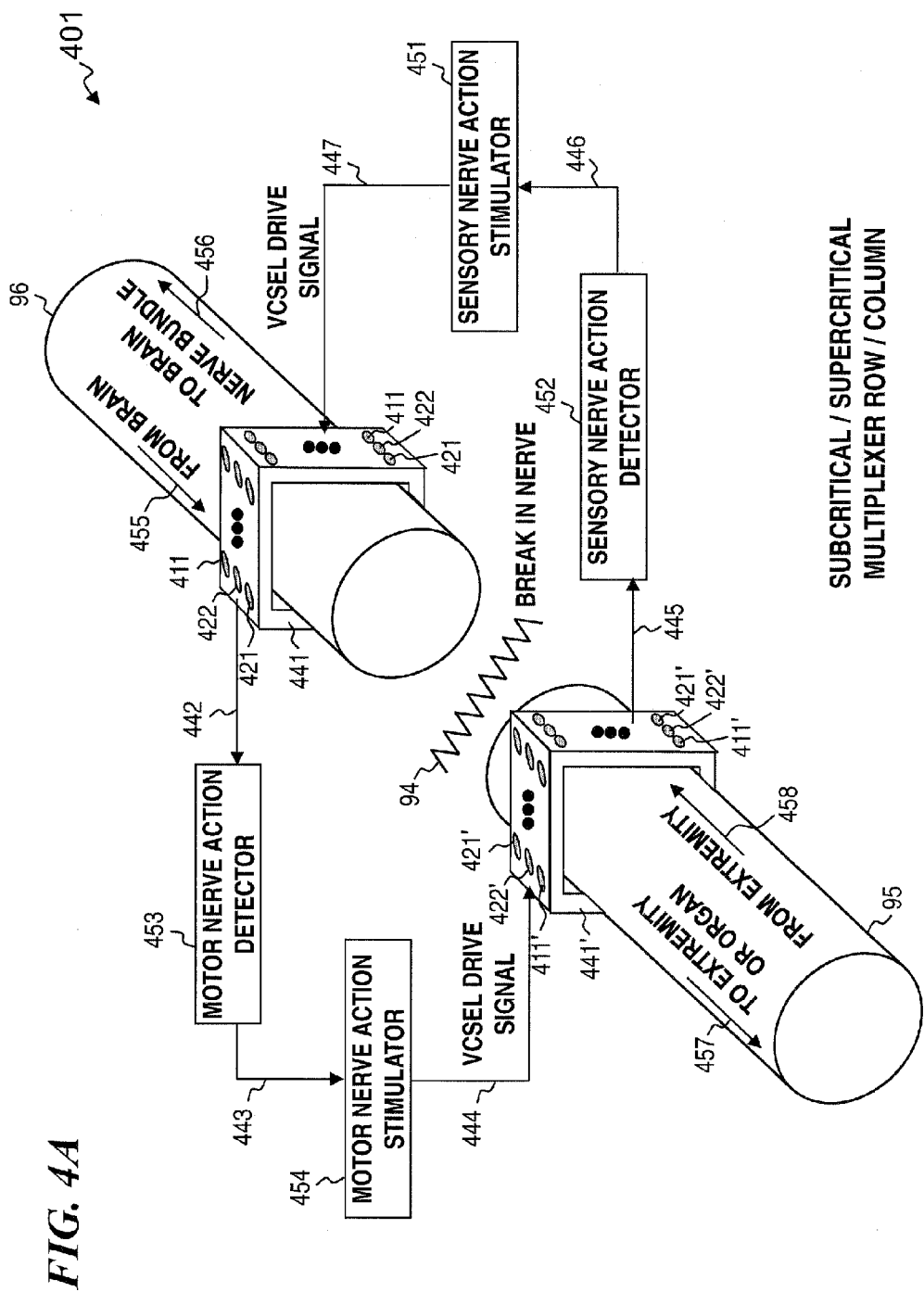

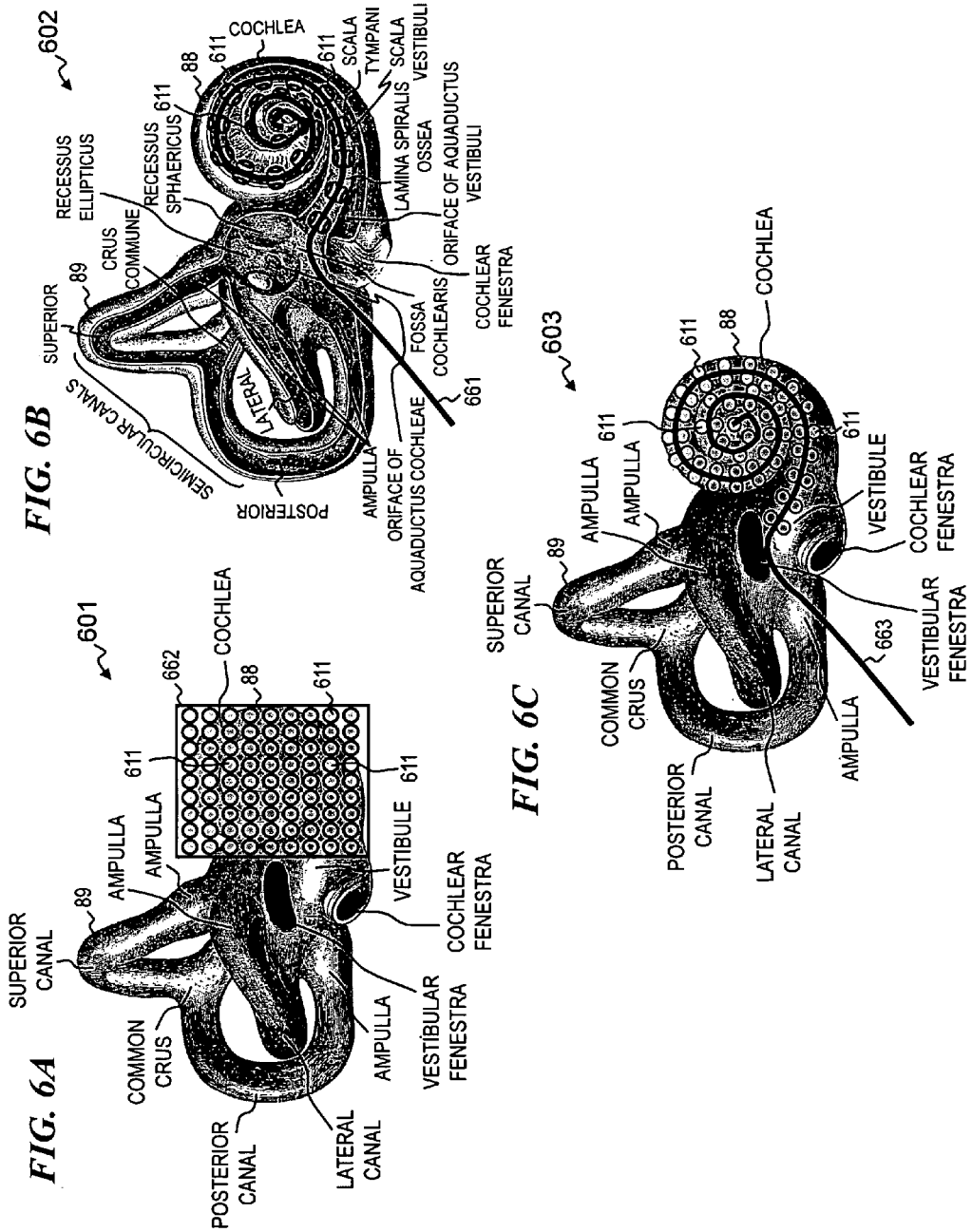

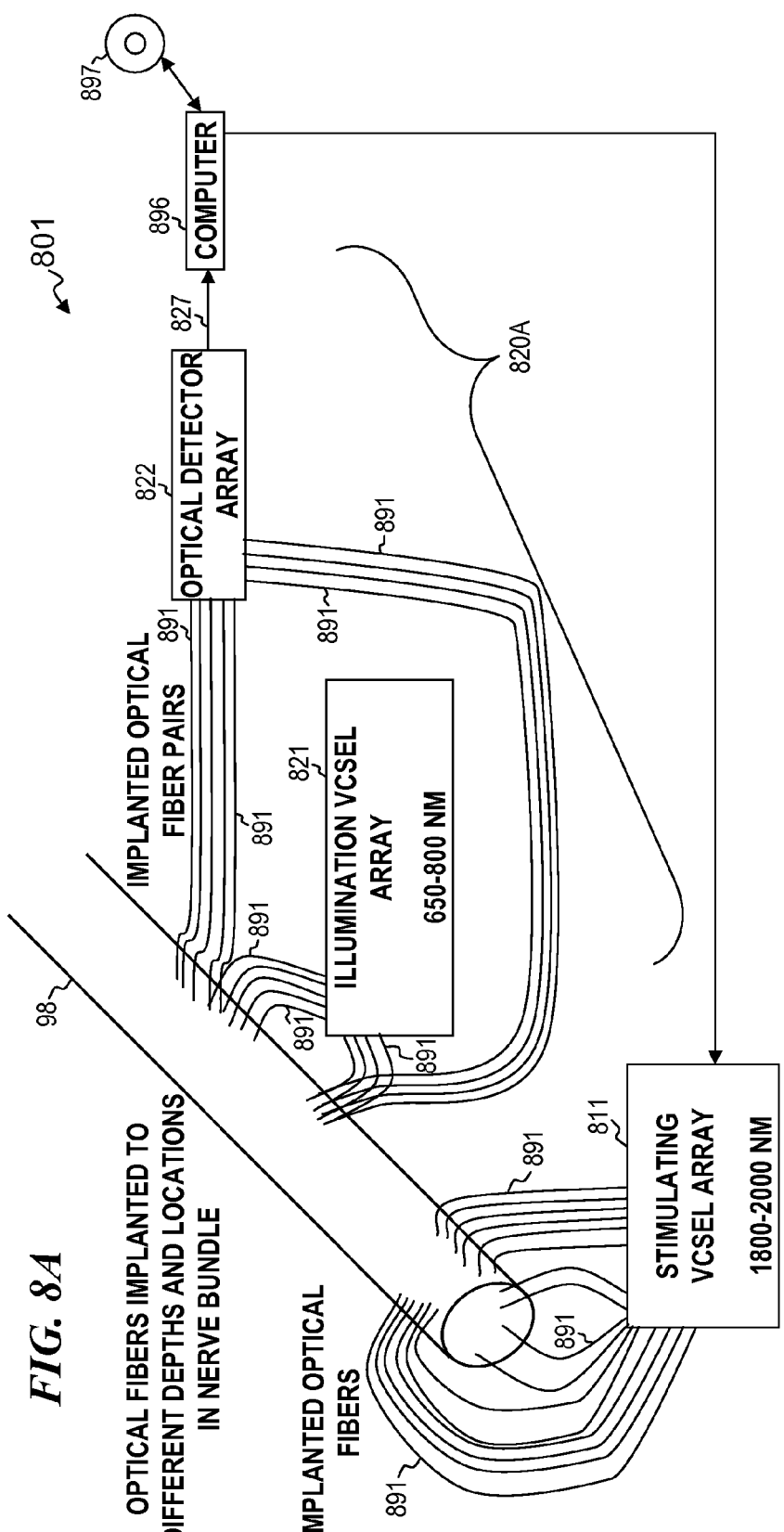

VCSEL ARRAY STIMULATOR APPARATUS AND METHOD FOR LIGHT STIMULATION OF BODILY TISSUES

CROSS-REFERENCE TO RELATED APPLICATIONS

This application claims benefit under 35 U.S.C. §119(e) of U.S. Provisional Patent Application No. 60/964,634 filed on Aug. 13, 2007, titled "VCSEL ARRAY STIMULATOR APPARATUS AND METHOD FOR LIGHT STIMULATION OF BODILY TISSUES," and U.S. Provisional Patent Application No. 61/081,732 filed on Jul. 17, 2008, titled "METHOD AND APPARATUS FOR NEURAL SIGNAL CAPTURE TO DRIVE NEUROPROSTHESES OR BODILY FUNCTION," which are both incorporated herein by reference in their entirety.

This invention is related to

U.S. Provisional Patent Application Ser. No. 60/884,619 filed Jan. 11, 2007, entitled "VESTIBULAR IMPLANT USING INFRARED NERVE STIMULATION,"

U.S. patent application Ser. No. 11/257,793 filed Oct. 24, 2005 (which issued as U.S. Pat. No. 7,736,382 on Jun. 15, 2010) titled "APPARATUS AND METHOD FOR OPTICAL STIMULATION OF NERVES AND OTHER ANIMAL TISSUE,"

U.S. patent application Ser. No. 11/536,639 filed Sep. 28, 2006 (which issued as U.S. Pat. No. 7,988,688 on Aug. 2, 2011) and titled "MINIATURE APPARATUS AND METHOD FOR OPTICAL STIMULATION OF NERVES AND OTHER ANIMAL TISSUE,"

U.S. patent application Ser. No. 11/948,912 filed Nov. 30, 2007 and titled "APPARATUS AND METHOD FOR CHARACTERIZING OPTICAL SOURCES USED WITH HUMAN AND ANIMAL TISSUES,"

U.S. patent application Ser. No. 11/536,642 filed Sep. 28, 2006 and titled "APPARATUS AND METHOD FOR STIMULATION OF NERVES AND AUTOMATED CONTROL OF SURGICAL INSTRUMENTS,"

U.S. patent application Ser. No. 11/971,874 filed Jan. 9, 2008 (which issued as U.S. Pat. No. 8,012,189 on Sep. 6, 2011) and titled "METHOD AND VESTIBULAR IMPLANT USING OPTICAL STIMULATION OF NERVES," and U.S. patent application Ser. No. 11/420,729 (which issued as U.S. Pat. No. 7,391,561 on Jun. 24, 2008) titled "FIBER- OR ROD-BASED OPTICAL SOURCE FEATURING A LARGE-CORE, RARE-EARTH-DOPED PHOTONIC-CRYSTAL DEVICE FOR GENERATION OF HIGH-POWER PULSED RADIATION AND METHOD" filed May 26, 2006, each of which is incorporated herein in its entirety by reference.

FIELD OF THE INVENTION

The invention relates generally to tissue optics (interactions of light with human or other-animal tissue), and more particularly to methods and apparatus for light stimulation of bodily tissues using a vertical-cavity surface-emitting-laser (VCSEL) array stimulator apparatus.

BACKGROUND OF THE INVENTION

It is desirable to cause a controlled stimulation of individual nerves. U.S. Pat. No. 6,921,413 issued to Mahadevan-Jansen et al. on Jul. 26, 2005, and titled "METHODS AND DEVICES FOR OPTICAL STIMULATION OF NEURAL TISSUES," is incorporated herein by reference. Mahadevan-Jansen et al. note that traditional methods of stimulation include electrical, mechanical, thermal, and chemical. A neuron will propagate an electrical impulse (a nerve action potential) in response to a stimulus. The most common form of applying such stimulation is to form a transient current or voltage pulse applied through electrodes. Electrical, mechanical, and chemical stimulations have many limitations. To name a few, stimulation by such methods typically results in non-specific stimulation of neurons and/or damage to neurons. Difficulty exists in recording electrical activity from the neuron due to an electrical artifact created by the stimulus. To stimulate only one or a few neurons, fragile micro-electrodes need to be fashioned and carefully inserted into the tissue to be stimulated. Such techniques do not easily lend themselves to implantable electrodes for long-term use in stimulation of neural tissue. Mahadevan-Jansen et al. describe the use of low-power light from a free-electron laser (FEL) for optically stimulating selected individual nerve cells in vivo, while at the same time not stimulating neighboring cells with the laser light. However, FELs are expensive, large, awkward and unwieldy.

Various patents have described lasers that emit in the infrared (e.g., U.S. Pat. No. 6,184,542 issued Feb. 6, 2001 to Gerard A. Alphonse; U.S. Pat. No. 6,301,279 issued Oct. 9, 2001 to Dmitri Z. Garbuzov, et al.; U.S. Pat. No. 6,339,606 issued Jan. 15, 2002 to Gerard A. Alphonse; U.S. Pat. No. 6,363,188 issued Mar. 26, 2002 to Gerard A. Alphonse; U.S. Pat. No. 6,417,524 issued Jul. 9, 2002 to Gerard A. Alphonse; U.S. Pat. No. 6,459,715 issued Oct. 1, 2002 to Viktor B. Khalfin, et al.; U.S. Pat. No. 6,556,611 issued Apr. 29, 2003 to Viktor B. Khalfin, et al.; U.S. Pat. No. 6,639,930 issued Oct. 28, 2003 to Giora Griffel, et al.; U.S. Pat. No. 6,669,379 issued Dec. 30, 2003 to Zbigniew Janosik, et al.; U.S. Pat. No. 6,688,783 issued Feb. 10, 2004 to Zbigniew Janosik, et al.; U.S. Pat. No. 6,744,548 issued Jun. 1, 2004 to Joseph H. Abeles; and U.S. Pat. No. 6,909,826 issued Jun. 21, 2005 to Yongming Cai, et al., all of which are incorporated herein by reference). However, conventional edge-emitting lasers must be cleaved before they are able to be tested, and assembly from individual lasers or linear strips of lasers into complex topologies is difficult and expensive. Further, these types of lasers have a high threshold level required to achieve lasing, requiring high power and generating excess heat, making them unsuitable for most applications requiring implanted devices in humans or other animals.

The present application is related to the following patents and applications, each of which is incorporated by reference: U.S. patent application Ser. No. 11/071,060 by Anita Mahadevan-Jansen et al. entitled "System and Methods for Optical Stimulation of Neural Tissues" filed Mar. 3, 2005; U.S. Pat. No. 6,310,083 by Joseph P. Y. Kao et al. issued Oct. 30, 2001, entitled "Caged amino acid derivatives bearing photolabile protective groups"; U.S. Pat. No. 5,430,175 to George P. Hess, et al. issued Jul. 4, 1995 titled "Caged carboxyl compounds and use thereof"

Various patents and patent applications have also described structures, materials and processes for making and using vertical-cavity surface-emitting lasers (VCSELs) (e.g., U.S. Patent Application Publication No. 2007-0036493A1 titled "Bidirectional optical fiber link systems components couplers," U.S. Patent Application Publication No. 2003-0165171A1 titled "Temperature compensated lasers," U.S. Patent Application Publication No. 2001-0021287A1 titled "Electro-opto-mechanical assembly for coupling a light source or receiver to an optical waveguide," each of which is incorporated by reference). All of the following are incorporated by reference: U.S. Pat. No. 7,095,770 to Ralph H.

Johnson titled "Vertical cavity surface emitting laser including indium, antimony and nitrogen in the active region" describes materials suitable for emitting laser light having wavelengths in the range of 1260 to 1650 nm. U.S. Pat. No. 5,754,578 to Jayaraman is titled "1250-1650 nm vertical cavity surface emitting laser pumped by a 700-1050 nm vertical cavity surface emitting laser." U.S. Pat. No. 5,799,030 to Mary K. Brenner is titled "Semiconductor device with a laser and a photodetector in a common container." U.S. Pat. No. 7,085,300 to Thomas R. Werner et al. is titled "Integral vertical cavity surface emitting laser and power monitor." U.S. Pat. No. 6,542,530 to Chan-Long Shieh et al. titled "Electrically pumped long-wavelength VCSEL and methods of fabrication" describes materials and structures for electrically pumped, long-wavelength VCSEL includes a long wavelength active region. Because nitrogen, indium, and Sb all reduce the band gap energy, the achievable wavelengths extend to wavelengths longer than either 1310 nm used for datacom or 1550 nm used for telecom. U.S. Patent Application Publication No. 2006-0276861A1 by J. T. Lin titled "Non-invasive method and system for the treatment of snoring and nasal obstruction" describes a laser for thermal shrinkage of soft tissue of uvula, soft palate, nasal turbinate or tongue base for the treatment of snoring, nasal obstruction or sleep apnea are disclosed. The preferred laser includes infrared laser about 0.7 to 1.85 micron, pulse duration about 100 microsecond to 5 seconds, spot size of about 2 to 5 mm and power of about 2 to 20 W at the treated area. U.S. Pat. No. 5,484,432 to Bruce J. Sand titled "Collagen treatment apparatus" described thermal shrinkage of collagen tissue by irradiation with coherent energy in the wavelength band of 1.80 to 2.55 microns as generated by a laser.

United States Patent Application 20030236458 titled "Spectroscopic systems and methods for detecting tissue properties" by Hochman, Daryl W. is herein incorporated by reference. The application describes methods for optically detecting physiological properties in an area of interest by detecting changes in the intrinsic or extrinsic optical properties of tissue in the area of interest are disclosed. The present invention optically detects blood flow changes, blood characteristics and blood vessel abnormalities, as well as determining the presence and location of abnormal or pathological tissue for identifying and mapping the margins of abnormal tissue, such as tumor tissue during surgical or diagnostic procedures, and for grading and characterizing tumor tissue. The application also describes systems and methods for distinguishing neuronal tissue from surrounding tissue, for distinguishing functional neuronal tissue from dysfunctional tissue, and for imaging functional neuronal areas in the cortex. Methods and systems of the described in the application may be implemented using a contrast enhancing agent or by stimulation of activity.

U.S. Pat. No. 7,194,063 titled "Methods for implementing microbeam radiation therapy" to Dilmanian; F. Avraham et al. is herein incorporated by reference. The patent describes a method of performing radiation therapy that includes delivering a therapeutic dose such as X-ray only to a target (e.g., tumor) with continuous broad beam (or in-effect continuous) using arrays of parallel planes of radiation (microbeams/microplanar beams). Microbeams spare normal tissues, and when interlaced at a tumor, form a broad-beam for tumor ablation. Bidirectional interlaced microbeam radiation therapy (BIMRT) uses two orthogonal arrays with inter-beam spacing equal to beam thickness. Multidirectional interlaced MRT (MIMRT) includes irradiations of arrays from several angles, which interleave at the target. Contrast agents, such as tungsten and gold, are administered to preferentially increase the target dose relative to the dose in normal tissue. Lighter elements, such as iodine and gadolinium, are used as scattering agents in conjunction with non-interleaving geometries of array(s) (e.g., unidirectional or cross-fired (intersecting) to generate a broad beam effect only within the target by preferentially increasing the valley dose within the tumor.

U.S. Pat. No. 7,003,353 titled "Photovoltaic powered charging apparatus for implanted rechargeable batteries" to Leon Parkhouse is herein incorporated by reference. The patent describes a photovoltaic powered charging unit that is mounted in a head covering, such as a cap or hat, for a patient who has an inductively chargeable medical device implanted in his head. The implanted device includes an implanted battery which powers the device. The photovoltaic cells provide continuous charging for the implanted battery and power for the implanted device when subjected to light. The charging unit includes a nonphotovoltaic cell that may be used to charge the implanted battery and power the implanted device in the absence of sufficient power from the photovoltaic cells. The cap has a sending coil located so that when the wearer dons the cap, the sending coil aligns with a receiving coil implanted in the patient's skull or brain. The implanted receiving coil is coupled to provide charging current to the implanted battery and power to the implanted device.

United States Patent Application 20080183247 titled, "Radio frequency transponder based implantable medical system" by Harding, William C. is herein incorporated by reference. This application describes an implantable medical device (IMD) system that includes an IMD, a transceiver antenna lead for the IMD, and a wireless therapy delivery transponder or probe that is remotely activated by the IMD via the transceiver antenna lead. The IMD and the wireless probe communicate using wireless RF-based transponder techniques. The wireless probe includes a capacitor that is charged when the IMD emits an appropriate electromagnetic field from the transceiver antenna lead. The wireless probe delivers electrical therapy in the form of electrical pulses from the capacitor in response to RF activation signals emitted by the IMD via the transceiver antenna lead.

U.S. Pat. No. 6,823,109 titled, "Optical fiber-lens array" to Sasaki, Yasuji et al. is herein incorporated by reference. This patent describes an optical fiber-lens array, wherein the optical axes of the gradient index rod lens and of the optical fiber are aligned easily with high accuracy. The optical fiber-lens array includes a first substrate having a gradient index rod lens accommodated in V-shaped grooves for rod lenses formed in parallel at prescribed pitches, and a second substrate having optical fibers accommodated in V-shaped grooves for optical fibers formed at the same array pitches with said V-shaped grooves for rod lenses. The first substrate and the second substrate are connected by guide pins placed on the common positioning guide grooves formed on the first substrate and the second substrate with the respective end surfaces of the gradient index rod lenses and the respective end surfaces of the corresponding optical fibers faced toward each other.

Background on Neural Stimulation

Neural prosthetic devices are artificial extensions to the body that restore or supplement nervous-system function that was lost during disease or injury. The devices stimulate remaining neural tissue, providing some input to the nervous system through multiple independent channels that work in parallel to provide an overall effect within the body. Heretofore, the challenge for neural prostheses is to stimulate neurons selectively with individual channels. However, the electrical current spreads widely in the tissue and does not allow easily stimulating small neuron populations. This limitation is based on fundamental physical principles of electrical stimulation that even the best electrode design has not yet overcome.

Researchers have therefore shifted their focus toward improving electrodes and stimulation paradigms. Recent animal experiments have caused a fundamental paradigm shift in the field of neural stimulation, namely the use of light rather than electrical energy to induce nerve potentials. In particular, Aculight Corporation has previously developed a novel infrared neuro-stimulator that uses light to activate neurons. The advantage of the novel device over existing contemporary devices includes its non-invasive character of stimulating the nerve and the possibility of focusing the stimulus to extremely small populations of neurons allowing for spatial stimulation that mimics better the natural stimulation of the neurons. The technology will not only serve the hearing impaired but will help to define the laser parameters necessary to develop any other neural prostheses that require fast repetition rates of stimulation, including vestibular or possible retinal prostheses. For light stimulation to be practical in an implant, a technology must be used that is compact, power efficient, and consists of an array of lasers with the capability of electronic control of individual channels.

What are needed are improved methods and apparatus for stimulation of bodily tissues (such as stimulating one or more nerves together or separately) using light (such as infrared laser light from an array of lasers).

SUMMARY OF THE INVENTION

The present invention provides an apparatus and process wherein an array of two or more vertical-cavity surface-emitting lasers (VCSELs) are operatively coupled to emit light onto animal tissue (such as human nerve tissue) to stimulate a response (such as a nerve action potential (NAP)). In some embodiments, the VCSEL array is part of a device that is implanted and/or affixed externally to the body and coupled to stimulate and/or sense nerve signals from a particular site such as the brain (e.g., to treat epilepsy, sight loss, and the like), the inner ear (e.g., to treat hearing loss, balance problems, and the like), the eye or optic nerve (to restore or provide a vision-like sense), the site of an amputation or paralysis (e.g., to provide tactile feedback from a prosthesis, alleviate pain, and the like) or other suitable location and/or use.

In some embodiments, the device also includes a sensor or signal receiver that obtains environmental information (such as audio, visual, temperature, odor, taste, balance or orientation, tactile or feel (size, shape, hardness, slipperiness, stickiness, roughness, weight, resistance to movement, and the like)), a processor that receives the signal(s) and/or sensory data and determines which light signal (the various temporal characteristics, spatial characteristics, power characteristics, and the like) is needed, and where, to invoke the desired response in the tissue (e.g., the stimulation needed to generate the nerve signals that would be interpreted by the patient to be the sight, sound, smell, taste, touch, orientation/balance and the like), a drive circuit that generates the electrical signals needed to drive one or more elements of the VCSEL array, and one or more VCSEL arrays (and/or their coupling optics) operatively coupled to receive the electrical signals, and to emit the laser light to the tissue to be stimulated. In some embodiments, the tissue to be stimulated is below the skin or behind one or more other layers of tissue relative to the one or more VCSEL arrays (and/or their coupling optics), and the emitted light passes through those intermediate tissues to arrive upon and stimulate the nerve or other tissue to which the stimulation is intended.

BRIEF DESCRIPTION OF THE DRAWINGS

FIG. 2A is a block diagram of a two-dimensional VCSEL array 201 capable of light stimulation of animal tissue, selective illumination of animal tissue and detection of activity within the animal tissue.

FIG. 2B is a block diagram of a one-dimensional VCSEL array 202 capable of light stimulation of animal tissue, selective illumination of animal tissue and detection of activity within the animal tissue.

FIG. 3A is a block diagram of 301 that uses an integrated VCSEL/detector array for light stimulation of animal tissue, selective illumination of animal tissue and detection of activity within the animal tissue.

FIG. 3B is a block diagram of 302 that uses multiple VCSEL arrays for light stimulation of animal tissue, selective illumination of animal tissue and a detector array for detection of activity within the animal tissue.

FIG. 4A is a block diagram of system 401 that uses VCSEL flex-cuffs for light stimulation of a severed nerve, selective illumination of the severed nerve and detection of activity within the severed nerve.

FIG. 6A is a diagram of system 601 showing a two-dimensional VCSEL array used for targeting the cochlear nerve of the cochlea within the inner ear.

FIG. 6B is a diagram of system 602 showing a VCSEL flex-circuit array capable of being inserted into the cochlea within the inner ear to stimulate the cochlear nerve.

FIG. 6C is a diagram of system 603 showing a VCSEL flex-circuit array capable of being implanted next to the cochlea or attached directly to the exterior of the cochlea within the inner ear to stimulate the cochlear nerve.

FIG. 8A is a block diagram of system 801 using implantable optical fibers capable of light stimulation of animal tissue, selective illumination of animal tissue and detection of activity within the animal tissue.

DETAILED DESCRIPTION

Figure 1A:
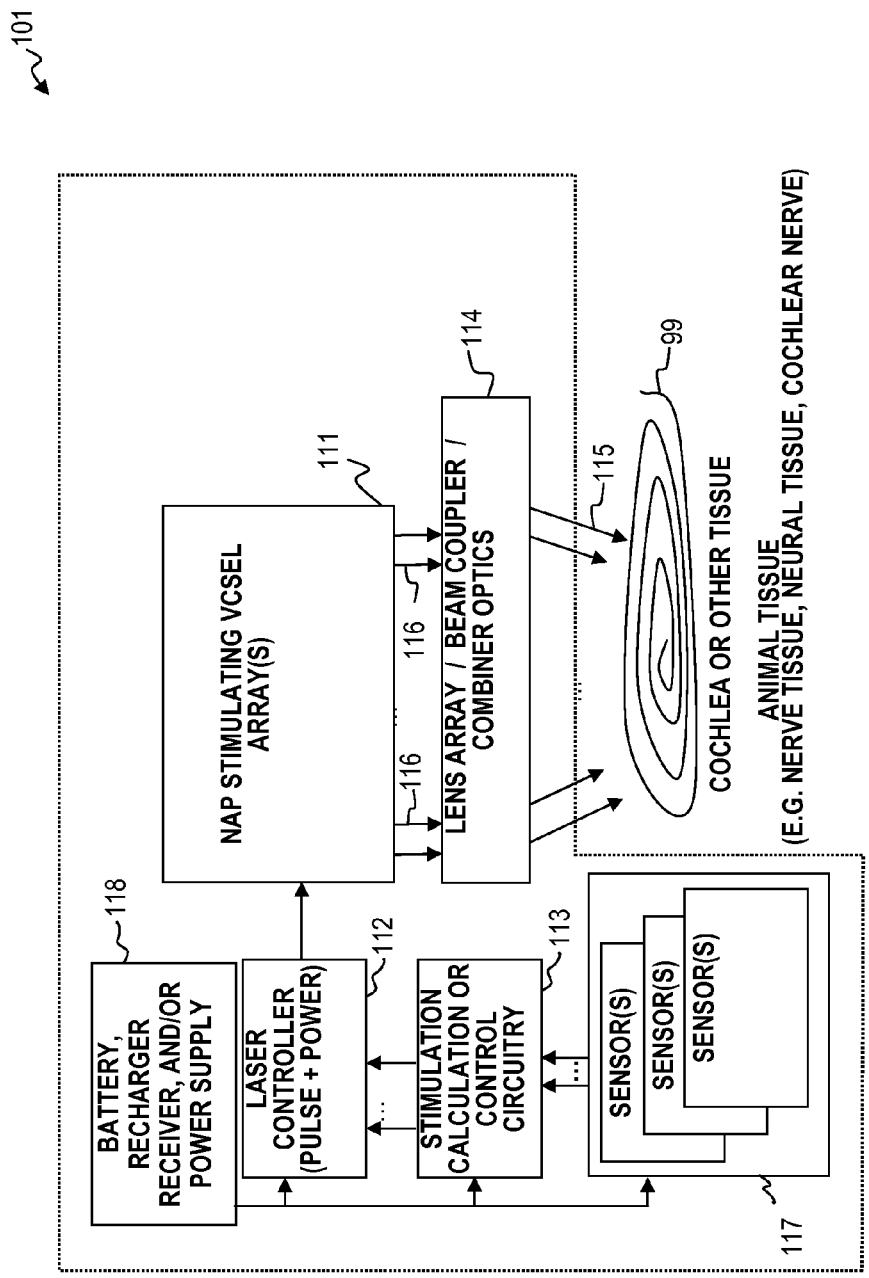
FIG. 1A is a block diagram of an implantable system 101 that uses a VCSEL array for light stimulation of animal tissue.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple figures. Signals and connections may be referred to by the same reference number or label, and the actual meaning will be clear from its use in the context of the description.

In some embodiments, the present invention provides a sequence of optical (e.g., laser) pulses from a VCSEL array, configured in space and time to stimulate a plurality of nerves of a human person.

In some embodiments, the present invention provides a VCSEL device for a specific group of applications in biology. Specifically, some embodiments include use of VCSELs for light stimulation of cellular activity (more specifically for neural implantable devices). In each case (i.e., VCSEL technology and light stimulation technology), the conventional technology does not describe the use of VCSELs for light stimulation (see later definition), as described in the following discussion of the present invention. There are a variety of permutations within this invention related to the following:

In some embodiments, the primary device technology includes VCSELs for light stimulation of animal tissue. Light stimulation can be achieved by different methods according to the present invention, both direct and indirect, that require different laser parameters to get the desired result in tissue. In some embodiments, optical stimulation (direct) requires pulsed infrared light, while photostimulation (indirect) requires that a cell or group of cells be genetically or pharmaceutically modified to respond to ultraviolet or visible light. Thus, in various embodiments, the device parameters that are specified and/or used by the present invention include various laser parameters that could be varied and used for light stimulation—including wavelength, pulse duration, pulse shape, pulse-repetition rate and laser intensity. The various embodiments of the present invention use a wide variety of output light wavelengths (including using one or more wavelengths simultaneously, using one or more wavelengths sequentially, and/or using one or more wavelengths of different intensities), since almost all ultraviolet (UV), visible, and infrared (IR) wavelengths are used for the different ways that light can stimulate tissue.

In some embodiments, this device forms the stimulator portion of a prosthetic device for therapy of damaged cells, tissues, or organs. The uses include vestibular, cochlear, or retinal implants. There are a number of other uses that are related to restoration of neurocognitive function (deep brain stimulators), and/or cardiac pacing, muscle excitation, control of endocrine systems (like pituitary glands), and the like. In various embodiments, the present invention provides stimulation of any cell, tissue, or effector system with the use of light from an array of two or more VCSELs. For each application there are a number of different sites that can be stimulated to control biological activity with light.

For the prosthetic component, some embodiments of the device are interfaced to a sensor technology of a suitable type, which inputs to a software control system, which generates signals to control the stimulator light-generation portion. In some embodiments, the stimulator portion includes individual control of each of a plurality of lasers within the array such that each individual signal channel can respond by emitting light with the appropriate parameter to a specific tissue site, such that any portion up to the entire biological system is stimulated selectively to most-appropriately mimic normal cellular function.

In various embodiments, optical-fiber or free-beam transmission of the optical signals are used to deliver the light to the tissue. For prosthetic devices that are implanted, the position of each individual channel is critical. The key is that this light from individual channels will appropriately irradiate the tissue with the correct laser-beam geometry and laser parameters to excite cellular function within that irradiated site. Appropriately timed and spaced stimulation with multiple channels should ultimately restore function in the appropriate biological system (e.g., retina, vestibule, cochlea, etc.)

In some such embodiments, the VCSEL array allows reprogramming the device if and when the VCSEL array may shift from its optimal position. In some embodiments, the reprogramming remaps which VCSEL devices are activated to emit light to stimulate a particular location. For example, the VCSEL array might shift as a whole relative to the nerves it is intended to stimulate by some amount (e.g., three pixels in the X direction and one pixel in the Y direction), and the processor rather than using the originally-programmed VCSELs, would instead change the mapping and use VCSELs in the array that are each three pixels over in the X direction and one pixel down in the Y direction from those originally used, in order to continue to stimulate the desired nerves.

FIG. 1A is a block diagram of an implantable system 101 that uses a VCSEL array for light stimulation of animal tissue. In some embodiments of the present invention, system 101 provides a low-power, low-threshold VCSEL array 111 that emits laser beams of light from each of a plurality of VCSELs, (e.g., VCSELs implemented as an array of separately activatable lasers formed in a monolithic semiconductor chip) wherein the laser light is capable of stimulating (e.g., stimulating an action potential or the like) animal tissue 99 (e.g., nerve tissue, neural tissue, cochlear nerve tissue, or the like). In some embodiments, the pulse shape and power of each laser beam is separately controlled by laser-controller 112 that drives the laser-diode VCSELs under control of a processor or circuitry 113 that generates light pulse signals that are configured to stimulate the tissue as desired. For example, in some embodiments, the light signals 116 emitted by the VCSEL array are collimated, focused and/or guided by optics 114 and output onto the animal tissue 99. In some embodiments, power is provided to the VCSEL array 111 through the laser controller 112 from the power unit 118 (e.g., a rechargeable battery pack, a power supply, inductively powered by an external power source, or the like). In some embodiments, the power unit 118 has a rechargeable battery pack (e.g., one or more batteries) that can be inductively recharged transcutaneously and a recharging receiver capable of electromagnetic coupling with an external apparatus using inductive and propagation techniques. In some embodiments, the wavelength of the light pulse is in the range of from about 1.8 microns to about 2.0 microns. In some other embodiments, the wavelength of the light pulse is about 1870 nm. In yet some other embodiments, the wavelength of the light pulse is in the range of from about 1.5 microns to 1.6 microns. In some embodiments, very short pulses are used (e.g., pulses that are shorter than 1 nsec, or in the range of 1 nsec to 10 nsec). In some embodiments, the light pulse from each individual VCSEL of the VCSEL array is capable of stimulating a different nerve (e.g., in a nerve bundle, the light pulse from each individual VCSEL of the VCSEL array is capable of individually providing stimulating light to a different fascicle in the nerve bundle). In some embodiments, one or more sensors 117 provides information (e.g., audio, visual, temperature, odor, taste, balance or orientation, tactile, feel or the like) to the control circuitry 113 wherein the control circuitry 113 receives the sensor information and processes the sensor information in order to provide the laser controller 112 with the appropriate stimulation pulse signal information.

Figure 1B:
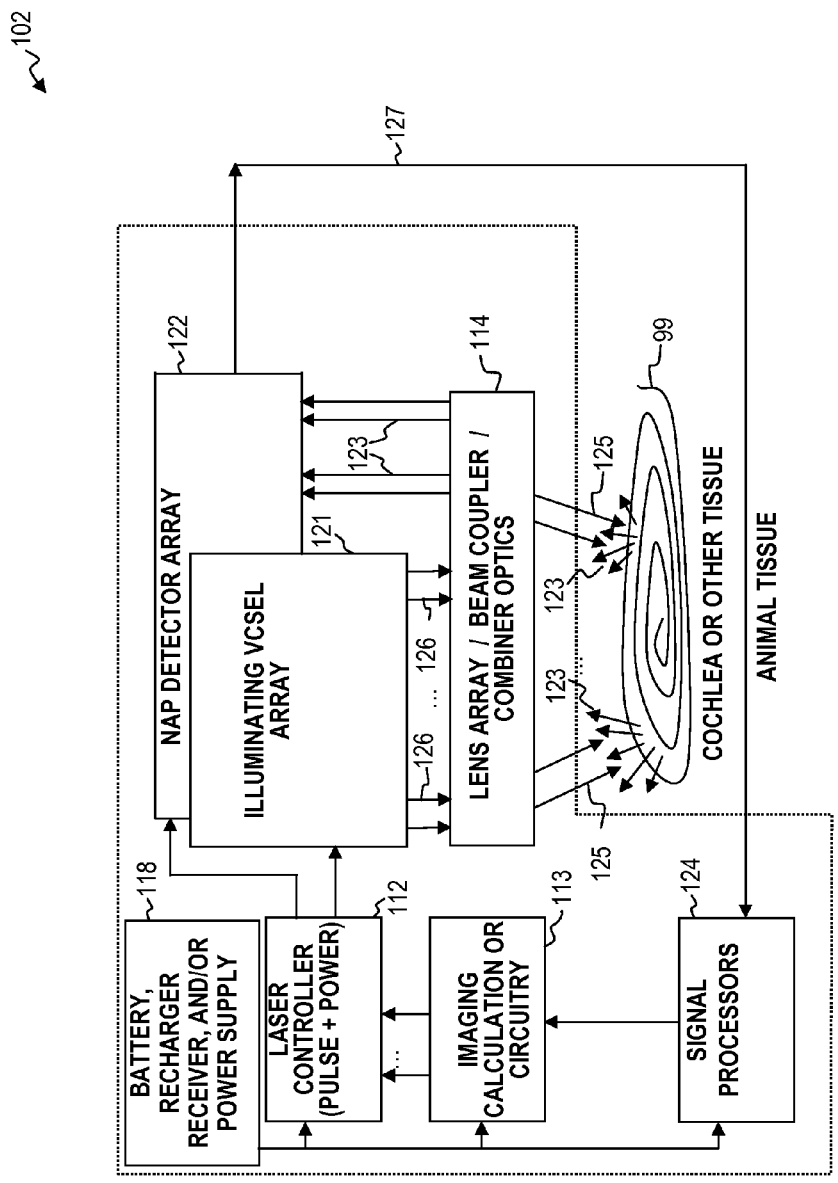
FIG. 1B is a block diagram of an implantable system 102 that uses VCSEL array(s) for selective illumination of animal tissue and detector array(s) for detection of activity within the animal tissue.

FIG. 1B is a block diagram of an implantable system 102 that uses VCSEL array(s) for selective illumination of animal tissue and detector array(s) for detection of activity within the animal tissue. In some embodiments of the present invention, system 102 provides a low-power, low-threshold VCSEL array 121 that emits laser light from each of a plurality of VCSELs, (e.g., VCSELs implemented as an array of separately activatable lasers formed in a monolithic semiconductor chip) wherein the laser light is capable of selectively illuminating animal tissue 99 (e.g., nerve tissue, neural tissue, cochlear nerve tissue, or the like) and a sensor array 122 that detects reflected light 123 from the animal tissue 99 and provides a reflected light signal 127 to a signal processor 124 that processes the provided signal information to detect the presence of activity in the illuminated animal tissue 99 (e.g., in some embodiments, the sensor array 122 can detect a nerve activity such as a nerve action potential (NAP) or nerve impulse to determine if a signal has been sent from the brain, or the sensor array can detect a change in various biological parameters (e.g., the water content of animal tissue) to determine a biological response to certain stimulation either external or internal, or the like). In some embodiments, the pulse shape and power of the laser beams emitted by each individual VCSEL in the VCSEL array is individually controlled by laser controller 112 that drives the laser-diode VCSELs under control of a processor or circuitry 113 that generates light pulse signals that are configured to selectively illuminate the tissue as desired. For example, in some embodiments, the illumination light signals 126 emitted by the VCSEL array 121 are collimated, focused and/or guided by optics 114 and output 125 onto the animal tissue 99. In some embodiments, power is provided to the VCSEL array 121 through the laser controller 112 from the power unit 118 (e.g., a rechargeable battery pack, a power supply, or the like). In some embodiments, the power unit 118 has a rechargeable battery pack (e.g., one or more batteries) that can be inductively recharged transcutaneously and a recharging receiver capable of electromagnetic coupling with an external apparatus using inductive and propagation techniques. In some embodiments, the wavelength of the light pulse is in the range of from about 650 nm to about 850 nm. In some other embodiments, light pulses with a wavelength of about 830 nm are used to improve signal-to-noise (s/n) however other embodiments use one or more different wavelengths in the range of 800 nm to 850 nm. In some embodiments, very short pulses are used (e.g., pulses that are shorter than 1 nsec, or in the range of 1 nsec to 10 nsec). In some embodiments, the light pulse from each individual VCSEL of the VCSEL array is capable of illuminating a different nerve (e.g., in a nerve bundle, the light pulse from each individual VCSEL of the VCSEL array is capable is individually providing light illumination to a different fascicle in the nerve bundle, or in other words the light from each individual VCSEL selectively provides illumination to one fascicle in the nerve bundle without or nearly without illuminating the neighboring fascicles in the nerve bundle). In some embodiments, system 102 is capable of detecting nerve signals intended to control muscles, and which detected signals are in turn used to control such things as actuators on the prosthesis (graspers, limb movers, and the like). In some embodiments, system 102 is capable of detecting light pulses 123 produced by the activity of action potentials in the illuminated tissues 99, wherein the tissue has been altered or genetically modified such that the tissue is responsive to incident light (e.g., photostimulation).

Figure 1C:
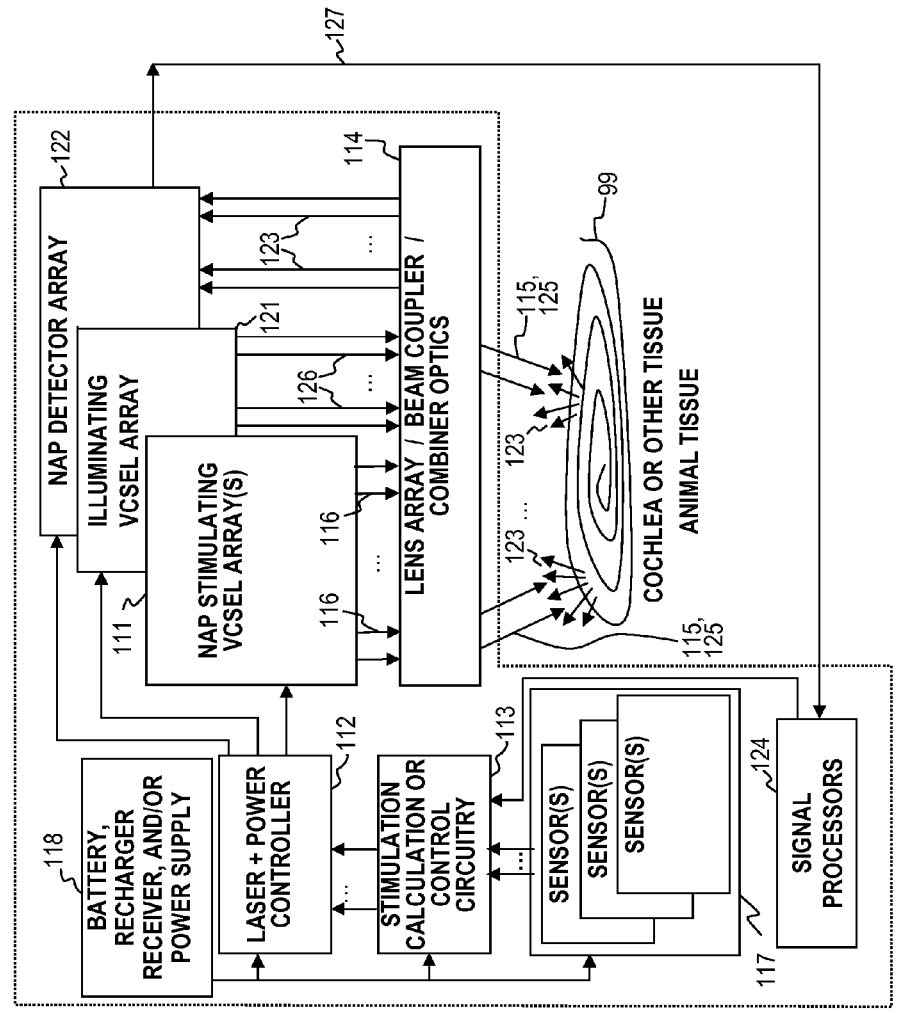
FIG. 1C is a block diagram of an implantable system 103 that uses multiple VCSEL and detector arrays for light stimulation of animal tissue, selective illumination of animal tissue and detection of activity within the animal tissue.

FIG. 1C is a block diagram of an implantable system 103 that uses multiple VCSEL arrays for light stimulation of animal tissue, selective illumination of animal tissue and detector array(s) for detection of activity within the animal tissue. In some embodiments, system 103 combines the tissue stimulation capabilities of system 101, as described above, with the selective tissue illumination and tissue activity detection of system 102, also as described above, into a single system. In some embodiments of the present invention, system 103 provides a low-power, low-threshold VCSEL array 111 that emits laser beams of light from each of a plurality of VCSELs, (e.g., VCSELs implemented as an array of separately activatable lasers formed in a monolithic semiconductor chip) wherein the laser light is capable of stimulating animal tissue 99 (e.g., nerve tissue, neural tissue, cochlear nerve tissue, or the like), a low-power, low-threshold VCSEL array 121 that emits laser light from each of a plurality of VCSELs, (e.g., VCSELs implemented as an array of separately activatable lasers formed in a monolithic semiconductor chip) wherein the laser light is capable of selectively illuminating animal tissue 99 (e.g., nerve tissue, neural tissue, cochlear nerve tissue, or the like) and a sensor array 122 that detects reflected light 123 from the animal tissue 99 and provides a reflected light signal 127 to a signal processor 124 that processes the provided signal information to detect the presence of activity in the illuminated animal tissue 99 (e.g., in some embodiments, the sensor array 122 can detect a nerve activity such as a nerve action potential (NAP) or nerve impulse to determine if a signal has been sent from the brain, or the sensor array can detect a change in various biological parameters (e.g., the water content of animal tissue) to determine a biological response to certain stimulation either external or internal, or the like). In some embodiments, the pulse shape and power of each stimulating light pulse and each illuminating light pulse is separately controlled by laser-controller 112 that drives the laser-diode VCSELs under control of a processor or circuitry 113 that generates light pulse signals that are configured to stimulate and illuminate the tissue as desired. For example, in some embodiments, the light signals (i.e., stimulating light signal 116 and illuminating light signal 126) emitted by the VCSEL arrays are collimated, focused and/or guided by optics 114 and output (i.e., 115 and 125 respectively) onto the animal tissue 99. In some embodiments, power is provided to the VCSEL array 121 through the laser controller 112 from the power unit 118 (e.g., a rechargeable battery pack, a power supply, or the like). In some embodiments, the power unit 118 has a rechargeable battery pack (e.g., one or more batteries) that can be inductively recharged transcutaneously and a recharging receiver capable of electromagnetic coupling with an external apparatus using inductive and propagation techniques. In some embodiments, the wavelength of the stimulating light pulse 116 is in the range of from about 1.8 microns to about 2.0 microns. In some other embodiments, the wavelength of the stimulating light pulse 116 is about 1870 nm. In yet some other embodiments, the wavelength of the stimulating light pulse 116 is in the range of from about 1.5 microns to 1.6 microns. In some embodiments, the wavelength of the illuminating light pulse 126 is in the range of from about 650 nm to about 850 nm. In some other embodiments, illuminating light pulses 126 with a wavelength of about 830 nm are used to improve signal-to-noise (s/n) however other embodiments use one or more different wavelengths of illuminating light pulses 126 in the range 800 nm to 850 nm. In some embodiments, very short pulses are used (e.g., pulses that are shorter than 1 nsec, or in the range of 1 nsec to 10 nsec) for both the stimulating light pulses and the illuminating light pulses. As discussed above for both system 101 and system 102, in some embodiments, each stimulating light pulse 116 from each VCSEL in the stimulating VCSEL array and each illuminating light pulse 126 in each VCSEL of the illuminating VCSEL array is capable of targeting individual nerves such that neighboring nerves are not or nearly not stimulated or illuminated. In some embodiments, system 103 is capable of stimulating nerve action potentials based on information provided by sensors (e.g., pressure sensors) in a prosthesis and detecting nerve signals provided from the brain and intended to control muscles, and which detected signals are in turn used to control such things as actuators on the prosthesis (graspers, limb movers, and the like).

Figure 1D:
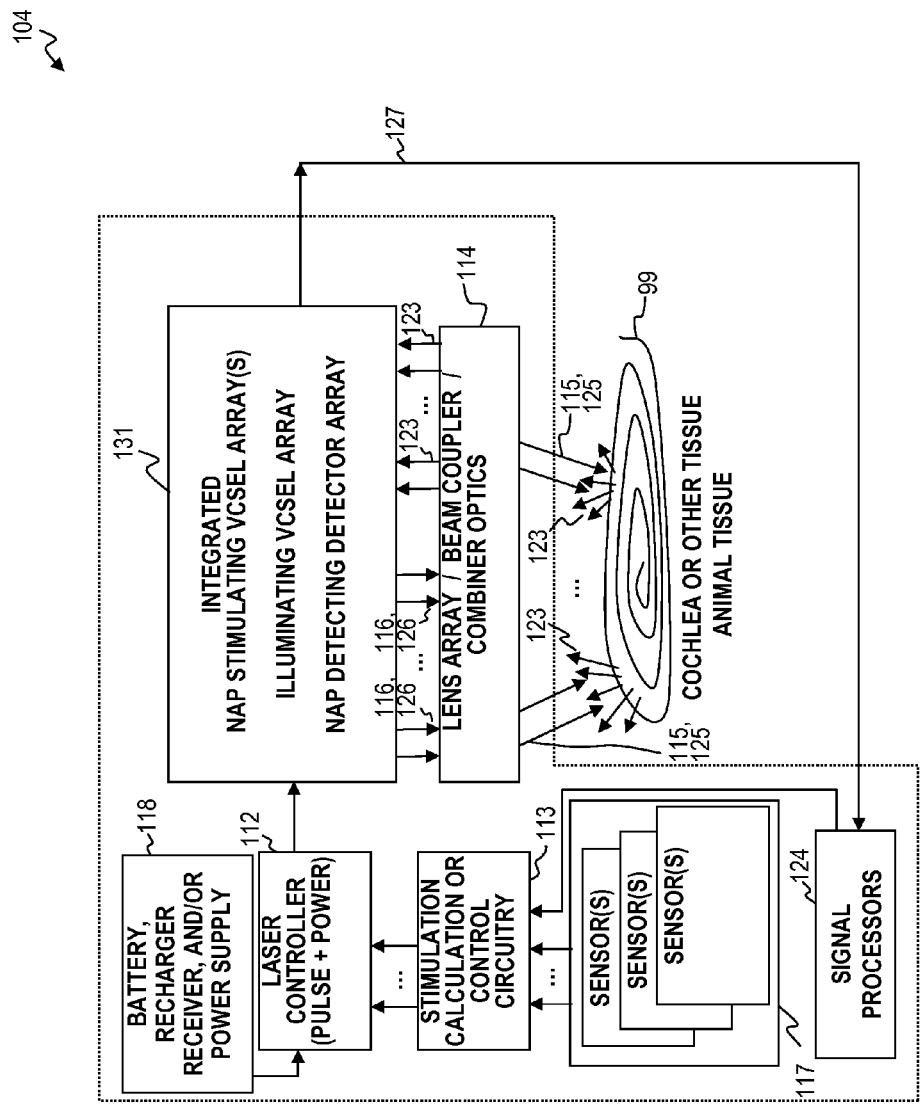
FIG. 1D is a block diagram of an implantable system 104 that uses a single integrated VCSEL/detector array for light stimulation of animal tissue, selective illumination of animal tissue and detection of activity within the animal tissue.

FIG. 1D is a block diagram of an implantable system 104 that uses a single integrated VCSEL/detector array for light stimulation of animal tissue, selective illumination of animal tissue and detection of activity within the animal tissue. In some embodiments, system 104 provides the capabilities of system 103, as described above, however, in contrast to system 103, for system 104 the tissue stimulation VCSEL array, the selective tissue illumination VCSEL array and the reflected-light detector array have been integrated onto a single monolithic semiconductor chip 131. In some embodiments of the present invention, system 104 provides a low-power, low-threshold VCSEL/detector array 131 that integrates stimulating light emitting VCSELs, illuminating light emitting VCSELs and detectors onto a single semiconductor chip. In some embodiments, VCSEL/detector array 131 is integrated using a semiconductor material capable of both electrical and optical activity (e.g., in some embodiments, InGaAs, InGaAsP, AlGaAs, or the like are used as the semiconductor material). Other capabilities of system 104 are similar to system 103 as discussed above.

Figure 1E:
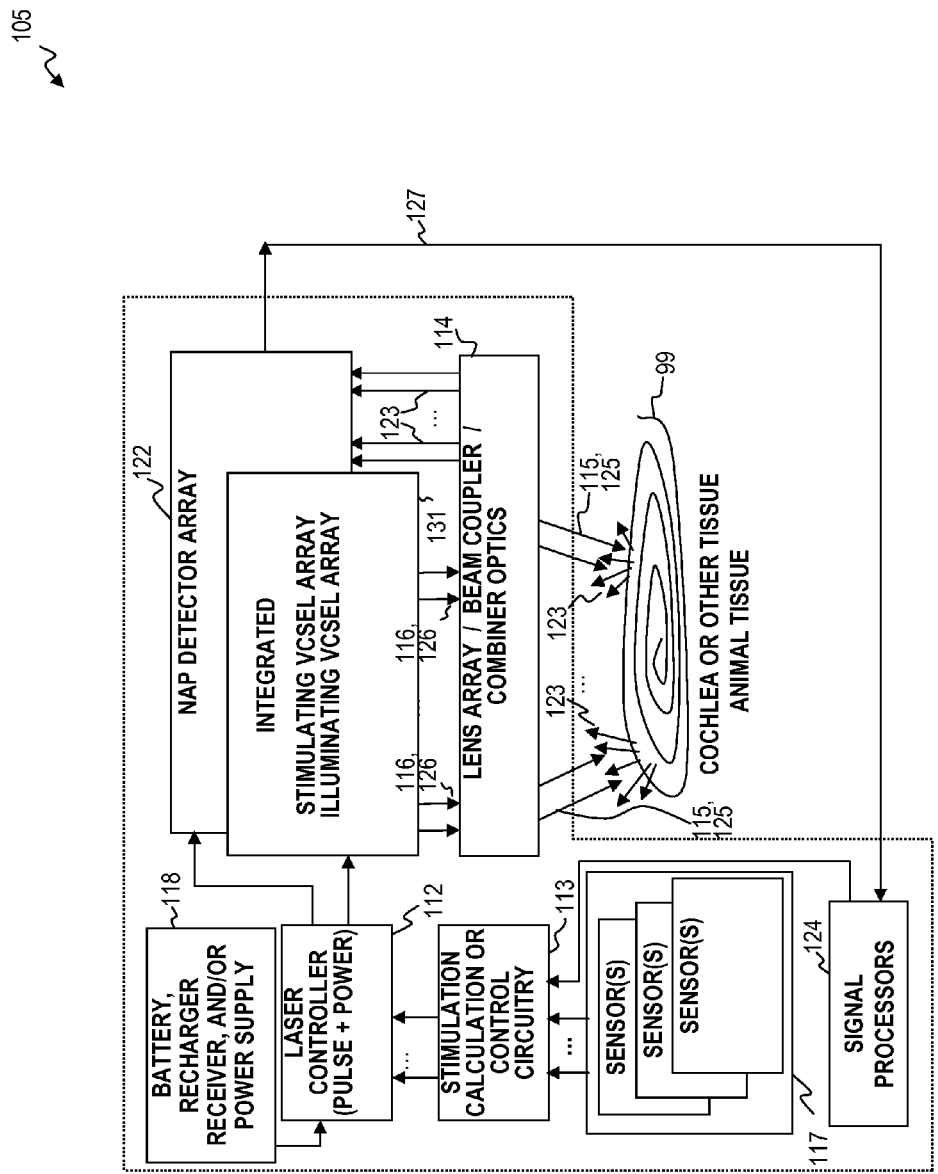
FIG. 1E is a block diagram of an implantable system 105 that uses a single integrated VCSEL array for light stimulation of animal tissue and selective illumination of animal tissue and a detector array for detection of activity within the animal tissue.

FIG. 1E is a block diagram of an implantable system 105 that uses a single integrated VCSEL array for light stimulation of animal tissue and selective illumination of animal tissue and a detector array for detection of activity within the animal tissue. In some embodiments, system 105 provides the capabilities of system 103, as described above, however, in contrast to system 103, for system 105 the tissue stimulation VCSEL array and the selective tissue illumination VCSEL array have been integrated onto a single monolithic semiconductor chip 131 and the reflected-light detector array 122 is provided by a separate semiconductor chip. In some embodiments of the present invention, system 105 provides a low-power, low-threshold VCSEL array 131 that integrates stimulating light emitting VCSELs and illuminating light emitting VCSELs onto a single semiconductor chip 131 and the reflected-light detector array is provided by a separate semiconductor chip. In some embodiments, integrated VCSEL array 131 is integrated using a semiconductor material capable of both electrical and optical activity (e.g., in some embodiments, InGaAs, InGaAsP, AlGaAs, or the like are used as the semiconductor material). Other capabilities of system 105 are similar to system 103 as discussed above.

In some embodiments, for the systems described above (i.e., system 101, system 102, system 103, system 104 and system 105) and the control electronics (e.g., laser controller 112 and control circuitry 113 and the like) are integrated with the optical components (e.g., stimulating light emitting VCSELs, illuminating light emitting VCSELs and reflected-light detector array) onto a single monolithic semiconductor chip. In some embodiments, the control electronics and the optical components are integrated using a semiconductor material capable of both electrical and optical activity (e.g., in some embodiments, InGaAs, InGaAsP, AlGaAs, or the like are used as the semiconductor material). In some other embodiments, the control electronics and the optical components are integrated using a hybrid integration approach where the optical components are provided using InGaAsP or some other appropriate semiconductor material capable of supporting optical activity (e.g., InGaAs, InGaAsP, AlGaAs, GaN, AlGaN, InGaN, InGaP, GaSb, and the like) and the control electronics are provided using silicon and the optical components chip and the control electronics chip are integrated together by bump bonding or some other method suitable method. In some embodiments, integrating the optical components and the control electronics using separate chips allows independent optimization of the optical components and control electronics and is generally easier until a fully integrated fabrication process is mature.

FIG. 2A is a block diagram of a two-dimensional VCSEL array 201 capable of light stimulation of animal tissue, selective illumination of animal tissue and detection of activity within the animal tissue. In some embodiments, two-dimensional VCSEL array 201 integrates on a single monolithic semiconductor chip stimulating VCSELs 211 configured to emit light pulses 216 capable of stimulating animal tissue, illuminating VCSELs 221 configured to emit light pulses 226 capable of selectively illuminating animal tissue and detectors 222 capable of detecting light reflected by the illuminating lights impinging on the animal tissue. In some embodiments, the stimulating VCSELs 211, the illuminating VCSELs 221 and the detectors 222 are arranged in a repeating pattern (i.e., a cell 232) across the semiconductor chip such that each cell 232 contains at least one stimulating VCSEL 211, at least one illuminating VCSEL 221, and at least one detector 222. In some embodiments, each cell 232 contains at least one stimulating VCSEL 211, at least one illuminating VCSEL 221, and a plurality of detectors 222 such that the plurality of detectors 222 are arranged circumferentially around the illuminating VCSEL 221, thereby improving the ability of the detectors 222 to receive light reflected from the animal tissue at a plurality of angles. In some embodiments, each stimulating VCSEL 211 and each illuminating VCSEL 221 in each cell 232 is able to be uniquely activated. In some embodiments, the stimulating VCSELs 211 emit light pulses 216 having a wavelength in the range of from about 1.8 microns to about 2.0 microns. In some other embodiments, the wavelength of the light pulses 216 are about 1870 nm. In yet some other embodiments, the wavelength of the light pulses 216 are in the range of from about 1.5 microns to 1.6 microns. In some embodiments, the illuminating VCSELs 221 emit light pulses 226 having a wavelength in the range of from about 650 nm to about 850 nm. In some other embodiments, light pulses 226 with a wavelength of about 830 nm are used to improve signal-to-noise (s/n); however other embodiments use illuminating light pulses 226 with one or more different wavelengths in the range of 800 nm to 850 nm.

FIG. 2B is a block diagram of a one-dimensional VCSEL array 202 capable of light stimulation of animal tissue, selective illumination of animal tissue and detection of activity within the animal tissue. In some embodiments, one-dimensional VCSEL array 202 integrates on a single monolithic semiconductor chip stimulating VCSELs 211 configured to emit light pulses 216 capable of stimulating animal tissue, illuminating VCSELs 221 configured to emit light pulses 226 capable of selectively illuminating animal tissue and detectors 222 capable of detecting light reflected by the illuminating lights impinging on the animal tissue. In some embodiments, the stimulating VCSELs 211, the illuminating VCSELs 221 and the detectors 222 are arranged in a repeating pattern (i.e., a cell 232) across the semiconductor chip such that each cell 232 contains at least one stimulating VCSEL 211, at least one illuminating VCSEL 221, and at least one detector 222. In some embodiments, each cell 232 contains at least one stimulating VCSEL 211, at least one illuminating VCSEL 221, and a plurality of detectors 222 such that the plurality of detectors 222 are arranged circumferentially around the illuminating VCSEL 221, thereby improving the ability of the detectors 222 to receive light reflected from the animal tissue at a plurality of angles. In some embodiments, each stimulating VCSEL 211 and each illuminating VCSEL 221 in each cell 232 is able to be uniquely activated. In some embodiments, the stimulating VCSELs 211 emit light pulses 216 having a wavelength in the range of from about 1.8 microns to about 2.0 microns. In some other embodiments, the wavelength of the light pulses 216 are about 1870 nm. In yet some other embodiments, the wavelength of the light pulses 216 are in the range of from about 1.5 microns to 1.6 microns. In some embodiments, the illuminating VCSELs 221 emit light pulses 226 having a wavelength in the range of from about 650 nm to about 850 nm. In some other embodiments, light pulses 226 with a wavelength of about 830 nm are used to improve signal-to-noise (s/n); however other embodiments use illuminating light pulses 226 with one or more different wavelengths in the range of 800 nm to 850 nm.

FIG. 3A is a block diagram of system 301 that uses an integrated VCSEL/detector array for light stimulation of neural tissue, selective illumination of neural tissue and detection of activity within the neural tissue. In some embodiments, system 301 provides an integrated VCSEL/detector array 331, as described above in system 104 and systems 201 and 202, capable of emitting light pulses 316 for stimulation of neural tissue (e.g. nerve fascicle 97 in nerve bundle 98), light pulses 326 for selective illumination of neural tissue 97 and detecting light reflected 323 from the neural tissue 97. In some embodiments, lens 341 is used to collimate or focus the stimulating light pulses 316 and the illuminating light pulses 326. In some embodiments, laser controller 312 controls the pulse shape and power for the stimulating light pulses 316 and the illuminating light pulses 326 based on input from the control circuitry 313. In some embodiments, signal processor 324 receives an output signal 327 containing the information collected by the detectors in VCSEL/detector array 331 and processes the signal 327 to detect the presence of activity in the illuminated neural tissue 97 (e.g., in some embodiments, the processed signal 327 can detect the presence of nerve activity such as a nerve action potential (NAP) or nerve impulse in a nerve fascicle to determine if a signal has been sent from the brain through the nerve fascicle, or the processed signal 327 can detect a change in various biological parameters (e.g., the water content of animal tissue) to determine a biological response to certain stimulation either external or internal, or the like) and provides input to control circuitry 313.

FIG. 3B is a block diagram of system 302 that uses multiple VCSEL arrays for light stimulation of neural tissue, selective illumination of neural tissue and a detector array for detection of activity within the neural tissue. In some embodiments, system 302 performs in a manner similar to system 301 as described above, however, in contrast to system 301, system 302 provides a separate stimulating VCSEL array 311 for light stimulation of neural tissue 97, a separate illuminating VCSEL array 321 for selective illumination of neural tissue 97 and a separate detector 322 for detection of activity within the neural tissue 97.

Figure 4B:
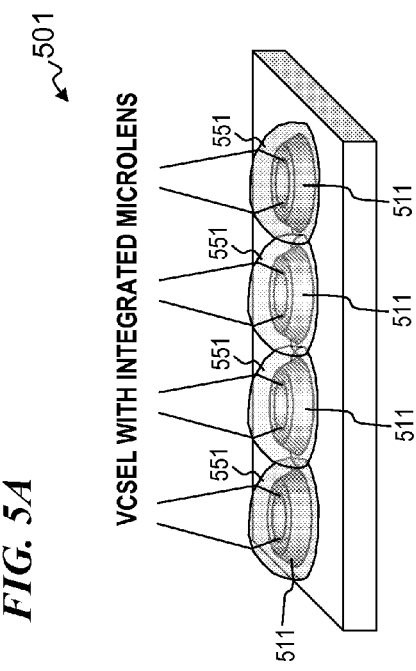
FIG. 4B is a block diagram of system 402 showing an arrangement of VCSELs in a VCSEL flex-cuff capable of targeting individual regions within a nerve (e.g., nerve fascicles).

FIG. 4A is a block diagram of system 401 that uses VCSEL flex-cuffs for light stimulation of a severed nerve 96, selective illumination of the severed nerve and detection of activity within the severed nerve 96. In some embodiments, system 401 provides a severed nerve bundle including a portion of the severed nerve bundle, the brain-side nerve bundle 96, located on the brain side of the nerve break 94 (i.e., brain-side nerve bundle 96 is "upstream" from the nerve break 94 and is physically connected by nerve tissue to the central nervous system and is therefore connected to the brain and can receive input directly from the brain and can provide sensory feedback information directly to the brain) and a portion of the severed nerve bundle, the detached nerve bundle 95 located on the extremity side or organ side of the nerve break 94 (i.e., the detached nerve bundle 94 is "downstream" from the nerve break 94 and is therefore not physically connected to the central nervous system, including the brain and therefore the detached nerve bundle 95 is not able to directly receive input signals from the brain and sensory signals sent from the detached nerve bundle are not able to reach the brain). In some embodiments, system 401 provides a plurality of VCSEL flex-cuffs 441 and 441' that are configured to surround the two portions of the severed nerve bundle and provide light stimulation of specific regions of the nerve bundle, selective illumination of the nerve bundle and detection of activity within the nerve bundle. In some embodiments, a VCSEL flex-cuff 441 includes a plurality of stimulating VCSELs 411 configured to output light capable of stimulating nerve tissue (e.g., generating a nerve action response in a nerve fascicle), a plurality of illuminating VCSELs 421 configured to output light capable of selectively illuminating nerve tissue, and a plurality of detectors 422 configured to receive the light reflected from the nerve tissue and to provide a reflected light signal to a signal processor that processes the provided signal information to detect the presence of activity in the illuminated nerve tissue (e.g., in some embodiments, the detector 422 can detect a nerve activity such as a nerve action potential (NAP) or nerve impulse to determine if a signal has been sent from the brain, or the sensor array can detect a change in various biological parameters (e.g., the water content of animal tissue) to determine a biological response to certain stimulation either external or internal, or the like). In some embodiments, the VCSELs (e.g., stimulating VCSELs 411 and illuminating VCSELs 421) and detectors 422 and associated electronics and wiring in the VCSEL flex-cuff 441 are provided on flexible substrate material (e.g., flexible polycarbonate or gluco-corticosteroid treated Teflon or the like) that is biologically compatible with being implanted into a human or animal body and is capable of being fastened around a nerve bundle (e.g., the brain-side nerve bundle 96 or the detached nerve bundle 95 or the like) such that selected nerve tissue within the nerve bundles (e.g., nerve fascicles) can be targeted by light stimulation or light illumination. In some embodiments, the VCSEL flex-cuff 441 is configured and the VCSELs (e.g., stimulating VCSELs 411 and illuminating VCSELs 421) and detectors 422 are arranged on the VCSEL flex-cuff 441 such that individual nerve fascicles within the nerve bundles (e.g., the brain-side nerve bundle 96 or the detached nerve bundle 95 or the like) can be stimulated with light pulses to generate a nerve response (e.g., a nerve action response (NAP)) or can be selectively illuminated with light pulses such that detectors 422 can detect the light reflected by the individual nerve fascicle to determine the presence of nerve activity in the nerve fascicle. In some embodiments, the VCSEL flex-cuff 441 resembles a four-sided box that surrounds the nerve bundle and is capable of targeting individual regions of nerve tissue (e.g., individual nerve fascicles) as is described in detail below in the description for FIG. 4B.

In some embodiments, system 401 is capable of "bridging" the gap (i.e., the nerve break 94) between the brain-side nerve bundle 96 and the detached nerve bundle 95 to enable communication to take place between the brain and the detached nerve bundle 95. When a nerve is severed, the nerve is no longer able to pass the nerve action or nerve pulse provided by the brain to control extremities or organs and the nerve is no longer able to support sensory communication from the extremities to provide feedback or sensory information to the brain. In some embodiments, system 401 is configured to act as a communication bridge across the nerve break. In some embodiments, a nerve action signal 455 is sent down a nerve fascicle by the brain to an extremity (e.g., the brain sends a nerve action signal to a nerve in a finger to contract a finger muscle, thereby causing the finger to close) but the nerve action signal 455 is unable to reach the extremity due to a nerve break 94 (e.g., located between the brain and the finger) that prevents the nerve action signal from reaching the extremity. In some embodiments, a VCSEL flex-cuff 441 surrounds the brain-side nerve bundle 96 and one of the plurality of illuminating VCSELs 421 selectively illuminates the nerve fascicle passing the nerve action signal 455 and one of the plurality of detectors 422 detects the light reflected from the illuminated nerve fascicle and provides a reflected-light signal to a nerve action detector 453. In some embodiments, the nerve action detector 453 determines if the illuminated fascicle was activated by nerve activity and if nerve activity is detected, the nerve action detector 453 sends a nerve action request 443 to a nerve action stimulator 454 connected to VCSEL flex-cuff 441' that surrounds the detached nerve bundle 95. The nerve action request 443 provide information regarding which nerve fascicle in the brain-side nerve bundle 96 was activated by the brain and which nerve fascicle in the detached nerve bundle should be stimulated. In some embodiments, the nerve action stimulator 454 receives the nerve action request 443 and sends a drive signal (e.g., a VCSEL control signal to control the pulse shape and power of the stimulating VCSEL) to the appropriate stimulating VCSEL 411' in order to generate an artificial nerve action signal 457 in the associated nerve fascicle and in effect passing the nerve action signal 455 sent by the brain (e.g., causing the finger muscle to contract thereby closing the finger).

In some embodiments, system 401 provides a process that is the reverse of the process described in the preceding paragraph, that is, a nerve action signal 458 traveling from an extremity (e.g., sensory information regarding touch, pressure, sound, light, or the like) that is unable to be sent to the brain for processing and feedback due to a nerve break 94 can be "forwarded" across the nerve break 94 and sent to the brain for processing and feedback. In some embodiments, one of the plurality of illuminating VCSELs 421' selectively illuminates the nerve fascicle transmitting the nerve action signal 458 in the detached nerve bundle and one of the plurality of detectors 422' detects the light reflected from the illuminated nerve fascicle and provides a reflected-light signal to a nerve action detector 452. In some embodiments, the nerve action detector 452 determines (at input signal 445) if the illuminated fascicle was activated by nerve activity and if nerve activity is detected, the nerve action detector 452 sends a nerve action request 446 to a nerve action stimulator 451 connected to VCSEL flex-cuff 441 that surrounds the detached nerve bundle 96. The nerve action request 446 provides information regarding which nerve fascicle in the detached nerve bundle 95 was activated by the sensory action and which nerve fascicle in the brain-side nerve bundle 96 should be stimulated. In some embodiments, the nerve action stimulator 451 receives the nerve action request 446 and sends a drive signal 447 (e.g., a VCSEL control signal to control the pulse shape and power of the stimulating VCSEL) to the appropriate stimulating VCSEL 411 in order to generate an artificial nerve action signal 456 in the associated nerve fascicle and in effect passing the nerve action signal 458 sent by the sensory action to the brain for processing and/or feedback.

In some embodiments, the VCSEL flex-cuff 441 can be reprogrammed if and when the VCSEL flex-cuff 441 shifts from its optimal position. In some embodiments, the reprogramming remaps which VCSEL devices are activated to emit light to stimulate, illuminate or detect a particular location. For example, the VCSEL flex-cuff might shift as a whole relative to the nerve fascicles it is intended to stimulate, illuminate and detect by some amount or the nerve fascicles themselves may shift with respect to the VCSEL flex-cuff. In these circumstances, the individual VCSELs would be remapped such that the desired nerve fascicles are being correctly stimulated, illuminated and detected.

FIG. 4B is a block diagram of system 402 showing an arrangement of stimulating VCSELs in a VCSEL flex-cuff capable of targeting individual regions within a nerve (e.g., nerve fascicles). In some embodiments, system 402 includes a plurality of stimulating VCSELs 411 arranged around the perimeter of a cube-shaped VCSEL flex-cuff as described above for system 401. In some embodiments, the stimulating VCSELs 411 are configured to operate in a manner similar to a "gamma knife" such that only the areas in the nerve bundle (e.g., nerve fascicles) in which two stimulating VCSEL light pulses intersect will be stimulated to such a degree as to generate a nerve action (e.g., a nerve action potential). In some embodiments, the pulse shape and pulse power of each stimulating light pulse from each individual stimulating VCSEL provides a subcritical light confluence and is not capable by itself alone of generating a nerve activity in a nerve fascicle. Therefore it is only at nerve locations or in nerve fascicles where two or more stimulating light pulses intersect that a supercritical light confluence is achieved and a nerve activity is generated in the nerve fascicle. As shown in FIG. 4B, along the x-axis, only stimulating VCSEL 411', located at position 2 on the x-axis, is "on" and along the y-axis, only stimulating VCSEL 411", located at position 3 on the y-axis is on. Therefore, the only area in nerve bundle 98 where a nerve activity is capable of being generated due to supercritical light confluence is at the intersection of the light pulses from VCSEL 411' and VCSEL 411" (i.e., the point (x,y)=(2, 3)). All other locations in nerve bundle 98 experience subcritical light confluence not capable of generating a nerve activity.

Figure 5A:
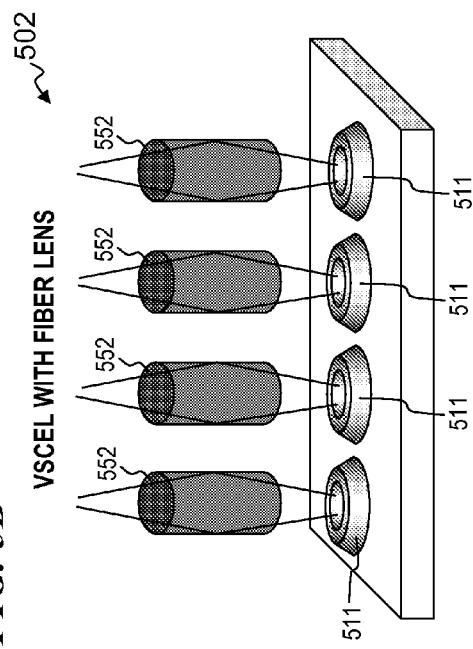
FIG. 5A is a diagram of system 501 showing a one-dimensional VCSEL array with integrated microlenses.

FIG. 5A is a diagram of system 501 showing a one-dimensional VCSEL array with integrated microlenses 551. In some embodiments, each VCSEL 511 is integrated with a microlens 551 (e.g., the integrated lenses can be provided by a planar sheet of silica glass with holograms in it, an array of graded index (GRIN) lenses, or lenses made by directly depositing a material onto the VCSELs (e.g., an epoxy).

Figure 5B:
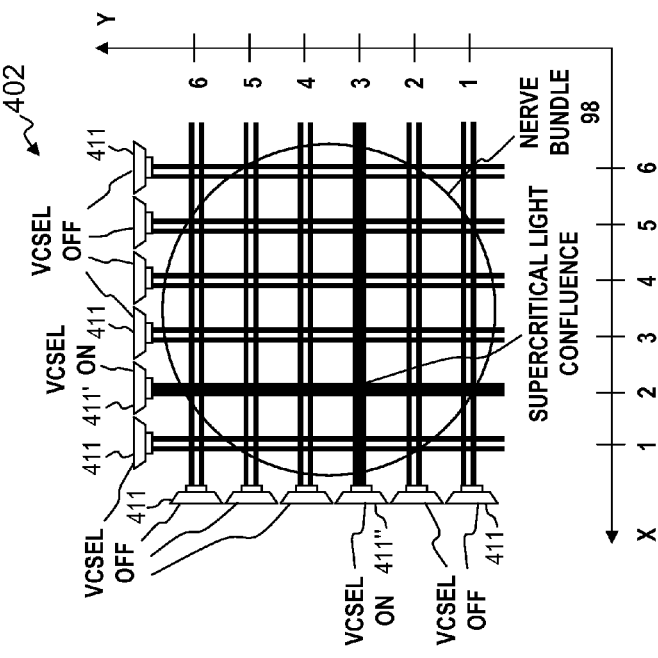
FIG. 5B is a diagram of system 502 showing a one-dimensional VCSEL array with focusing fiber lenses.

FIG. 5B is a diagram of system 502 showing a one-dimensional VCSEL array with focusing optical fiber lenses 552. In some embodiments, each VCSEL 511 is integrated with and aligned to a gradient index rod lens 552. The rod lens of gradient index type has a characteristic in which the refraction index changes gradually in the direction of the radius from the axis thereof, so that incoming light may be converted into collimated lights or converged and launched by defining the length of the lens or the distance between the lens and the optical fiber according to the wavelength. In other embodiments, each VCSEL 511 in the one-dimensional VCSEL array is integrated with and aligned to an optical fiber and the array of optical fibers corresponding to the VCSEL array is positioned to match a physical structure (e.g., the cochlea nerve or individual nerve fascicles or the like) of the tissue to be stimulated or illuminated. In some other embodiments, the distal ends of the integrated optical fibers are lenses to provide collimated or focused light.

FIG. 6A is a diagram of system 601 showing a two-dimensional VCSEL array 662 used for externally targeting the cochlear nerve of the cochlea 88 within the inner ear as part of the right osseous labyrinth 89. In some embodiments, the two-dimensional VCSEL array 662 is configured to output light pulses capable of stimulating nerve tissue (e.g., generating a nerve action potential (NAP) in cochlear nerve tissue) based on an external stimulus (e.g., sound, pitch, frequency, amplitude, or the like). In some embodiments, the two-dimensional VCSEL array 662 is surgically implanted next to the cochlea 88 and each individual VCSEL 611 is mapped to a specific location on the cochlea 88 to target a specific region or portion of the cochlear nerve, each region or portion of the cochlear nerve corresponding to a particular frequency in the audible frequency spectrum. In some embodiments, a benefit of using a two-dimensional VCSEL array 662 for externally targeting the cochlear nerve is that if the implanted VCSEL array 662 is shifted with respect to the cochlear nerve after the individual VCSELs have been mapped to the particular frequencies in the audible frequency spectrum, the VCSEL array can be remapped without the need for additional surgical procedures.

FIG. 6B is a diagram of system 602 showing a VCSEL flex-circuit array 661 capable of being inserted internally into the cochlea 88 within the inner ear to stimulate the cochlear nerve. In some embodiments, VCSEL flex-circuit array 661 includes a plurality of stimulating VCSELs 611 each configured to output light pulses capable of stimulating nerve tissue (e.g., generating a nerve action potential (NAP) in cochlear nerve tissue) based on an external stimulus (e.g., sound, pitch, frequency, amplitude, or the like). In some embodiments, the VCSEL flex-circuit array 661 is surgically inserted internally into the cochlea 88 and each individual stimulating VCSEL 611 is mapped to a specific location in the cochlea 88 to target a specific region or portion of the cochlear nerve, each region or portion of the cochlear nerve corresponding to a particular frequency in the audible frequency spectrum.

FIG. 6C is a diagram of system 603 showing a VCSEL flex-circuit array 663 capable of being surgically implanted next to the cochlea 88 or attached directly to the exterior of the cochlea 88 within the inner ear to stimulate the cochlear nerve. In some embodiments, VCSEL flex-circuit array 663 includes a plurality of stimulating VCSELs 611 each configured to output light pulses capable of stimulating nerve tissue (e.g., generating a nerve action potential (NAP) in cochlear nerve tissue) based on an external stimulus (e.g., sound pitch, frequency, amplitude, or the like). In some embodiments, the VCSEL flex-circuit array 663 is surgically implanted next to the cochlea or attached to the cochlea 88 and each individual stimulating VCSEL 611 is mapped to a specific location in the cochlea 88 to target a specific region or portion of the cochlear nerve, each region or portion of the cochlear nerve corresponding to a particular frequency in the audible frequency spectrum.

Figure 7:
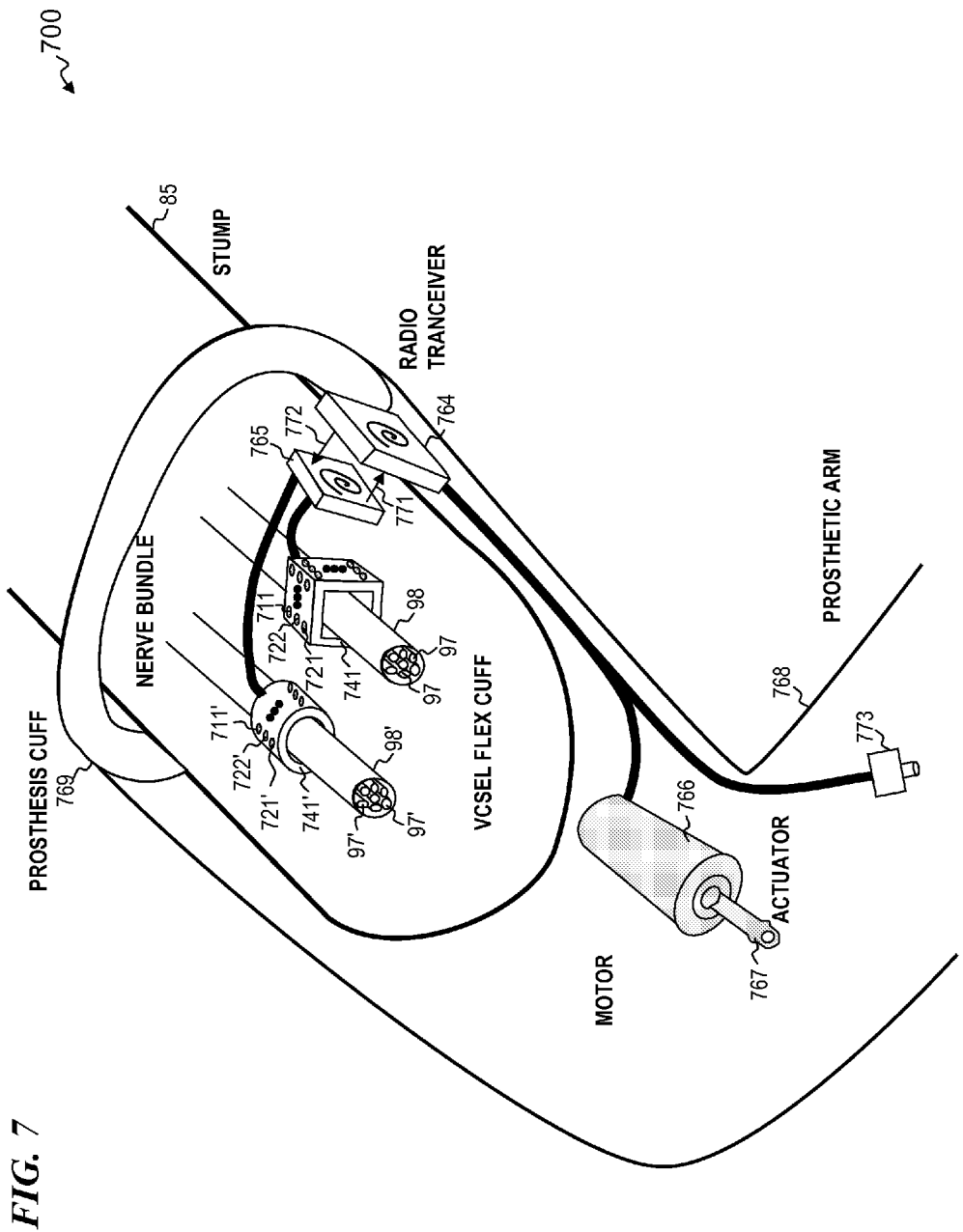
FIG. 7 is a block diagram of prosthetic system 700 that uses VCSEL flex-cuffs for light stimulation of nerves, selective illumination of the nerves and detection of activity within the nerves to activate the prosthesis and provide feedback from the prosthesis to the nerves.

FIG. 7 is a block diagram of prosthetic system 700 that uses VCSEL flex-cuffs 741 and 741' for light stimulation of nerves, selective illumination of the nerves and detection of activity within the nerves to activate the prosthesis and provide feedback from the prosthesis to the nerves. In some embodiments, system 700 includes a prosthetic arm 768 attached by a prosthetic cuff 769 to an arm stump 85. In some embodiments, implanted within the arm stump 85 is a plurality of VCSEL flex-cuffs 741 electrically connected to transceiver/controller/battery 765, each VCSEL flex-cuff 741 configured to surround a nerve bundle. For example, VCSEL flex-cuffs 741 and 741' respectively surround nerve bundles 98 and 98' and provide light stimulation of specific regions of the nerve bundles 98 and 98', selective illumination of the nerve bundles 98 and 98' and detection of activity within the nerve bundles 98 and 98'. In some embodiments, the VCSEL flex-cuffs 741 and 741' include a plurality of stimulating VCSELs 711 configured to output light capable of stimulating nerve tissue (e.g., generating a nerve action response in a nerve fascicle), a plurality of illuminating VCSELs 721 configured to output light capable of selectively illuminating nerve tissue, and a plurality of detectors 722 configured to receive the light reflected from the nerve tissue and to provide a reflected light signal to a signal processor located in the transceiver/controller/battery 765 that processes the provided signal information to detect the presence of activity in the illuminated nerve tissue (e.g., in some embodiments, the detector 722 can detect a nerve activity such as a nerve action potential (NAP) or nerve impulse to determine if a signal has been sent from the brain, or the sensor array can detect a change in various biological parameters (e.g., the water content of animal tissue) to determine a biological response to certain stimulation either external or internal, or the like). In some embodiments, the VCSELs (e.g., stimulating VCSELs 711 and illuminating VCSELs 721) and detectors 722 and associated electronics and wiring in the VCSEL flex-cuffs 741 and 741' are provided on flexible substrate material (e.g., flexible polycarbonate or gluco-corticosteroid treated Teflon or the like) that is biologically compatible with being implanted into a human or animal body and is capable of being fastened around a nerve bundle 98 and 98' such that selected nerve tissue within the nerve bundles (e.g., nerve fascicles 97 and 97') can be targeted by light stimulation or light illumination. In some embodiments, the VCSEL flex-cuffs 741 and 741' are configured and the VCSELs (e.g., stimulating VCSELs 711 and illuminating VCSELs 721) and detectors 722 are arranged on the VCSEL flex-cuffs 741 and 741' such that individual nerve fascicles within the nerve bundles can be stimulated with light pulses to generate a nerve response (e.g., a nerve action response (NAP)) or can be selectively illuminated with light pulses such that detectors 722 can detect the light reflected by the individual nerve fascicle to determine the presence of nerve activity in the nerve fascicle. In some embodiments, the VCSEL flex-cuff 741 resembles a four-sided box that surrounds the nerve bundle and is capable of targeting individual regions of nerve tissue (e.g., individual nerve fascicles) as is described in detail above in the description for FIG. 4B. In some embodiments, the VCSEL flex-cuff 741' resembles a cylinder that surrounds the nerve bundle.

In some embodiments, system 700 is capable of communicating nerve action signals (e.g., a nerve action potential) from the brain to the prosthetic arm 768 in order to control the movement of the prosthetic arm 768. In some embodiments, the brain sends a nerve action signal down a particular nerve fascicle 97 of nerve bundle 98 (e.g., the brain sends a nerve action signal down a nerve fascicle that corresponded to a nerve in a finger prior to the amputation of that portion of the arm in order to contract a finger muscle, which would have caused the finger to close), the nerve action signal is detected by VCSEL flex-cuff 741 and the transceiver/controller/battery 765 wirelessly transmits an actuation signal 771 to the prosthetic transceiver/controller/charger 764 which then determines the appropriate action based on which nerve fascicle 97 was activated (e.g., if the nerve fascicle corresponding to a finger muscle was activated to cause a finger to close, the prosthetic transceiver/controller/charger 764 will determine which motor(s) 766 in the prosthetic arm 768 to activate in order to cause the appropriate actuator(s) 767 to close the corresponding finger on the prosthetic arm 768. In some embodiments, the transceiver/controller/battery 765 has a rechargeable battery pack (e.g., one or more batteries) that can be inductively recharged transcutaneously and a recharging transceiver/controller/charger 764 capable of electromagnetic coupling using inductive and propagation techniques.

In some embodiments, system 700 is capable of communicating sensory signals (e.g., touch, pressure, feel, or the like) from sensor(s) 773 in the prosthetic arm 768 in order to provide sensory information or feedback to the brain. In some embodiments, the sensor 773 sends a sensory signal to the transceiver/controller/charger 764 and the transceiver/controller/charger 764 determines the appropriate nerve fascicle 97 to receive the sensory signal based on the location of the sensor 773 in the prosthetic arm (e.g., if a pressure sensor is located in the index finger of the prosthesis, the transceiver/controller/charger 764 will direct the sensory signal to the nerve fascicle that corresponds to the index finger) and transmit the sensory signal to the transceiver/controller/battery 765. In some embodiments, the transceiver/controller/battery 765 directs the sensory signal to the appropriate nerve fascicle 97 by providing a control signal to the appropriate stimulating VCSEL 711 in the VCSEL flex-cuff 741 which generates a stimulating light pulse and causes the generation of a nerve action in the nerve fascicle 97 and the nerve action travels to the brain to provide the sensory information or feedback of prosthetic operation.

FIG. 8A is a block diagram of system 801 using implantable optical fibers capable of light stimulation of animal tissue, selective illumination of animal tissue and detection of activity within the animal tissue. In some embodiments, system 801 provides an apparatus configured to provide light stimulation of human tissue or animal tissue, selective illumination of human or animal tissue and detection of activity within the selectively illuminated human or animal tissue, including a stimulating VCSEL array 811 configured to output light pulses (in some embodiments, the light pulses have a wavelength in the range of about 1800 nm to about 2000 nm) capable of stimulating human tissue (e.g., a human nerve 98), a plurality of implantable optical fibers 891 implanted into human nerve 98 and each of the plurality of implantable optical fibers 891 optically coupled to a separate VCSEL in the stimulating VCSEL array 811 and configured to direct the stimulating light pulses generated by the individual VCSELs of the stimulating VCSEL array to individual and unique areas within the human nerve 98 (e.g., individual nerve fascicles within the human nerve 98) such that the individual nerve fascicles are capable of being optically stimulated, thus generating a nerve activity (e.g., a nerve action potential) within the nerve fascicle.

In some embodiments, system 801 further includes a physiological nerve activity detector 820A configured to detect the presence of nerve activity (e.g., a nerve action potential) in human tissue (e.g., human nerve 98) and includes an illumination VCSEL array 821 and an optical detector array 822. The illumination VCSEL array 821 configured to output light pulses capable of selectively illuminating human tissue, a plurality of implantable optical fibers 891 implanted into human nerve 98 and each of the plurality of implantable optical fibers 891 optically coupled to a separate VCSEL in the illuminating VCSEL array 821 and configured to direct the illuminating light pulses generated by the individual VCSELs of the illuminating VCSEL array to individual and unique areas within the human nerve 98 (e.g., individual nerve fascicles within the human nerve 98) such that the individual nerve fascicles are capable of being optically illuminated within the nerve fascicle. In some embodiments, a plurality of implantable optical fibers implanted in the human nerve 98 and optically coupled to the detector array 822 and configured to direct the light reflected by the individual illuminated nerve fascicles within the human nerve to individual detectors in the optical detector array 822. In some embodiments, the optical detector array 822 is configured to detect light reflected from the individual illuminated fascicles within the human nerve 98 and further configured to output a neural activity signal 827 to a computer 896 that includes a set of machine control instructions (programmable control code to interpret the neural activity signal 827 to determine if a nerve activity has occurred in a plurality of individual nerve fascicles in the human nerve 98, and otherwise adjust, time, or otherwise control pulse shape, timing, intensity, and the like) is stored on computer-readable medium 897 (for example, a compact FLASH memory fob, diskette, CDROM, or network connection (e.g., the internet)), which is connectable to control one or more operations or functions of stimulating VCSEL array.

Figure 8B:
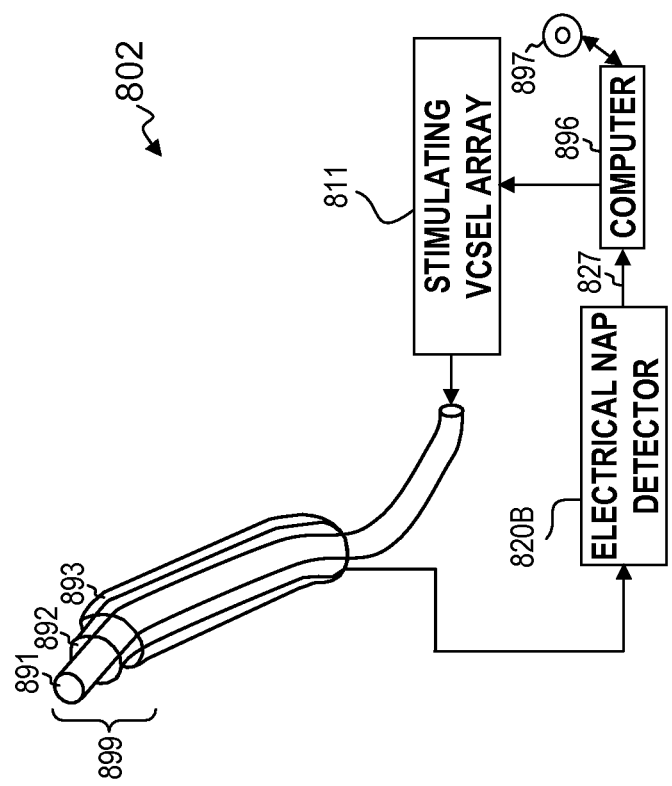
FIG. 8B is a block diagram of integrated implantable system 802 that uses conductive-coated implantable optical fibers capable of light stimulation of animal tissue, and electrical detection of activity within the animal tissue.

FIG. 8B is a block diagram of integrated implantable system 802 that uses conductive-coated implantable optical fibers capable of light stimulation of animal tissue, and electrical detection of activity within the animal tissue. In some embodiments, system 802 combines the stimulating light pulses output by the stimulating VCSEL array 811 and the physiological nerve activity detector 820B into a single conductively coated implantable optical fiber 899, thereby significantly reducing the number of implantable optical fibers required for directing the stimulating light pulses and detecting nerve activity within individual nerve fascicles. In some embodiments, conductively coated implantable optical fiber 899 is implanted in human nerve tissue and includes a central optical fiber 891 configured to transmit stimulating light pulses output by the stimulating VCSEL array 811 to individual regions or areas within a human nerve or other human tissue (e.g., nerve fascicles within a nerve bundle), a conductive coating 892 (e.g., gold, platinum, titanium, or the like) surrounding the central optical fiber 891 and configured to detect the electrical activity of individual nerve fascicles within the human nerve tissue, transmitting the electrical activity to an electrical nerve activity detector 820B and outputting a neural activity signal 897 from the electrical nerve activity detector 820B to a computer 896 that includes a set of machine control instructions (programmable control code to interpret the neural activity signal 827 to determine if a nerve activity has occurred in a plurality of individual nerve fascicles in the human nerve 98, and otherwise adjust, time, or otherwise control pulse shape, timing, intensity, and the like) is stored on computer-readable medium 897 (for example, a compact FLASH memory fob, diskette, CDROM, or network connection (e.g., the internet)), which is connectable to control one or more operations or functions of stimulating VCSEL array. In some embodiments, the conductive coating 892 of the conductively coated implantable optical fiber 899 is covered by a protective exterior coating 893 to protect the conductive coating 892.

Figure 9B:
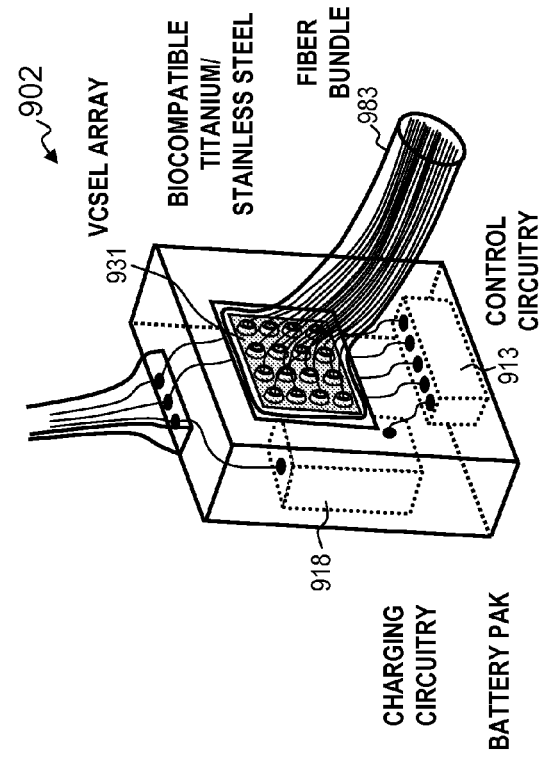
FIG. 9B is a diagram of implantable system 902 using a VCSEL array capable of light stimulation of animal tissue, selective illumination of animal tissue and detection of activity within the animal tissue enclosed within a biocompatible housing and integrated with a delivery fiber bundle.
Figure 9A:
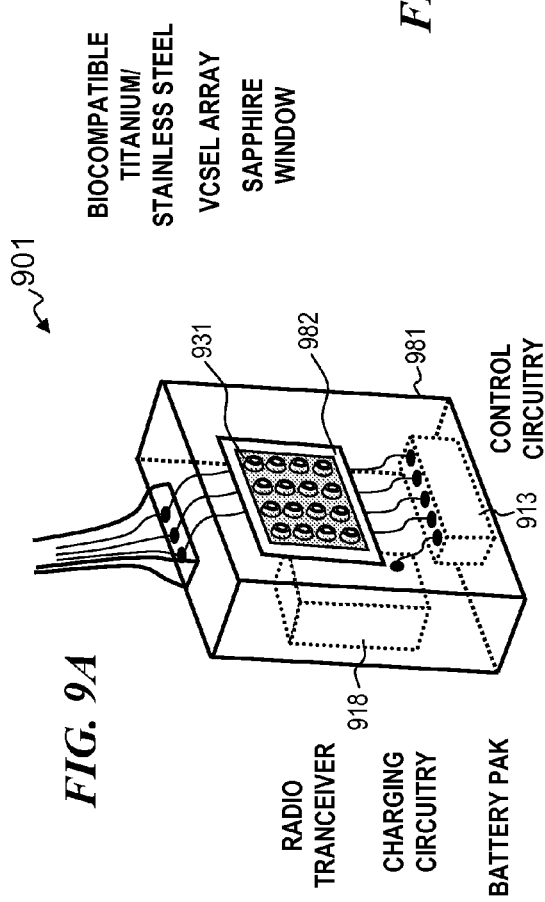
FIG. 9A is a diagram of implantable system 901 using a VCSEL array capable of light stimulation of animal tissue, selective illumination of animal tissue and detection of activity within the animal tissue enclosed within a biocompatible housing.

FIG. 9A is a diagram of implantable system 901 using a VCSEL array capable of light stimulation of animal tissue, selective illumination of animal tissue and detection of activity within the animal tissue enclosed within a biocompatible housing. In some embodiments, system 901 includes a VCSEL array 931 configured to provide light stimulation of neural tissue, selective illumination of neural tissue and detection of activity within the neural tissue and operates in a manner similar to systems previously described above. In some embodiments, the VCSEL array 931 is controlled by control circuitry 913 and external signal data and power is received transcutaneously with the transceiver/circuitry/battery 918. In some embodiments, the VCSEL array 931, the control circuitry 913 and the transceiver/circuitry/battery 918 are housed in a biocompatible housing 981 capable of being surgically implanted into a human or animal with a reduced risk of negative reactions or rejection of the implanted device (e.g., in some embodiments, the housing is a polycarbonate material or titanium or the like) and the light pulses pass through a window 982 (e.g., a sapphire window) in the biocompatible housing 981 for direct projection of the stimulating or illuminating pulse on nearby neural tissue.

FIG. 9B is a diagram of implantable system 902 using a VCSEL array 931 capable of light stimulation of animal tissue, selective illumination of animal tissue and detection of activity within the animal tissue enclosed within a biocompatible housing 981 and integrated with a delivery fiber bundle 983. In some embodiments, system 902 includes a VCSEL array 931 configured to provide light stimulation of neural tissue, selective illumination of neural tissue and detection of activity within the neural tissue and operates in a manner similar to systems previously described above. In some embodiments, the VCSEL array 931 is controlled by control circuitry 913 and external signal data and power is received transcutaneously with the transceiver/circuitry/battery 918. In some embodiments, the VCSEL array 931, the control circuitry 913 and the transceiver/circuitry/battery 918 are housed in a biocompatible housing 981 capable of being surgically implanted into a human or animal with a reduced risk of negative reactions or rejection of the implanted device (e.g., in some embodiments, the housing is a polycarbonate material or titanium or the like) and the light pulses are directed to particular regions or areas of neural tissue via a plurality of optical fibers contained within fiber bundle 983 to provide stimulation or illumination of the neural tissue. In some embodiments, an optical fiber bundle is used for directing the stimulating or illuminating light to regions that are not located near by the implanted housing. In some embodiments, a higher level of compatibility of the fiber with human tissue is achieved if the fiber is coated (or the area of insertion is treated) with gluco-corticosteroids.

Figure 10A:
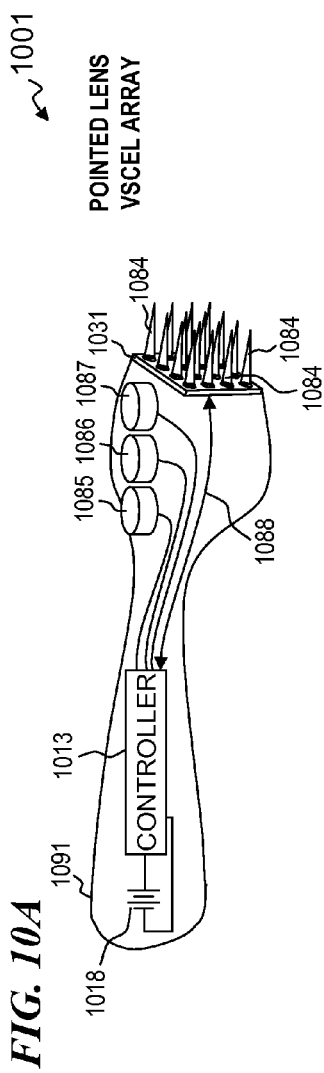
FIG. 10A is a diagram of hand-held system 1001 using a VCSEL array capable of light stimulation of animal tissue, selective illumination of animal tissue and detection of activity within the animal tissue.

FIG. 10A is a diagram of hand-held system 1001 using a VCSEL array capable of light stimulation of animal tissue, selective illumination of animal tissue and detection of activity within the animal tissue. In some embodiments, hand-held system 1001 is at least mostly embedded in a self-contained hand-held form factor 1091 (e.g., such as a light pen, pointer and/or wand) that can be manually used to control, direct and/or shutter light generated by VCSEL array 1031. In some embodiments, the hand-held device 1001 of the present invention includes one or more internal power sources 1018, such as battery cells, to provide self-contained electrical power to the VCSEL array and/or other internal components, such as a controller 1013 used to control the VCSEL array.

In some embodiments, the present invention includes an apparatus having a finger-and/or-thumb control (e.g., control buttons 1085, 1086, and 1087) that controls the operation of the VCSEL array 1031, optics to focus and deliver the light to a nerve (e.g., an array of pointed lenses 1084 integrated with the VCSEL array 1031 capable of tightly focusing the light pulses generated by the VCSEL array 1031 to a point), a self-contained-energy-storage-powered (e.g., battery-powered 1018) VCSEL array capable of generating light pulses with a wavelength and power capable of efficaciously stimulating or selectively illuminating a nerve and detecting light reflected by the illuminated nerve, and a controller operable to drive the VCSEL array 1031 based on input from the finger/thumb control buttons 1085, 1086 and 1087. In some embodiments, this apparatus is used to deliver an efficacious amount of visible and infrared (IR) light so as to selectively illuminate and stimulate nerve tissue and to detect the light reflected by the illuminated nerve to determine if a nerve activity has been generated by the stimulating light pulse. In some embodiments, a visible laser beam is used to point to and illuminate the area to be stimulated and an IR laser beam is used to stimulate a nerve at that illuminated area. In some embodiments, control button 1085 is used to control the stimulating VCSELs, control button 1086 is used to control the illuminating VCSELs and control button 1087 is used to control the detectors integrated on VCSEL array 1031. In some embodiments, VCSEL array 1031 includes stimulating VCSELs configured to output light pulses capable of stimulating nerve tissue and generating a nerve action in the stimulated nerve. In some embodiments, VCSEL array 1031 further includes illuminating VCSELs configured to output light pulses capable of selectively illuminating nerve tissue and detectors configured to detect the light reflected by the illuminated nerve tissue. In some embodiments, control buttons 1085, 1086 and 1087 are electrically connected to controller 1013 and controller 1013 provides the VCSEL array 1031 with directions on which VCSELs in the VCSEL array to activate. In some embodiments, electrical connection 1088 passes a control signal from the controller 1013 to the VCSEL array and a feedback signal from the detectors in the VCSEL array 1031 to the controller.

In some embodiments, at least some of the metal portions of the battery 1018 and other internal electrical wiring connections 1088 are all or substantially all made of a non-magnetic electrically conductive material such as copper, in order to be usable near MRI equipment.

Figure 10B:
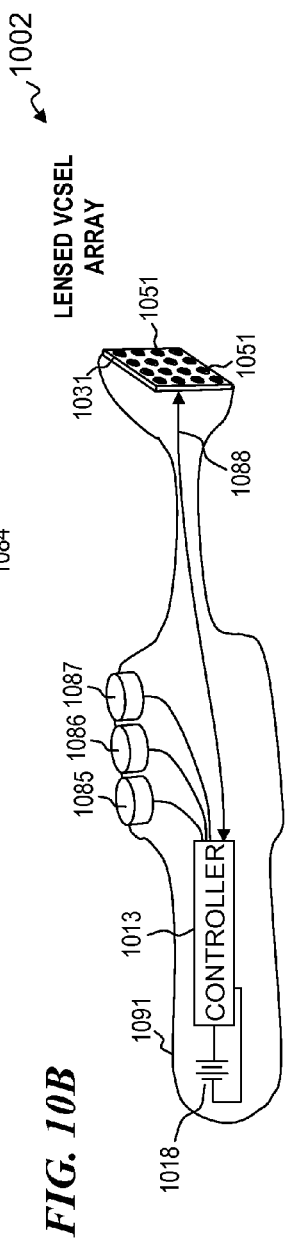
FIG. 10B is a diagram of hand-held system 1002 using a lensed VCSEL array capable of light stimulation of animal tissue, selective illumination of animal tissue and detection of activity within the animal tissue.

FIG. 10B is a diagram of hand-held system 1002 using a lensed VCSEL array capable of light stimulation of animal tissue, selective illumination of animal tissue and detection of activity within the animal tissue. In some embodiments, hand-held system 1002 is at least mostly embedded in a self-contained hand-held form factor 1091 (e.g., such as a light pen, pointer and/or wand) that can be manually used to control, direct and/or shutter light generated by VCSEL array 1031. In some embodiments, the hand-held device 1002 of the present invention includes one or more internal power sources 1018, such as battery cells, to provide self-contained electrical power to the VCSEL array and/or other internal components, such as a controller 1013 used to control the VCSEL array.

In some embodiments, the present invention includes an apparatus having a finger-and/or-thumb control (e.g., control buttons 1085, 1086, and 1087) that controls the operation of the VCSEL array 1031, optics to focus and deliver the light to a nerve (e.g., an array of integrated lenses 1051 with the VCSEL array 1031 capable of focusing or collimating the light pulses generated by the VCSEL array 1031), a self-contained-energy-storage-powered (e.g., battery-powered 1018) VCSEL array capable of generating light pulses with a wavelength and power capable of efficaciously stimulating or selectively illuminating a nerve and detecting light reflected by the illuminated nerve, and a controller operable to drive the VCSEL array 1031 based on input from the finger/thumb control buttons 1085, 1086 and 1087. In some embodiments, each VCSEL and detector in the VCSEL array 1031 is integrated with a microlens 1051 (e.g., the integrated lenses can be provided by a planar sheet of silica glass with holograms in it, an array of graded index (GRIN) lenses, or lenses made by directly depositing a material onto the VCSELs (e.g., an epoxy). In some other embodiments, each VCSEL and detector in the VCSEL array 1031 is integrated with and aligned to a gradient index rod lens. In some embodiments, this apparatus is used to deliver an efficacious amount of visible and infrared (IR) light so as to selectively illuminate and stimulate nerve tissue and to detect the light reflected by the illuminated nerve to determine is a nerve activity has been generated by the stimulating light pulse. In some embodiments, a visible laser beam is used to point to and illuminate the area to be stimulated and an IR laser beam is used to stimulate a nerve at that illuminated area. In some embodiments, control button 1085 is used to control the stimulating VCSELs, control button 1086 is used to control the illuminating VCSELs and control button 1087 is used to control the detectors integrated on VCSEL array 1031. In some embodiments, VCSEL array 1031 includes stimulating VCSELs configured to output light pulses capable of stimulating nerve tissue and generating a nerve action in the stimulated nerve. In some embodiments, VCSEL array 1031 further includes illuminating VCSELs configured to output light pulses capable of selectively illuminating nerve tissue and detectors configured to detect the light reflected by the illuminated nerve tissue. In some embodiments, control buttons 1085, 1086 and 1087 are electrically connected to controller 1013 and controller 1013 provides the VCSEL array 1031 with directions on which VCSELs in the VCSEL array to activate. In some embodiments, electrical connection 1088 passes control signals from the controller 1013 to the VCSEL array and feedback signals from the detectors in the VCSEL array 1031 to the controller.

In some embodiments, at least some of the metal portions of the battery 1018 and other internal electrical wiring connections 1088 are all or substantially all made of a non-magnetic electrically conductive material such as copper, in order to be usable near MRI equipment.

Figure 10C:
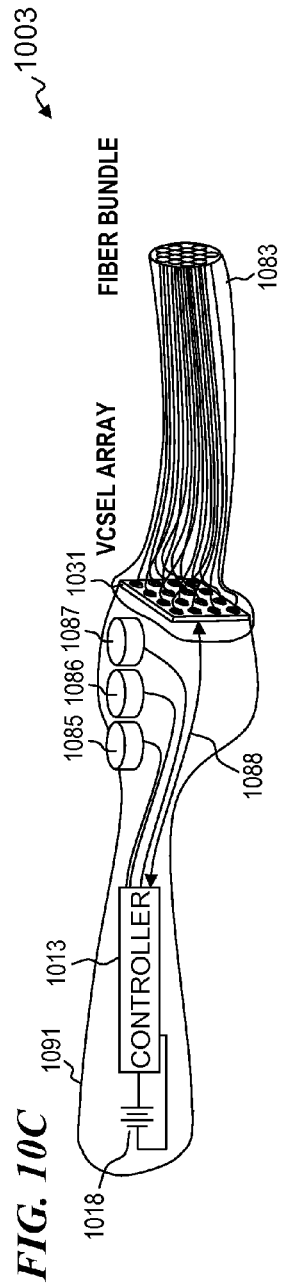
FIG. 10C is a diagram of hand-held system 1003 using a VCSEL array capable of light stimulation of animal tissue, selective illumination of animal tissue and detection of activity within the animal tissue and integrated with a delivery fiber bundle.

FIG. 10C is a diagram of hand-held system 1003 using a VCSEL array capable of light stimulation of animal tissue, selective illumination of animal tissue and detection of activity within the animal tissue and integrated with a delivery fiber bundle. In some embodiments, hand-held system 1003 is at least mostly embedded in a self-contained hand-held form factor 1091 (e.g., such as a light pen, pointer and/or wand) that can be manually used to control, direct and/or shutter light generated by VCSEL array 1031. In some embodiments, the hand-held device 1003 of the present invention includes one or more internal power sources 1018, such as battery cells, to provide self-contained electrical power to the VCSEL array and/or other internal components, such as a controller 1013 used to control the VCSEL array.

In some embodiments, the present invention includes an apparatus having a finger-and/or-thumb control (e.g., control buttons 1085, 1086, and 1087) that controls the operation of the VCSEL array 1031, optics to focus and deliver the light to a nerve (e.g., the VCSEL array 1031 output light pulses and the sensory feedback signal detected by the detectors is carried in an optical fiber 1083, and, either sharing a single optical fiber or passing in one or more separate fibers next to the optical fiber), a self-contained-energy-storage-powered (e.g., battery-powered 1018) VCSEL array capable of generating light pulses with a wavelength and power capable of efficaciously stimulating or selectively illuminating a nerve and detecting light reflected by the illuminated nerve, and a controller operable to drive the VCSEL array 1031 based on input from the finger/thumb control buttons 1085, 1086 and 1087. In some embodiments, this apparatus is used to deliver an efficacious amount of visible and infrared (IR) light so as to selectively illuminate and stimulate nerve tissue and to detect the light reflected by the illuminated nerve to determine is a nerve activity has been generated by the stimulating light pulse. In some embodiments, a visible laser beam is used to point to and illuminate the area to be stimulated and an IR laser beam is used to stimulate a nerve at that illuminated area. In some embodiments, control button 1085 is used to control the stimulating VCSELs, control button 1086 is used to control the illuminating VCSELs and control button 1087 is used to control the detectors integrated on VCSEL array 1031. In some embodiments, VCSEL array 1031 includes stimulating VCSELs configured to output light pulses capable of stimulating nerve tissue and generating a nerve action in the stimulated nerve. In some embodiments, VCSEL array 1031 further includes illuminating VCSELs configured to output light pulses capable of selectively illuminating nerve tissue and detectors configured to detect the light reflected by the illuminated nerve tissue. In some embodiments, control buttons 1085, 1086 and 1087 are electrically connected to controller 1013 and controller 1013 provides the VCSEL array 1031 with directions on which VCSELs in the VCSEL array to activate. In some embodiments, electrical connection 1088 passes control signals from the controller 1013 to the VCSEL array and feedback signals from the detectors in the VCSEL array 1031 to the controller.

In some embodiments, at least some of the metal portions of the battery 1018 and other internal electrical wiring connections 1088 are all or substantially all made of a non-magnetic electrically conductive material such as copper, in order to be usable near MRI equipment.

Figure 11:
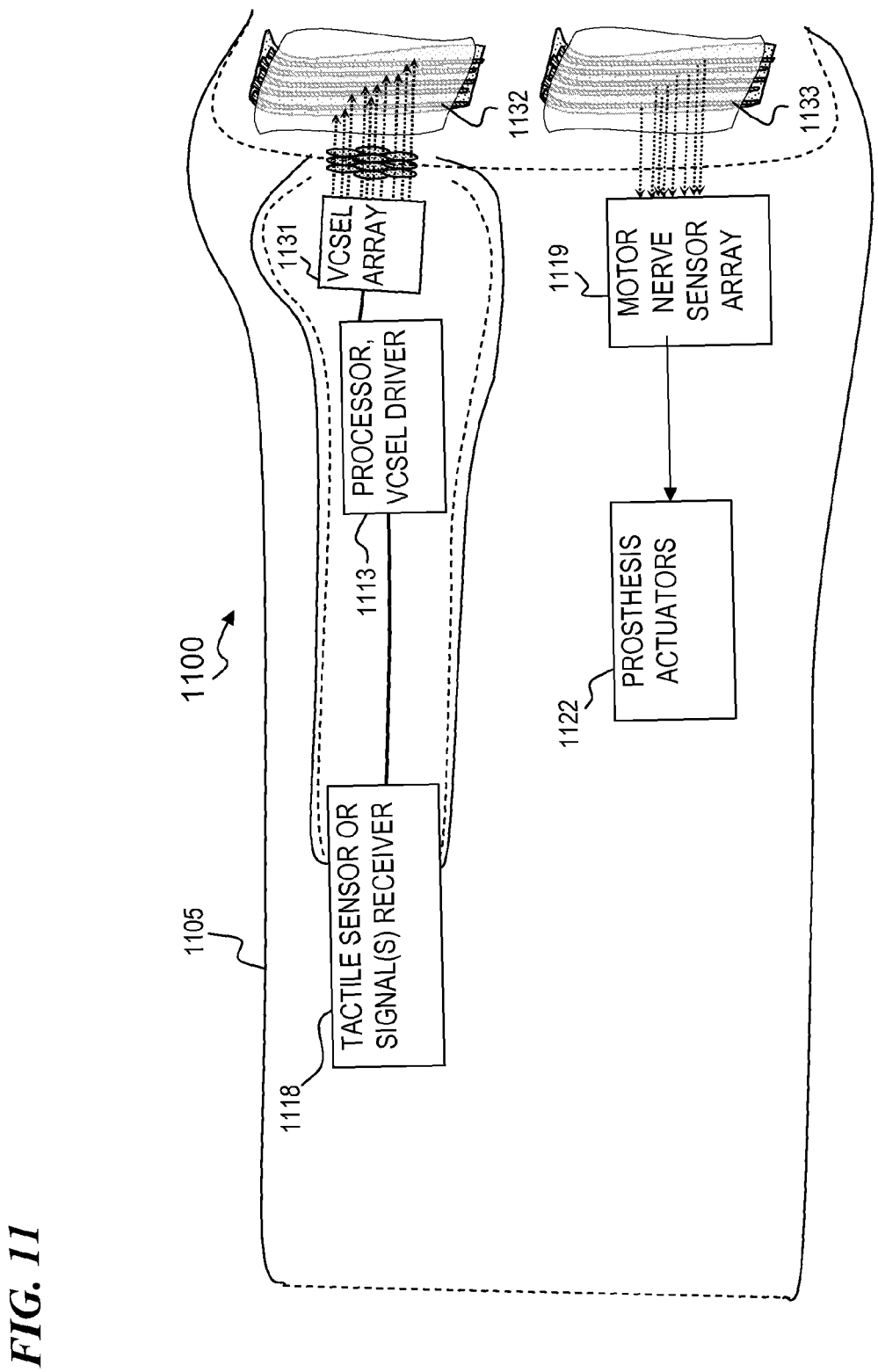
FIG. 11 is a block diagram of an external prosthesis system 1100 that uses a VCSEL array for light stimulation of animal tissue.

FIG. 11 is a block diagram of an external prosthesis system 1100 that uses a VCSEL array for light stimulation of animal tissue. In some embodiments, system 1100 includes a prosthesis housing 1105 within which are mounted a sensor system 1118, that provides tactile or other information to a processor/computer and VCSEL driver circuit 1113 that drives a VCSEL array 1131 to emit laser pulses in the wavelength range of 1.8 to 2.6 microns, and, in some such embodiments, about 1.85 microns, to stimulate sensory nerves 1132. This provides sensory information to the person or animal (through nerve connections to the brain) to which the prosthesis is connected. In some embodiments, a motor-nerve sensor array 1119 detects nerve signals sent from the brain intended to control muscles 1133, and which detected signals in turn are used to control such things as actuators 1122 on the prosthesis (graspers, limb movers, and the like).

Figure 12A:
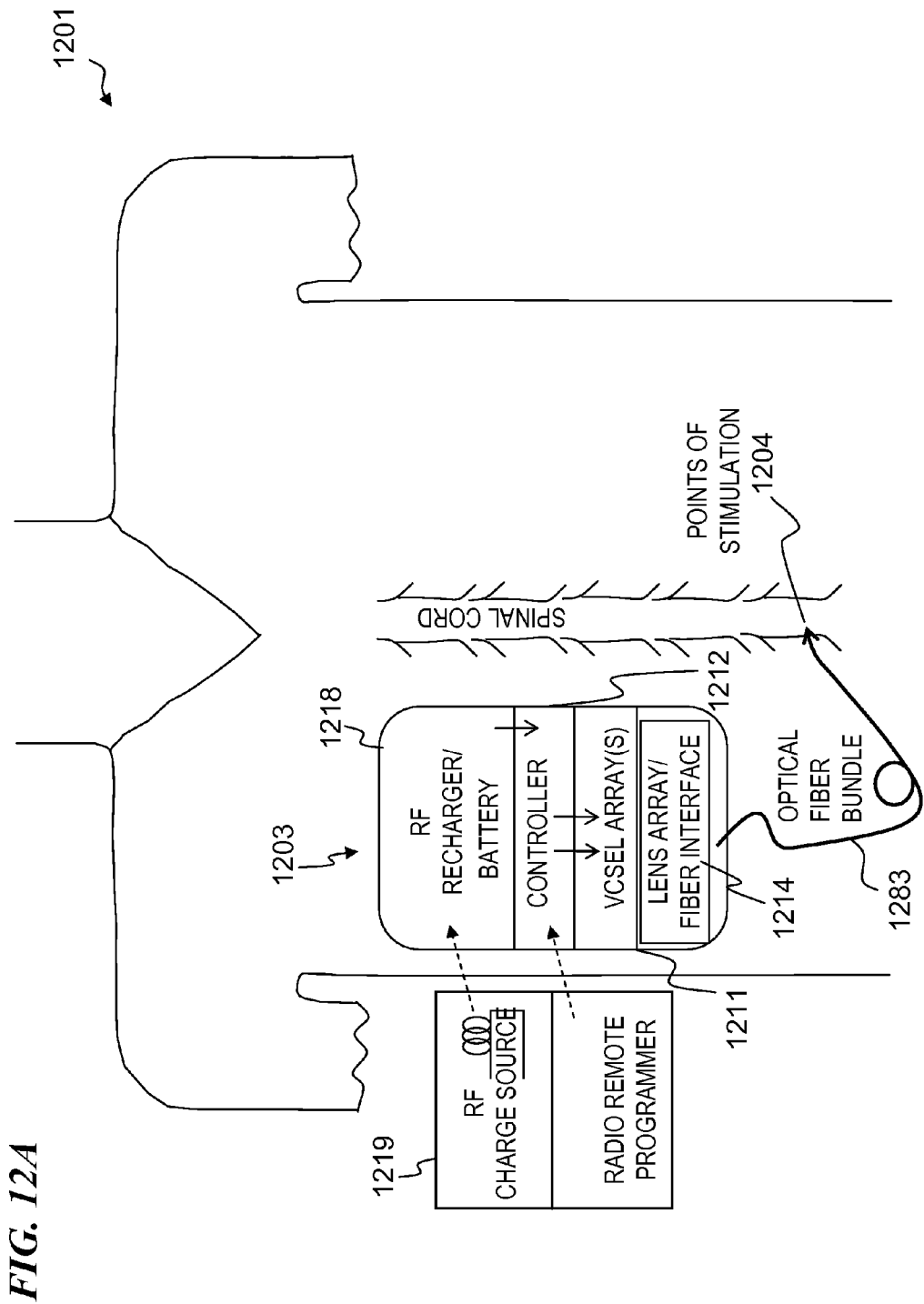
FIG. 12A is a block diagram of an implantable system 1201 that uses a VCSEL array 310 and fiber bundle 302 for light stimulation of animal tissue.

FIG. 12A is a block diagram of an implantable system 1201 that uses a VCSEL array 1211 and fiber bundle 1283 for light stimulation of animal tissue (e.g., human neural tissue or spinal cord tissue or the like). This unit is similar to that described in prior applications U.S. patent application Ser. No. 11/257,793 filed Oct. 24, 2005 titled "APPARATUS AND METHOD FOR OPTICAL STIMULATION OF NERVES AND OTHER ANIMAL TISSUE," and U.S. patent application Ser. No. 11/536,639 filed Sep. 28, 2006 and entitled "MINIATURE APPARATUS AND METHOD FOR OPTICAL STIMULATION OF NERVES AND OTHER ANIMAL TISSUE," and further descriptions can be found there. In contrast to the prior applications, the present invention provides a VCSEL array 1211 used to generate a plurality of spatially separated laser light pulses capable of stimulating human tissue to generate a nerve activity in the stimulated tissue. In some embodiments, the stimulating light pulses are applied directly to the nerves to be stimulated, while in other embodiments, such as shown, the VCSEL array is operatively coupled through a fiber interface 1214 to a fiber-optic bundle 1283 and transported to the stimulation site 1204 distal to the implanted optical stimulator 1203. In some embodiments, power is provided to the implanted optical stimulator 1203 through the laser controller 1212 from the power unit 1218 (e.g., a rechargeable battery pack, a power supply, or the like). In some embodiments, the power unit 1218 has a rechargeable battery pack (e.g., one or more batteries) that can be inductively recharged transcutaneously from remote RF charging source 1219 and a recharging receiver 1218 capable of electromagnetic coupling with the external remote RF charging source 1219 using inductive and propagation techniques.

Figure 12B:
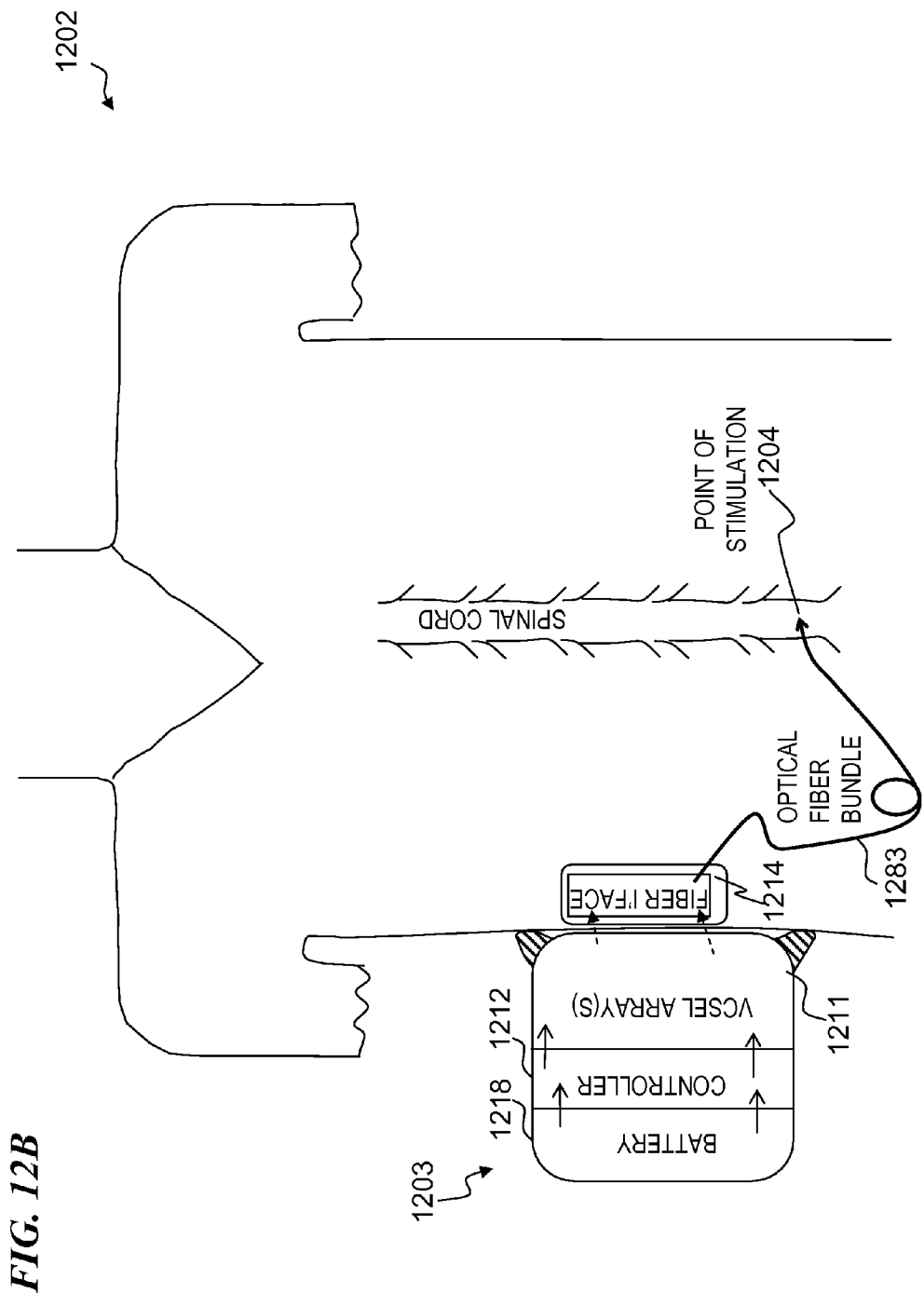
FIG. 12B is a block diagram of a partially external and partially internal system 1202 that uses a VCSEL array 310 and fiber bundle 302 for light stimulation of animal tissue.

FIG. 12B is a block diagram of a partially external and partially internal system 1202 that uses a VCSEL array 1211 and fiber bundle 1283 for light stimulation of animal tissue. This embodiment is similar to that of FIG. 12A, except that the VCSEL arrays 1211 are located in a unit 1203 deployed external to the patient, and the light signals are transmitted through the skin and applied directly to the site to be stimulated, or as shown are coupled to an optical fiber interface 1214 located under the skin, and the light is then transmitted by fibers 1283 to the sites to be stimulated 1204.

Figure 13:
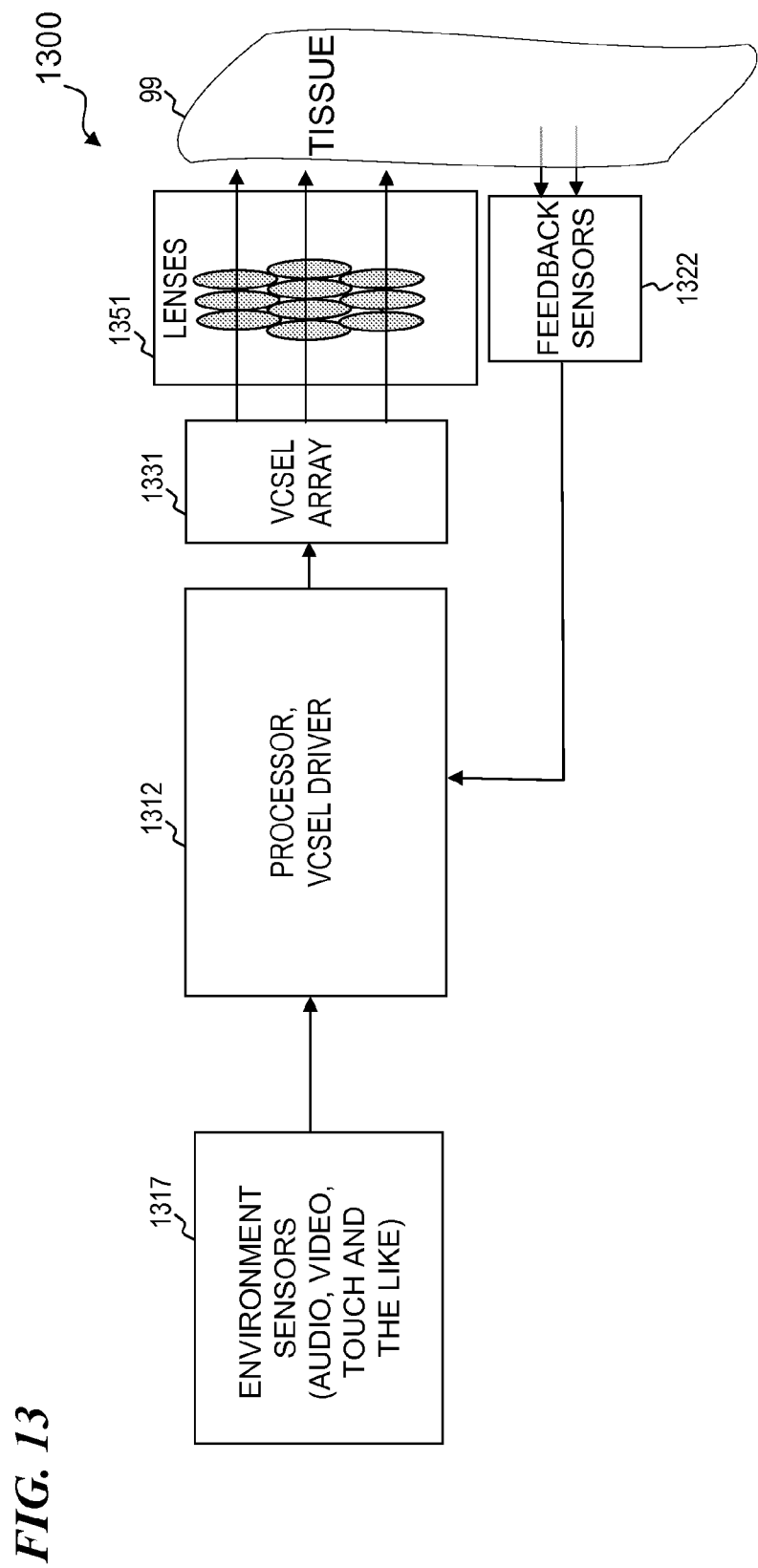
FIG. 13 is a block diagram of a system 1300 that uses a VCSEL array for light stimulation of animal tissue.

FIG. 13 is a block diagram of a system 1300 that uses a VCSEL array 1331 for light stimulation of animal tissue 99. In the embodiment shown, the system 1300 receives feedback information 1322 as to a physiological condition of the patient and/or receives information from environmental sensors 1317 (e.g., audio microphones, visual (e.g., video) signals, tactile touch, smell or odor sensors and the like), and uses this information to generate the resulting optical-driver signals sent to the VCSEL array 1331, which, in some embodiments, uses an optical system (such as an array of lenses 1351) to deliver the optical signals to the tissue 99 being stimulated.

In some embodiments, the tissue is treated (e.g., using pharmaceuticals, nano-particles, or genetic alteration or the like) to be receptive and/or activated when irradiated with a suitable wavelength, e.g., one or more wavelengths between 100 nm or lower and 800 nm or longer. In some embodiments, the light is used to separate a large molecule into two smaller molecules (e.g., where the large molecule is relatively inactive or inert, but one or both of the two smaller molecules are biologically active). In other embodiments, the light activates or inactivates a "cork" molecule that opens or closes an ion channel in the cells. In other embodiments, the light when received opens or closes an ion channel in the cells.

Figure 14:
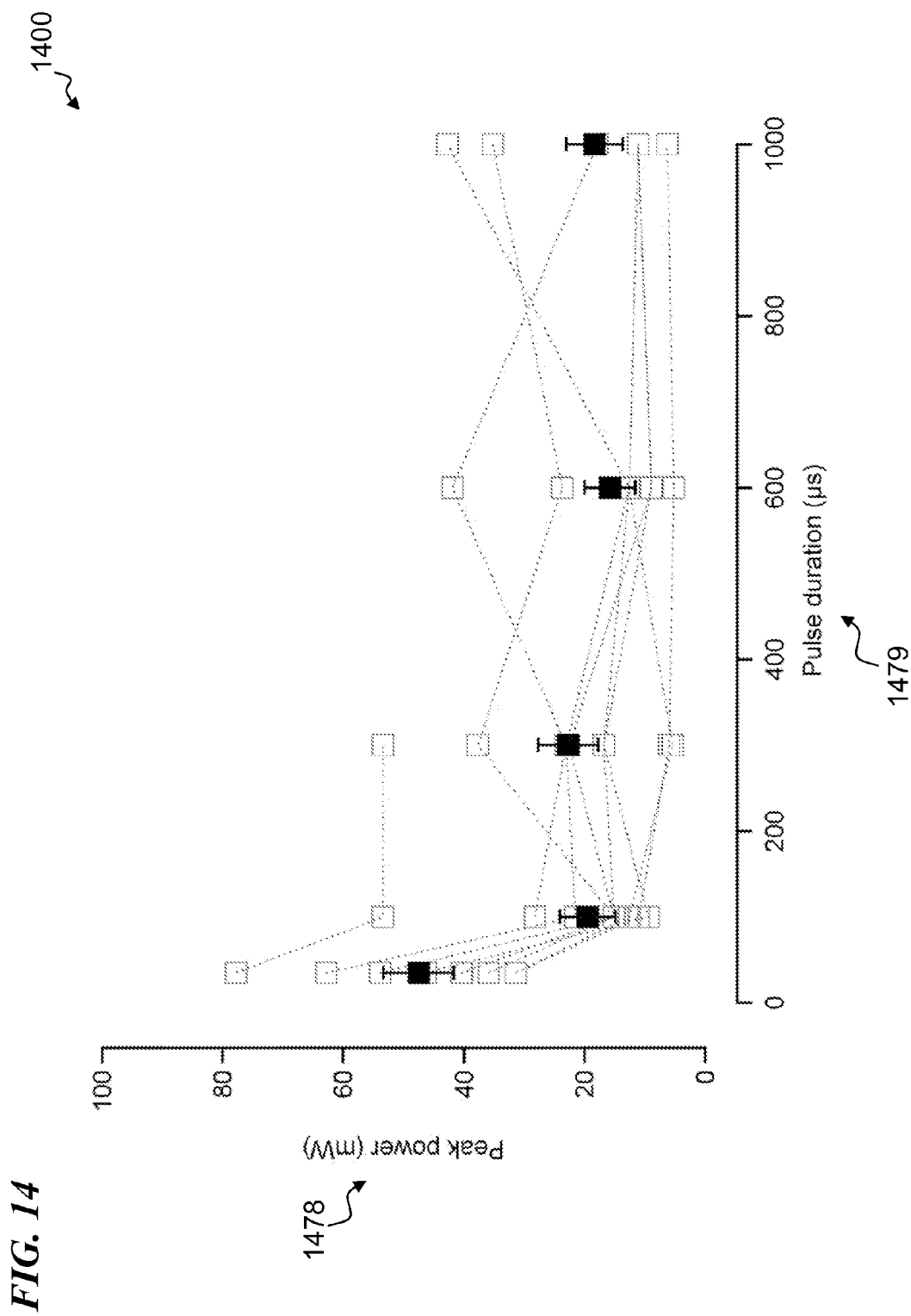
FIG. 14 is a graph 1400 displaying the peak power required for stimulation of spiral ganglion cells of the cochlea using light pulses having a wavelength of 1.87 microns as a function of pulse duration.

FIG. 14 is a graph 1400 of the peak power 1478 in mW required for stimulation of the spiral ganglion cells in the cochlea (e.g., causing a nerve activity such as a nerve action potential) using light pulses having a wavelength of 1.87 microns as a function of pulse duration 1479 in microseconds. The open squares in the graph represent actual measured peak power data for a plurality of measurements, whereas the filled squares in the graph represent the average peak power required for stimulating the spiral ganglion cells for various pulse durations. For example, in some embodiments, the average peak power of stimulating light pulses is about 20 mW for a pulse duration of about 100 microseconds.

Methods for using light to stimulate cellular activity are clinically promising techniques that allow extremely spatially selective stimulation of discrete populations of cells or axons in a non-contact manner. While the experimental setup and stimulation protocols for these methods are well documented, a compact and power efficient device will be required for clinical implementation of these methodologies. Clinical neural stimulation can benefit from the advantages associated with light stimulation; however, currently there are no technologies that allow a multi-channel light-emitting device to be used as an implantable laser or prosthetic device.

In some embodiments, the present invention provides a compact multi-channel light source operating at the optimal parameters for safe and efficient laser stimulation of excitable tissues (either optical stimulation or photostimulation as defined below) with the use of vertical-cavity surface-emitting lasers forming an array of small tissue "stimulators." A VCSEL array will allow multi-channel (with independent electronic control of each light-emitting cell) stimulation with light in a neural prosthetic device that can easily be implanted or carried by human subjects for chronic optical stimulation or photostimulation of excitable tissues. Potential uses for this device include the stimulation portion of a neural-prosthetic device that can be interfaced to sensor technology to be chronically implanted in human subjects to improve cochlear, vestibular, visual, spinal chord, or neuro-cognitive function by stimulation of nerves or neurons. Also, cardiac pacing, muscle activity, or other effector cells, tissue, or muscle can benefit from this technology by therapeutic external control of these functions with the use of light.

In some embodiments, the present invention provides a VCSEL that emits light with the optimal laser parameters for stimulating a neural tissue response such as triggering a nerve action potential, including a selected laser wavelength (e.g., in some embodiments, 1870 nm), laser-pulse duration(s), laser power (in Watts=Joules/sec), and laser radiant exposure (Joules/cm$^2$) for stimulation of cellular activity. In some embodiments, the apparatus provides independent electronic control of each laser within the laser array. In the case of closed-loop feedback implantable prosthetic devices, a sensor technology converts a biological signal (e.g., a nerve-action-potential (NAP) signal) into an electrical signal that is interfaced to software, wherein the software decides what response is appropriate and produces an appropriate electrical signal to each individual light channel within the VCSEL, which then emits the appropriate multi-channel (e.g., emitting light from a plurality of different locations and/or at one or more different wavelengths and/or pulse durations and/or intensities) light pulse(s) (stimulation-causing optical signal) that produces the corresponding biological action or physiological response (e.g., a NAP signal) within the body. In some embodiments, the stimulation-causing optical signal is delivered in free space, while in other embodiments, it is delivered using optical fibers. In some embodiments, the optical fibers are efficiently coupled to each laser within an array on one end and deliver the light through the opposite end to the appropriate tissue site to selectively stimulate cell function. In some embodiments, the VCSEL is located external to the body and coupled to optical fibers that are strategically inserted and mounted in the body to produce the intended physiological action in the stimulated tissue. In some embodiments, the VCSEL device is implanted and mounted within the body and the stimulation-causing optical signal is delivered via free beam or optical fibers to the correct location to facilitate multi-channel selective and/or precise stimulation of cell or neural function. In some embodiments, the stimulation-causing optical signal is focused on a specific nerve or small section of a nerve bundle to stimulate a specific NAP in one or just a few nerves without stimulation of a NAP in immediately adjacent nerves in a nerve bundle. In some embodiments, the parameters of the stimulation-causing optical signal include being pulsed with a duration and intensity (and optionally a pulse-repetition rate) that are effective for stimulation of neural tissues, nerves or neurons including both optical stimulation and photostimulation.

In some embodiments, the present invention provides a VCSEL array configured to output light pulses capable of optically stimulating neural tissue (e.g., cochlear nerve tissue, deep brain tissue, white brain matter tissue, gray brain matter tissue, spinal cord tissue, cardial nerve tissue, central nervous system nerve tissue, olfactory nerve tissue, optic nerve tissue, nerve bundles and the like). In some embodiments, the stimulating lights pulses have a wavelength that results in the appropriate penetration depth for effective stimulation of the tissue of interest without causing tissue damage (e.g., in some embodiments, the wavelength of stimulating light pulses is in the range of about 1.8 microns to about 2.2 microns, in some embodiments, the wavelength of stimulating light pulses is in the range of about 1.85 microns to about 2.0 microns, in some embodiments, the wavelength of stimulating light pulses is about 1.87 microns, in some other embodiments the wavelength of stimulating light pulses is in the range of about 4.0 microns to about 5.0 microns, in some other embodiments the wavelength of stimulating light pulses is in the range of about 4.2 microns to about 4.8 microns, in some other embodiments the wavelength of stimulating light pulses is in the range of about 4.4 microns to about 4.6 microns).

In some embodiments, the stimulating lights pulses have a pulse duration that results in the appropriate applied energy for effective stimulation (i.e., generation of nerve activity) of the tissue of interest without causing tissue damage. In some embodiments, the pulse duration of the stimulating light pulses is less than about 10 msec, in some embodiments, a pulse duration of the stimulating light pulses is in the range of about 10 microseconds to about hundreds of microseconds, in some embodiments, a pulse duration of the stimulating light pulses is in the range of about 10 microseconds to about 500 microseconds, in some embodiments, a pulse duration of the stimulating light pulses is in the range of about 10 microseconds to about 250 microseconds, in some embodiments, a pulse duration of the stimulating light pulses is in the range of about 10 microseconds to about 200 microseconds, in some embodiments, a pulse duration of the stimulating light pulses is in the range of about 10 microseconds to about 150 microseconds, in some embodiments, a pulse duration of the stimulating light pulses is in the range of about 10 microseconds to about 100 microseconds, in some embodiments, a pulse duration of the stimulating light pulses is in the range of about 10 microseconds to about 50 microseconds. In some embodiments, a pulse duration of about 100 microseconds is used for the stimulation of spiral ganglion cells in the cochlea.

In some embodiments, the stimulating lights pulses have a pulse intensity that results in the appropriate applied energy for effective stimulation (i.e., generation of nerve activity) of the tissue of interest without causing tissue damage. In some embodiments, depending on particular tissue geometry, the pulse intensity of the stimulating light pulses for stimulating peripheral nerves provides a radiant exposure that is less than about 1 J/cm$^2$ or about 10 W of average power. In some embodiments, the pulse intensity of the stimulating light pulses that are used for stimulating cochlear nerves is much less than the radiant exposure and power required for stimulating peripheral nerves.

In some embodiments, the stimulating lights pulses have a pulse-repetition rate (PRR) to duplicate the neural firing rate of stimulated tissue undergoing normal physiologic action. In some embodiments, the PRR is in the range of about 0 Hz to about 20,000 kHz, the PRR is in the range of about 10-20 Hz, the PRR is in the range of about 20-50 Hz, the PRR is in the range of about 50-100 Hz, the PRR is in the range of about 100-200 Hz, the PRR is in the range of about 200-500 Hz, the PRR is in the range of about 500-1000 Hz, the PRR is in the range of about 1-2 kHz, the PRR is in the range of about 2-5 kHz, the PRR is in the range of about 5-10 kHz, the PRR is in the range of about 10-20 kHz, the PRR is in the range of about 20-50 kHz, the PRR is in the range of about 50-100 kHz, the PRR is in the range of about 100-200 kHz, the PRR is in the range of about 200-500 kHz, the PRR is in the range of about 500-1000 kHz, or the PRR is greater than about 1 MHz.

In some embodiments, the present invention provides a VCSEL array configured to output light pulses capable of providing photostimulation of neural tissue. In some embodiments, the light pulses used in light-mediated uncaging photostimulation have a wavelength in the range of about 100 nm to about 1400 nm, in some embodiments, the light pulses used in light-mediated uncaging photostimulation have a wavelength in the range of about 100 nm to about 200 nm, in some embodiments, the light pulses used in light-mediated uncaging photostimulation have a wavelength in the range of about 200 nm to about 300 nm, in some embodiments, the light pulses used in light-mediated uncaging photostimulation have a wavelength in the range of about 300 nm to about 400 nm, in some embodiments, the light pulses used in light-mediated uncaging photostimulation have a wavelength in the range of about 400 nm to about 500 nm, in some embodiments, the light pulses used in light-mediated uncaging photostimulation have a wavelength in the range of about 500 nm to about 600 nm, in some embodiments, the light pulses used in light-mediated uncaging photostimulation have a wavelength in the range of about 600 nm to about 700 nm, in some embodiments, the light pulses used in light-mediated uncaging photostimulation have a wavelength in the range of about 700 nm to about 800 nm, in some embodiments, the light pulses used in light-mediated uncaging photostimulation have a wavelength in the range of about 800 nm to about 900 nm, in some embodiments, the light pulses used in light-mediated uncaging photostimulation have a wavelength in the range of about 900 nm to about 1000 nm, in some embodiments, the light pulses used in light-mediated uncaging photostimulation have a wavelength in the range of about 1000 nm to about 1100 nm, in some embodiments, the light pulses used in light-mediated uncaging photostimulation have a wavelength in the range of about 1100 nm to about 1200 nm, in some embodiments, the light pulses used in light-mediated uncaging photostimulation have a wavelength in the range of about 1200 nm to about 1300 nm, in some embodiments, the light pulses used in light-mediated uncaging photostimulation have a wavelength in the range of about 1300 nm to about 1400 nm, in some embodiments, the light pulses used in light-mediated uncaging photostimulation have a wavelength of about 355 nm.

In some embodiments, the present invention provides a VCSEL array configured to output light pulses capable of providing photostimulation of neural tissue. In some embodiments, the light pulses used for photostimulation by genetic insertion of phototransduction proteins into the cell membrane have a wavelength in the range of about 100 nm to about 1400 nm, in some embodiments, in the range of about 100 nm to about 200 nm, in the range of about 200 nm to about 300 nm, in the range of about 300 nm to about 400 nm, in the range of about 400 nm to about 500 nm, in the range of about 500 nm to about 600 nm, in the range of about 600 nm to about 700 nm, in the range of about 700 nm to about 800 nm, in the range of about 800 nm to about 900 nm, in the range of about 900 nm to about 1000 nm, in the range of about 1000 nm to about 1100 nm, in the range of about 1100 nm to about 1200 nm, in the range of about 1200 nm to about 1300 nm, in the range of about 1300 nm to about 1400 nm, and in the range of about 450 nm to about 600 nm.

In some embodiments, the present invention provides a VCSEL array configured to output light pulses capable of providing photostimulation of neural tissue. In some embodiments, the light pulses used for photostimulation by a photoswitch between open and closed channels based on light-induced conformational change have a wavelength in the range of about 100 nm to about 1400 nm, in some embodiments, in the range of about 100 nm to about 200 nm, in the range of about 200 nm to about 300 nm, in the range of about 300 nm to about 400 nm, in the range of about 400 nm to about 500 nm, in the range of about 500 nm to about 600 nm, in the range of about 600 nm to about 700 nm, in the range of about 700 nm to about 800 nm, in the range of about 800 nm to about 900 nm, in the range of about 900 nm to about 1000 nm, in the range of about 1000 nm to about 1100 nm, in the range of about 1100 nm to about 1200 nm, in the range of about 1200 nm to about 1300 nm, in the range of about 1300 nm to about 1400 nm, in the range of about 350 nm to about 450 nm for short wavelengths to switch between the open and closed state, and in the range of about 450 nm to about 600 nm for long wavelengths to switch between the open and closed state.

In some embodiments, the photostimulating light pulses for all types of photostimulation have a pulse duration that results in the appropriate applied energy for effective photostimulation (i.e., generation of nerve activity) of the tissue of interest without causing tissue damage. In some embodiments, the pulse duration is in the range of about 1 microsecond to about 10 msec, in the range of about 10 microseconds to about 50 microseconds, in the range of about 50 microseconds to about 100 microseconds, in the range of about 100 microseconds to about 250 microseconds, in the range of about 250 microseconds to about 500 microseconds, in the range of about 500 microseconds to about 750 microseconds, in the range of about 750 microsecond to about 1 msec, in the range of about 1 msec to about 2 msec, in the range of about 2 msec to about 3 msec, in the range of about 2 msec to about 3 msec, in the range of about 3 msec to about 4 msec, in the range of about 5 msec to about 5 msec, in the range of about 5 msec to about 6 msec, in the range of about 6 msec to about 7 msec, in the range of about 7 msec to about 8 msec, in the range of about 8 msec to about 9 msec, in the range of about 9 msec to about 10 msec.

In some embodiments, the photostimulating light pulses for all types of photostimulation have a pulse intensity that results in the appropriate applied energy for effective photostimulation (i.e., generation of nerve activity) of the tissue of interest without causing tissue damage. In some embodiments, the pulse intensity is about less than 100 mW power for all photostimulation types; in some embodiments, the pulse intensity is in a range of about 1 mW per channel to about 10 mW per channel, a range of about 10 mW per channel to about 20 mW per channel, a range of about 20 mW per channel to about 30 mW per channel, a range of about 30 mW per channel to about 40 mW per channel, a range of about 40 mW per channel to about 50 mW per channel, a range of about 50 mW per channel to about 60 mW per channel, a range of about 60 mW per channel to about 70 mW per channel, a range of about 70 mW per channel to about 80 mW per channel, a range of about 80 mW per channel to about 90 mW per channel, a range of about 90 mW per channel to about 100 mW per channel.

In some embodiments, the photostimulating stimulating light pulses have a pulse-repetition rate (PRR) to duplicate the neural firing rate of stimulated tissue undergoing normal physiologic action. In some embodiments, the PRR is in the range of about 0 Hz to about 20,000 kHz, the PRR is in the range of about 10-20 Hz, the PRR is in the range of about 20-50 Hz, the PRR is in the range of about 50-100 Hz, the PRR is in the range of about 100-200 Hz, the PRR is in the range of about 200-500 Hz, the PRR is in the range of about 500-1000 Hz, the PRR is in the range of about 1-2 kHz, the PRR is in the range of about 2-5 kHz, the PRR is in the range of about 5-10 kHz, the PRR is in the range of about 10-20 kHz, the PRR is in the range of about 20-50 kHz, the PRR is in the range of about 50-100 kHz, the PRR is in the range of about 100-200 kHz, the PRR is in the range of about 200-500 kHz, the PRR is in the range of about 500-1000 kHz, or the PRR is greater than about 1 MHz.

In some embodiments, the present invention provides a VCSEL array acting as the stimulation component in a neural prosthetic device that uses light for stimulation of neural structures to restore damaged cellular function. In some embodiments, the present invention provides therapeutic devices that include vestibular prosthetics for balance restoration and vestibular function, cochlear prosthetics for restoration of hearing and cochlear function, retinal prosthesis, peripheral nerve neurostimulators to restore function (e.g., spinal cord rootlets or nerve prostheses), or neuroprostheses for the central nervous system (brain and spinal cord).

In some embodiments, the present invention provides an implantable apparatus capable of therapeutic treatment of the vestibular system by stimulating the vestibule, Scarpa's ganglion cells, the vestibular nerve, nuclei in the brain dedicated to balance, or other brain structures or neural pathways that contribute to an individual's balance and posture.

In some embodiments, the present invention provides an implantable apparatus capable of therapeutically treating human and animal hearing deficiencies by stimulating the cochlea, spiral ganglion cells, the cochlear nerve, nuclei in the brain dedicated to hearing, or other brain structures or neural pathways related to an individual's hearing.

In some embodiments, the present invention provides an implantable apparatus capable of therapeutically treating human and animal visual deficiencies by stimulating the retinal ganglion cells, bipolar cells, other visual integrating cells, the optic nerve, the visual cortex, or other brain structures or neural pathways that contribute to an individual's vision.

In some embodiments, the present invention provides an implantable apparatus capable of therapeutically treating human and animal visual deficiencies peripheral nerves or the spinal cord to restore function, such as sensory or motor function of extremities.

In some embodiments, the present invention provides an apparatus capable of therapeutic treatment of neural functions like deep brain stimulation to restore function in movement disorders, treatment of epilepsy, depression, and stimulation of other brain nuclei that leads to a correction in impaired function as well as treatment of effector organs like the heart and endocrine system for use in cardiac pacing or control of hormonal regulation by stimulating the pituitary gland or limbic system.

Definitions Relevant to Light Stimulation of Cellular Function

As used herein, light stimulation is defined as the direct or indirect use of light to stimulate cellular activity from, in most cases neural tissues, although possibly in cardiac tissue, muscle, or other effector cells, tissues, and organs. The direct use of light for stimulation of cellular or axonal activity is referenced as optical stimulation. The indirect use of light for stimulation of cellular or axonal activity is referenced as photostimulation.

As used herein, optical stimulation is defined as the direct induction of an evoked physiological potential in native (unaltered) excitable cells in response to a transient targeted deposition of optical energy (Wells et al. 2006). This implies that only a pulsed source can be used for stimulation of neural tissue, and that continuous-wave irradiation will not lead to compound action potential generation. Typically, uses of lasers in biomedicine rely on high-energy effects like tissue ablation and photoacoustic wave generation (Welch, Motamedi et al. 1991; Wietholt, Alberty et al. 1992; Jansen, Asshauer et al. 1996; Vogel and Venugopalan 2003; Kanjani, Jacob et al. 2004). As used herein, "low level optical signals" have the radiant exposure needed for optical stimulation of neural tissue, which is "low level" relative to the conventional therapeutic laser applications that lead to tissue coagulation and ablation. Optical stimulation has been shown to be possible using light pulses less than 10 milliseconds (msec) delivered directly to the tissue with almost any wavelength across the infrared portion of the spectrum (Wells et al. 2005). The safest and most efficient stimulation has been demonstrated using wavelengths with penetration depths between 100-800 µm in soft tissue (Wells et al. 2005; Wells et al. 2007). The optimal wavelength for stimulation is dependent upon the target tissue's morphology and structure; for the sciatic nerve and spiral ganglion cells of the cochlea these wavelengths include (but are not limited to) 1.8-2.12 µm and 4-5 µm. The underlying mechanism responsible for optical stimulation is a transient thermal phenomenon (Wells et al. 2006).

Optical stimulation work in the cochlea has shown, in contrast to electric stimulation, that pulses of infrared light can stimulate small populations of cochlear spiral ganglion cells, thus proving that higher frequency fidelity is possible (Izzo 2006a). In these experiments, response amplitudes were stable over extended stimulation times and no evidence of histological tissue damage was seen using physiologic repetition rates (Izzo 2006b), thus indicating that chronic stimulation can be done safely. The innovative optical cochlear stimulator (OCS) has been shown to safely stimulate the auditory nerve at physiologic repetition rates (50-200 Hz) and at various wavelengths. Extreme spatial stimulation of the auditory nerve is possible and for extended periods of time using a benchtop infrared nerve stimulator. FIG. 15 shows the peak power versus pulse duration needed to stimulate spiral ganglion cells of the cochlea to restore function. In some embodiments, the stimulating VCSEL will require <100 mW emitted from each channel to provide a reliable stimulatory effect in the incident tissue.

As used herein, photostimulation is defined as a methodology that genetically modifies cellular apparatus or structures within cells, usually proteins (i.e., ion channels or receptors), such that they become sensitive to light. Exposure to the optimal light parameters causes a conformational or structural change in light-sensitive molecules that ultimately results in stimulation of excitable tissue, synaptic transmission, or stimulation of some cellular function and physiologic effect. There are currently three general methods relying on neural photostimulation within genetically manipulated tissue. These methods were developed largely over the last decade to thwart the limits of electricity in search of less invasive and more precise control of neural function. In contrast to direct optical neural stimulation, each relies on the use of flashed light (transient delivery) to activate genetically modified cellular secondary messengers that results in neuronal firing.

Light-mediated uncaging of chemically modified neural signaling molecules represents the largest and most momentous class of photostimulation in this discussion. Researchers have successfully tagged the essential molecules for excitability with chemicals that degrade when exposed to light, rendering the "caged" molecule active. Light-sensitive, biologically active compounds were used by McCray and Trentham employing caged ATP for muscle-fiber excitation. The chemical and physical aspects of generating effector molecules from their photosensitive precursors, i.e., caged compounds, are reviewed by these researchers (Lester and Nerbonne 1982; McCray and Trentham 1989). More recently, optical release of caged neurotransmitters (often glutamate), facilitated with relatively low levels of pulsed UV light (355 nm), has allowed the localized control of excitation within cultured neurons and in vitro slice preparation for quantal analysis and investigation of cortical circuitry (Dodt, Eder et al. 1999; Dodt, Eder et al. 2002; Dodt, Schierloh et al. 2003; Eder, Zieglgansberger et al. 2004; Kotter, Schubert et al. 2005)) (for review see (Eder, Zieglgansberger et al. 2004) and (Thompson, Kao et al. 2005)). This work has been extended to in vivo use in genetically altered rat cortex (Bureau, Shepherd et al. 2004). Parker from California, Irvine has taken a slightly different approach by using flash photolysis of caged inositol 1,4,5-trisphosphate ($IP_3$) (Parker and Ivorra 1992; Stutzmann, LaFerla et al. 2003) to cause calcium release in pyramidal neurons for study of excitability and plasticity of neurons (for review see (Augustine 1994)). While this method features a high degree of selectivity, dependent upon selective insertion of caging compounds, the temporal selectivity in activation is limited to millisecond timescales.

A second division of photostimulation methodology exploits cation channels involved in phototransduction to create light-sensitive neurons by genetic insertion of these proteins into the cellular membrane. Researchers from the Miesenbock Lab at Yale were the first to genetically implant retinal photosensitive channel proteins into precise locations within Drosophila neurons for depolarization upon exposure to visible light. Selective photostimulation of genetically chARGed neurons (Coexpression of the Drosophila photoreceptor genes encoding rrestin-2, hodopsin (formed by liganding opsin with retinal), and the α subunit of the cognate heterotrimeric protein—an explosive combination termed "chARGe"—sensitizes generalist vertebrate neurons to light.) (Zemelman, Lee et al. 2002; Zemelman, Nesnas et al. 2003) is moderated by plasmid injection into cultured neurons leading to G-protein gated, light-sensitive channel expression. The process yields corresponding light control of depolarization in otherwise light-insensitive neurons. Literature has described remote control of behavior using this technique for neuronal photostimulation (Lima and Miesenbock 2005). Likewise, hyperpolarization with this technique was revealed with the use of rat rhodopsin in cultured hippocampal neurons (Li, Gutierrez et al. 2005). A modified, more temporally precise technique developed at Stanford University relies on insertion of a natural, rapidly gated, light-sensitive algal protein Channelrhodopsin-2 and has been demonstrated in mammalian neurons (Nagel, Szellas et al. 2003; Nagel, Szellas et al. 2005). Here, illumination with blue light (470 nm) triggers a conformational change to open the channel pore and evokes reversible depolarization 50 microsec after light irradiation (Boyden, Zhang et al. 2005; Schroll, Riemensperger et al. 2006). A final and relatively new category of photostimulation utilizes chemical modification of ion channels and receptors to construct a photoswitch, providing a light-sensitive channel expressed in neurons. The protein structure is modified at the gate to include a functional group for selective conjugation to an engineered potassium channel, a covalently bound pore blocker, and a photoisomerizable azobenzene. Irradiation with long (580 nm) and short (380 nm) wavelengths allows switching between the cis and trans isomer of the axobenzene arm, thus alternating between the blocked and open channel state (Banghart, Borges et al. 2004). These synthetic photoisomerizable axobenzene-regulated K(+) (SPARK) channels allow spatially precise and reversible control in neural excitation; however, the temporal selectivity is limited to seconds for response to light (Chambers, Banghart et al. 2006). A modified approach involves axobenzene-tethered glutamate receptors (Volgraf, Gorostiza et al. 2006). While interesting and useful in the study of neuronal circuits, synaptic connections, and glutamate sensitivity, the above photostimulation techniques (for review see (Zhang, Wang et al. 2006)) are not considered herein to be a form of optical stimulation given the stated definition of optical stimulation provided above.

The following references, cited above, are incorporated herein in their entirety by reference:

Augustine, G. J. (1994). "Combining patch-clamp and optical methods in brain slices." *J Neurosci Methods* 54(2): 163-9.

Banghart, M., K. Borges, et al. (2004). "Light-activated ion channels for remote control of neuronal firing." *Nat Neurosci* 7(12): 1381-6.

Boyden, E. S., F. Zhang, et al. (2005). "Millisecond-timescale, genetically targeted optical control of neural activity." *Nat Neurosci* 8(9): 1263-8.

Bureau, I., G. M. Shepherd, et al. (2004). "Precise development of functional and anatomical columns in the neocortex." *Neuron* 42(5): 789-801.

Chambers, J. J., M. R. Banghart, et al. (2006). "Light-induced depolarization of neurons using a modified shaker k+channel and a molecular photoswitch." *J Neurophysiol* 96(5): 2792-6.

Deal, W. J., B. F. Erlanger, et al. (1969). "Photoregulation of biological activity by photochromic reagents. 3. Photoregulation of bioelectricity by acetylcholine receptor inhibitors." *Proc Natl Acad Sci USA* 64(4): 1230-4.

Dodt, H., M. Eder, et al. (1999). "Precisely localized LTD in the neocortex revealed by infrared-guided laser stimulation." *Science* 286(5437): 110-3.

Dodt, H. U., M. Eder, et al. (2002). "Infrared-guided laser stimulation of neurons in brain slices."*Sci STKE* 2002(120): PL2.

Dodt, H. U., A. Schierloh, et al. (2003). "Circuitry of rat barrel cortex investigated by infrared-guided laser stimulation." *Neuroreport* 14(4): 623-7.

Eder, M., W. Zieglgansberger, et al. (2004). "Shining light on neurons—elucidation of neuronal functions by photostimulation." *Rev Neurosci* 15(3): 167-83.

Izzo, A. D., Walsh, J. T., et al. (2007). "Optical Parameter Variability in Laser Nerve Stimulation: A Study of Pulse Duration, Repetition Rate, and Wavelength." Biomedical Engineering, IEEE Transactions on. Vol. 54, Issue: 6, Part 1, Pages: 1108-1114.

Jansen, E. D., T. Asshauer, et al. (1996). "Effect of pulse duration on bubble formation and laser-induced pressure waves during holmium laser ablation." *Lasers Surg Med* 18(3): 278-93.

Kanjani, N., S. Jacob, et al. (2004). "Wavefront- and topography-guided ablation in myopic eyes using Zyoptix." J Cataract Refract Surg 30(2): 398-402.

Kaufman, H., S. M. Vratsanos, et al. (1968). "Photoregulation of an enzymic process by means of a light-sensitive ligand." *Science* 162(861): 1487-9.

Kotter, R., D. Schubert, et al. (2005). "Optical release of caged glutamate for stimulation of neurons in the in vitro slice preparation." *J Biomed Opt* 10(1): 11003.

Lester, H. A. and J. M. Nerbonne (1982). "Physiological and pharmacological manipulations with light flashes." *Annu Rev Biophys Bioeng* 11: 151-75.

Li, X., D. V. Gutierrez, et al. (2005). "Fast noninvasive activation and inhibition of neural and network activity by vertebrate rhodopsin and green algae channelrhodopsin." *Proc Natl Acad Sci USA* 102(49): 17816-21.

Lima, S. Q. and G. Miesenbock (2005). "Remote control of behavior through genetically targeted photostimulation of neurons." *Cell* 121(1): 141-52.

McCray, J. A. and D. R. Trentham (1989). "Properties and uses of photoreactive caged compounds." *Annu Rev Biophys Biophys Chem* 18: 239-70.

Nagel, G., T. Szellas, et al. (2003). "Channelrhodopsin-2, a directly light-gated cation-selective membrane channel." *Proc Natl Acad Sci USA* 100(24): 13940-5.

Nagel, G., T. Szellas, et al. (2005). "Channelrhodopsins: directly light-gated cation channels." *Biochem Soc Trans* 33(Pt 4): 863-6.

Parker, I. and I. Ivorra (1992). "Characteristics of membrane currents evoked by photoreleased inositol trisphosphate in *Xenopus oocytes*." *Am J Physiol* 263(1 Pt 1): C154-65.

Schroll, C., T. Riemensperger, et al. (2006). "Light-induced activation of distinct modulatory neurons triggers appetitive or aversive learning in Drosophila larvae." *Curr Biol* 16(17): 1741-7.

Stutzmann, G. E., F. M. LaFerla, et al. (2003). "Ca2+ signaling in mouse cortical neurons studied by two-photon imaging and photoreleased inositol triphosphate." *J Neurosci* 23(3): 758-65.

Thompson, S. M., J. P. Kao, et al. (2005). "Flashy science: controlling neural function with light." *J Neurosci* 25(45): 10358-65.

Varfolomeyev, S. D., A. M. Klibanov, et al. (1971). "Light-initiated enzymic activity caused by photostereoisomerization of cis-4-nitrocinnamoyl-alpha-chymotrypsin." *FEBS Lett* 15(2): 118-120.

Vogel, A. and V. Venugopalan (2003). "Mechanisms of pulsed laser ablation of biological tissues." *Chem Rev* 103(2): 577-644.

Volgraf, M., P. Gorostiza, et al. (2006). "Allosteric control of an ionotropic glutamate receptor with an optical switch." *Nat Chem Biol* 2(1): 47-52.

Welch, A. J., M. Motamedi, et al. (1991). "Laser thermal ablation." *Photochem Photobiol* 53(6): 815-23.

Wells, J. D., Kao, C., Jansen, E. D., Konrad, P., Mahadevan-Jansen (2007). "Optically mediated nerve stimulation: Identification of injury thresholds." *Lasers in Surgery and Medicine* 39(6): 513-26.

Wells, J. D., Kao, C., Jansen, E. D., Konrad, P., Mahadevan-Jansen, A. (2005). "Application of Infrared Light for in vivo Neural Stimulation." *Journal of Biomedical Optics* 10: 064003.

Wells, J. D., Kao, C., Mariappan, K., Albea, J., Jansen, E. D., Konrad, P., Mahadevan-Jansen, A. (2005). "Optical Stimulation of Neural Tissue in vivo." *Optics Letters* 30(5): 504-507.

Wells, J. D., Kao, C. C., Konrad, P., Milner, T., Kim, J., Mahadevan-Jansen, A., Jansen, E. D. (2006). "Biophysical mechanism responsible for low-level, transient optical stimulation of peripheral nerve." *Biophysical Journal*.

Wells, J. D., Konrad, P., Kao, C., Jansen, E. D., Mahadevan-Jansen, A. (2006). "Pulsed laser versus electrical energy for peripheral nerve stimulation." *Journal of Neuroscience Methods* 163(2): 326-37.

Wietholt, D., J. Alberty, et al. (1992). "Nd-Yag Laser-Photocoagulation—Acute Electrophysiological, Hemodynamic, and Morphological Effects in Large Irradiated Areas." *Pace-Pacing and Clinical Electrophysiology* 15(1): 52-59.

Zemelman, B. V., G. A. Lee, et al. (2002). "Selective photostimulation of genetically chARGed neurons." *Neuron* 33(1): 15-22.

Zemelman, B. V., N. Nesnas, et al. (2003). "Photochemical gating of heterologous ion channels: remote control over genetically designated populations of neurons." *Proc Natl Acad Sci USA* 100(3): 1352-7.

Zhang, F., L. P. Wang, et al. (2006). "Channelrhodopsin-2 and optical control of excitable cells." *Nat Methods* 3(10): 785-92.

In some embodiments, the present invention provides a VCSEL array configured such that the stimulation thresholds are low enough to use VCSELs for stimulation and photostimulation of neural tissue, since VCSELs cannot generate nearly the same optical output power as edge-emitter lasers that are operated at high power and heat. Recent work at Northwestern by Claus Richter et al. states "The mammalian inner ear processes sound with high sensitivity and fine resolution over a wide frequency range. The underlying mechanism for this remarkable ability is the "cochlear amplifier," which operates by modifying cochlear micromechanics. However, it is largely unknown how the cochlea implements this modification. While gradual improvements in experimental techniques have yielded ever-better descriptions of gross basilar membrane vibration, the internal workings of the organ of Corti and of the tectorial membrane have resisted exploration. Although measurements of cochlear function in mice with a gene mutation for α-tectorin indicate the tectorial membrane's key role in the mechanoelectrical transformation by the inner ear, direct experimental data on the tectorial membrane's physical properties are limited, and only few direct measurements on tectorial micromechanics are available. Using the hemicochlea, we are able to show that a tectorial membrane stiffness gradient exists along the cochlea, similar to that of the basilar membrane. In artificial perilymph (but with low calcium), the transversal and radial driving point stiffnesses change at a rate of −4.0 dB/mm and −4.9 dB/mm, respectively, along the length of the cochlear spiral. In artificial endolymph, the stiffness gradient for the transversal component was −3.4 dB/mm. Combined with the changes in tectorial membrane dimensions from base to apex, the radial stiffness changes would be able to provide a second frequency-place map in the cochlea. Young's modulus, which was obtained from measurements performed in the transversal direction, decreased by −2.6 dB/mm from base to apex." Tectorial Membrane Stiffness Gradients, Richter et al., *Biophysical Journal* 93:2265-2276 (2007) (First Published *Biophys. J. BioFAST:* May 11, 2007. doi:10.1529/biophysj.106.094474) demonstrated a regime where the requisite energy for stimulation is provided without exceeding the peak power capability of a VCSEL. The present invention identifies potential applications and anticipated requirements.

In some embodiments, VCSELs are advantageous in prosthetic applications because:

They generate less heat than edge emitting lasers, due to their lower thresholds and better efficiencies. This is important because of difficulties associated with dissipating heat from an implanted device in the human body, as well as the importance of minimizing the power supply required to power the VCSELs.

It is easier to create two-dimensional, individually addressable arrays because they are surface-emitting structures, VCSELs can be photolithographically defined in any pattern required in two dimensions. This is almost impossible using edge emitters. In some embodiments, the VCSELs are arrayed in gridded (e.g., Cartesian X-Y) arrays for ease of fabrication; in other embodiments, the VCSELs are located in a pattern customized in the shape of the structure to be stimulated in the human body (e.g., a spiral pattern for the cochlea).

VCSELs are easier to integrate with electronics. Instead of just having an array of light emitters one can create an array of emitters and their associated drive electronics. It is difficult to optimize a fabrication process for both optical and electronic devices simultaneously, it is theoretically possible, particularly using GaAs and InP substrates (this corresponds to the 780-1000-nm and 1300-1600-nm wavelength ranges).

VCSELs are easier to integrate with a lens array. In some embodiments, overlaying a VCSEL array with a microlens array would create an array of collimated emitters that could then be projected onto the target tissue that allows the stimulator to stand off from the area being stimulated (and may even be external to the body).

VCSELs are ultimately cheaper in production than edge emitters because they can be fully fabricated and tested at the wafer level. Edge emitters must be cleaved and coated as individual die or 1-D arrays before they can be tested.

VCSEL arrays can be made much smaller than edge-emitting arrays due to the cavity-length difference and device-spacing constraints.

In some embodiments, the present invention provides an apparatus and method that use VCSELs for medical devices in the human body (where the VCSELs can be either inside or immediately outside the body but coupled into the body).

In some embodiments, the present invention provides VCSEL arrays configured to output light pulses capable of stimulating human tissue and capable of selectively illuminating human tissue, the VCSEL arrays include a plurality of VCSELs and in some embodiments, the wavelength of light pulses output from VCSELs in the VCSEL array varies across the VCSEL array in order to optimize the penetration depth of the light pulses into the human tissue to target regions within the human tissue residing at differing depths. For example, in some embodiments, the VCSEL array includes VCSELs outputting light pulses having a wavelength capable of shallow penetration into human tissue, VCSELs outputting light pulses having a wavelength capable of moderate penetration into human tissue and VCSELs outputting light pulses having a wavelength capable of deep penetration into human tissue.

In some embodiments, the present invention provides VCSEL arrays configured to output light pulses capable of stimulating human tissue and capable of selectively illuminating human tissue, wherein the VCSEL arrays are temperature tuned in order to provide wavelength selection. For example, in some embodiments, a heating element (e.g., a resistive heater, a solid state heater cooler, a thin-film heater or the like) is integrated with the VCSEL array to provide heat to the VCSELs to control the temperature of the VCSELs to tune the wavelength of the light pulses output by the VCSELs.

In various embodiments, the present invention provides VCSELs for deep brain stimulation (DBS), cochlear, vestibular, or other nerve-stimulating implants, VCSELs for use in artificial limbs (for tactile feedback, position sensing, etc.), VCSELs for direct stimulation of neural tissue, VCSELs for selective illumination of neural tissue having an emission wavelength between 250-400 nm, VCSELs for generating a neural activity (e.g., a nerve action pulse) with an emission wavelength between 1.8-2.2 microns, one-dimensional or two dimensional VCSEL arrays, VCSEL arrays integrated with lens arrays or fiber lens, VCSEL arrays integrated with electronics, VCSELs arranged immediately adjacent to the tissue being stimulated, VCSELs arranged to project light pulses onto the tissue from a distance inside the body, VCSELs arranged to project light pulses onto the tissue from a distance outside the body, and VCSELs arranged to transmit light pulses to the tissue being stimulated via an optical fiber (from either inside or outside the body).

In various embodiments, the present invention provides VCSELs for indirect stimulation of tissue, VCSELs with an emission wavelength between 250-4000 nm, VCSELs with an emission wavelength between 250-480 nm (e.g., GaN-based devices), VCSELs with an emission wavelength between 620-700 nm (e.g., GaAs-based optical devices), VCSELs with an emission wavelength between 780-1000 nm (e.g., AlGaAs-based devices), VCSELs with an emission wavelength between 1300-1600 nm (e.g., InGaAsP devices), VCSELs with an emission wavelength between 1800-2200 nm (e.g., InGaAsP-based or Antimonide-based devices), one-dimensional or two dimensional VCSEL arrays, VCSEL arrays integrated with lens arrays or fiber lens, VCSEL arrays integrated with electronics, VCSELs arranged immediately adjacent to the tissue being stimulated, VCSELs arranged to project light pulses onto the tissue from a distance inside the body, VCSELs arranged to project light pulses onto the tissue from a distance outside the body, and VCSELs arranged to transmit light pulses to the tissue being stimulated via an optical fiber (from either inside or outside the body).

In some embodiments, the present invention provides an apparatus that includes a VCSEL array integrated with electronics, and configured to provide light signals (infrared, visible, or ultraviolet) to stimulate a response in animal tissue. Some embodiments further include:

Electronics that include drivers for each individual VCSEL.

Electronics that include drivers plus a feedback loop from biological tissue (potentially the tissue being stimulated or some other part of the body).

In some embodiments, electronics that include drivers plus a signal processor to provide input to each channel (VCSEL) are provided. For example, the sound processor in a Cochlear implant, or the gyro, magnetic compass, and/or gravity orientation for a vestibular implant. In some embodiments, the signal processor also generates one or more therapeutic signals to maintain nerve integrity during healing.

In some embodiments, the present invention provides a method for stimulating human tissue that includes applying a series of pulsed laser energy from a VCSEL to animal tissue.

In some embodiments, the present invention provides a method that includes receiving audio information; and outputting a series of laser pulses from an array of a plurality of VCSELs to the cochlea of an animal, the pulses based on the audio information and configured to simulate hearing responses.

In some embodiments, the method further includes outputting the laser beam as a series of pulses wherein the laser beam has a pulse-repetition rate (PRR) of between about 0.01 kHz and about 500 kHz.

In some embodiments, the method further includes, outputting the laser beam as a series of pulses wherein the laser beam has a pulse-repetition rate (PRR), wherein the PRR is about 10-20 Hz, about 20-50 Hz, about 50-100 Hz, about 100-200 Hz, about 200-500 Hz, about 500-1000 Hz, about 1-2 kHz, about 2-5 kHz, about 5-10 kHz, about 10-20 kHz, about 20-50 kHz, about 50-100 kHz, about 100-200 kHz, about 200-500 kHz, about 500-1000 kHz, or greater than 1 MHz.

In some embodiments, the method further includes, outputting the laser beam pulses such that each pulse has a non-zero pulse energy of up to 100 µJ.

In some embodiments, the method further includes, outputting the laser beam pulses such that each pulse has a non-zero pulse energy, wherein per-pulse energies are about 0.1-0.2 µJ, about 0.2-0.5 µJ, about 0.5-1 µJ, about 1-2 µJ, about 2-5 µJ, about 5-10 µJ, about 10-20 µJ, about 20-50 µJ, about 50-100 µJ, about 100-200 µJ, about 200-500 µJ, or about 500-1000 µJ.

In some embodiments, the method further includes, outputting the laser beam pulses such that each pulse has a non-zero pulse width of about 100 ns or less.

In some embodiments, the method further includes, outputting the laser beam pulses such that each pulse has a non-zero pulse width, wherein the laser outputs pulse lengths of about 0.1-0.2 ns, about 0.2-0.5 ns, about 0.5-1 ns, about 1-2 ns, about 2-3 ns, about 3-4 ns, about 4-6 ns, about 6-8 ns, about 8-10 ns, about 10-20 ns, about 20-30 ns, about 30-40 ns, about 40-60 ns, about 60-80 ns, about 80-100 ns, about 100-200 ns, about 200-300 ns, about 300-400 ns, about 400-600 ns, about 600-800 ns, or about 800-1000 ns.

In some embodiments, the present invention provides a method that includes emitting pulsed light having a wavelength in a range of 1.8 microns to 2 microns and having a pulse duration from each of a plurality of vertical cavity surface-emitting lasers (VCSELs) including a first VCSEL and a second VCSEL; directing the light from the first VCSEL onto a first tissue to stimulate the first tissue but substantially not onto a second tissue; and directing the light from the second VCSEL onto the second tissue to stimulate the second tissue but substantially not onto the first tissue.

In some embodiments, the method further includes emitting pulsed light having a wavelength in a range of 650 nm to 850 nm and having a pulse duration from each of a plurality of vertical cavity surface-emitting lasers (VCSELs) including a third VCSEL and a fourth VCSEL; directing the light from the third VCSEL onto the first tissue and illuminating the first tissue but substantially not illuminating the second tissue, detecting a reflected light from the first tissue and determining a first physiological activity of the first tissue; directing the light from the fourth VCSEL onto the second tissue and illuminating the second tissue but substantially not illuminating the first tissue; and detecting a reflected light from the second tissue and determining a second physiological activity of the second tissue.

In some embodiments of the method the first VCSEL and the second VCSEL are located on a single semiconductor substrate.

In some embodiments of the method the third VCSEL and the fourth VCSEL are located on a single semiconductor substrate.

In some embodiments of the method the first VCSEL, the second VCSEL, the third VCSEL and the fourth VCSEL are located on a single semiconductor substrate.

In some embodiments, the method further includes integrating a first microlens with the first VCSEL and focusing the pulsed light from the first VCSEL onto the first tissue; integrating a second microlens with the second VCSEL and focusing the pulsed light from the second VCSEL onto the second tissue; integrating a third microlens with the third VCSEL and focusing the pulsed light from the third VCSEL onto the first tissue; and integrating a fourth microlens with the fourth VCSEL and focusing the pulsed light from the fourth VCSEL onto the second tissue.

In some embodiments, the method further includes providing a fiber optic bundle including a plurality of optical fibers; integrating a first optical fiber with the first VCSEL and directing the pulsed light from the first VCSEL onto the first tissue; integrating a second optical fiber with the second VCSEL and directing the pulsed light from the second VCSEL onto the second tissue; integrating a third optical fiber with the third VCSEL and directing the pulsed light from the third VCSEL onto the first tissue; and integrating a fourth optical fiber with the fourth VCSEL and directing the pulsed light from the fourth VCSEL onto the second tissue.

In some embodiments of the method each optical fiber in the plurality of optical fibers includes a lens.

In some embodiments of the method the first VCSEL and the third VCSEL are integrated into a first flex-cuff ring and the second VCSEL and the third VCSEL are integrated into a second flex-cuff ring.

In some embodiments of the method the first VCSEL, the second VCSEL, the third VCSEL and the fourth VCSEL are mounted in a biocompatible housing having an optical feed through.

In some embodiments, the present invention provides an apparatus that includes a plurality of vertical cavity surface-emitting lasers (VCSELs) including a first VCSEL and a second VCSEL; a control circuit configured to control generation of pulsed light from the first and second VCSELs; a light delivery system configured to direct the light from the first VCSEL onto a first tissue but substantially not onto a second tissue in order to stimulate the first tissue; and the light delivery system further configured to direct the light from the second VCSEL onto the second tissue but substantially not onto the first tissue in order to stimulate the second tissue.

In some embodiments, the apparatus further includes a plurality of vertical cavity surface-emitting lasers (VCSELs) including a third VCSEL and a fourth VCSEL; the control circuit further configured to control generation of pulsed light from the third and fourth VCSELs; the light delivery system further configured to direct the light from the third VCSEL onto a first tissue but substantially not onto a second tissue in order to illuminate the first tissue; the light delivery system further configured to direct the light from the fourth VCSEL onto the second tissue but substantially not onto the first tissue in order to illuminate the second tissue; a plurality of detectors including a first detector and a second detector; the first detector configured to detect reflected light from the first tissue to determine a first physiological activity in the first tissue; and the second detector configured to detect reflected light from the second tissue to determine a second physiological activity in the second tissue.

In some embodiments of the apparatus the first VCSEL and the second VCSEL are provided on a single semiconductor substrate.

In some embodiments of the apparatus the third VCSEL and the fourth VCSEL are provided on a single semiconductor substrate.

In some embodiments of the apparatus the first VCSEL, the second VCSEL, the third VCSEL and the fourth VCSEL are provided on a single semiconductor substrate.

In some embodiments, the apparatus further includes a first microlens integrated with the first VCSEL to focus the pulsed light from the first VCSEL onto the first tissue; a second microlens integrated with the second VCSEL to focus the pulsed light from the second VCSEL onto the second tissue; a third microlens integrated with the third VCSEL to focus the pulsed light from the third VCSEL onto the first tissue; and a fourth microlens integrated with the fourth VCSEL to focus the pulsed light from the fourth VCSEL onto the second tissue.

In some embodiments, the apparatus further includes a fiber optic bundle including a plurality of optical fibers, each optical fiber having a first end and a second end; a first optical fiber operably coupled at the first end of the first optical fiber to the first VCSEL to direct the pulsed light from the first VCSEL through the first optical fiber and the second end of the first optical fiber onto the first tissue; a second optical fiber operably coupled at the first end of the second optical fiber to the second VCSEL to direct the pulsed light from the second VCSEL through the second optical fiber and the second end of the second optical fiber onto the second tissue; a third optical fiber operably coupled at the first end of the third optical fiber to the third VCSEL to direct the pulsed light from the third VCSEL through the third optical fiber and the second end of the third optical fiber onto the first tissue; and a fourth optical fiber operably coupled at the first end of the fourth optical fiber to the fourth VCSEL to direct the pulsed light from the fourth VCSEL through the fourth optical fiber and the second end of the fourth optical fiber onto the second tissue.

In some embodiments of the apparatus each optical fiber in the plurality of optical fibers includes a lens.

In some embodiments of the apparatus the first VCSEL and the third VCSEL are integrated into a first flex-cuff ring and the second VCSEL and the third VCSEL are integrated into a second flex-cuff ring.

In some embodiments of the apparatus the first VCSEL, the second VCSEL, the third VCSEL and the fourth VCSEL are mounted in a biocompatible housing having an optical feed through.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method comprising:
    emitting pulsed light having a wavelength in a range of 1.8 microns to 2 microns and having a pulse duration from each of a first plurality of vertical cavity surface-emitting lasers (VCSELs) including a first VCSEL and a second VCSEL, wherein the pulsed light from the first VCSEL and the second VCSEL is configured to stimulate nerve-action-potential responses in optically stimulatable target tissue, and wherein at least the first VCSEL is mounted on a first flexible substrate portion configured to conform to an anatomical shape of a first optically stimulatable target tissue of an animal;
    directing the light from the first VCSEL onto the first tissue but substantially not onto a second optically stimulatable target tissue in order to stimulate nerve-action-potential responses in the first tissue; and
    directing the light from the second VCSEL onto the second tissue but substantially not onto the first tissue in order to stimulate nerve-action-potential responses in the second tissue.

2. The method of claim 1, further comprising:
    emitting light having a wavelength in a range of 650 nm to 850 nm from each of a second plurality of vertical cavity surface-emitting lasers (VCSELs) including a third VCSEL and a fourth VCSEL, wherein the first VCSEL and the third VCSEL are mounted on the first flexible substrate portion;
    directing the light from the third VCSEL onto the first tissue and illuminating the first tissue but substantially not illuminating the second tissue;
    detecting a reflected light from the first tissue and determining a first physiological activity of the first tissue;
    directing the light from the fourth VCSEL onto the second tissue and illuminating the second tissue but substantially not illuminating the first tissue; and
    detecting a reflected light from the second tissue and determining a second physiological activity of the second tissue.

3. The method of claim 1, wherein the first VCSEL and the second VCSEL are formed in a monolithic single semiconductor substrate.

4. The method of claim 2, wherein the third VCSEL and the fourth VCSEL are formed in a monolithic single semiconductor substrate.

5. The method of claim 2, wherein the second VCSEL and the fourth VCSEL are mounted on a second flexible substrate portion configured to conform to an anatomical shape of the second optically stimulatable target tissue, wherein the first flexible substrate portion and the second flexible substrate portion are both part of a single flex-circuit array, the method further comprising:
    internally inserting the single flex-circuit array into a cochlea having a cochlear nerve, wherein the first tissue is located in a first region of the cochlear nerve and the second tissue is located in a second region of the cochlear nerve.

6. The method of claim 2, further comprising:
    integrating a first microlens with the first VCSEL and focusing the pulsed light from the first VCSEL onto the first tissue;
    integrating a second microlens with the second VCSEL and focusing the pulsed light from the second VCSEL onto the second tissue;
    integrating a third microlens with the third VCSEL and focusing the pulsed light from the third VCSEL onto the first tissue; and
    integrating a fourth microlens with the fourth VCSEL and focusing the pulsed light from the fourth VCSEL onto the second tissue.

7. The method of claim 2, wherein the second VCSEL and the fourth VCSEL are mounted on a second flexible substrate portion configured to conform to an anatomical shape of the second optically stimulatable target tissue, wherein the first flexible substrate portion is a first flex-cuff ring and the second flexible substrate portion is a second flex-cuff ring.

8. The method of claim 2, wherein the first VCSEL, the second VCSEL, the third VCSEL and the fourth VCSEL are mounted in one or more biocompatible housings having an optical feed through.

9. An apparatus comprising:
a first plurality of vertical cavity surface-emitting lasers (VCSELs) including a first VCSEL and a second VCSEL;
a control circuit configured to control generation of pulsed light from the first and second VCSELs, wherein the pulsed light from the first VCSEL and the second VCSEL is configured to stimulate nerve-action-potential responses in optically stimulatable target tissue, and wherein at least the first VCSEL is mounted on a first flexible substrate portion configured to conform to an anatomical shape of a first optically stimulatable target tissue of an animal;
a light delivery system configured to direct the light from the first VCSEL onto the first tissue but substantially not onto a second optically stimulatable target tissue in order to stimulate nerve-action-potential responses in the first tissue; and
the light delivery system further configured to direct the light from the second VCSEL onto the second tissue but substantially not onto the first tissue in order to stimulate nerve-action-potential responses in the second tissue.

10. The apparatus of claim 9, further comprising:
a second plurality of vertical cavity surface-emitting lasers (VCSELs) including a third VCSEL and a fourth VCSEL, wherein the first VCSEL and the third VCSEL are located on the first flexible substrate portion;
the light delivery system further configured to direct the light from the third VCSEL onto the first tissue but substantially not onto the second tissue in order to illuminate the first tissue;
the light delivery system further configured to direct the light from the fourth VCSEL onto the second tissue but substantially not onto the first tissue in order to illuminate the second tissue;
a plurality of detectors including a first detector and a second detector;
the first detector configured to detect reflected light from the first tissue to determine a first physiological activity in the first tissue; and
the second detector configured to detect reflected light from the second tissue to determine a second physiological activity in the second tissue.

11. The apparatus of claim 9, wherein the first VCSEL and the second VCSEL are formed in a monolithic single semiconductor substrate.

12. The apparatus of claim 10, wherein the third VCSEL and the fourth VCSEL are formed in a monolithic single semiconductor substrate.

13. The apparatus of claim 10, wherein the second VCSEL and the fourth VCSEL are mounted on a second flexible substrate portion configured to conform to an anatomical shape of the second optically stimulatable target tissue, wherein the first flexible substrate portion and the second flexible substrate portion are both part of a single flex-circuit array, wherein the single flex-circuit array is configured to be inserted internally into a cochlea having a cochlear nerve, and wherein the first tissue is located in a first region of the cochlear nerve and the second tissue is located in a second region of the cochlear nerve.

14. The apparatus of claim 10, further comprising:
a first microlens integrated with the first VCSEL to focus the pulsed light from the first VCSEL onto the first tissue;
a second microlens integrated with the second VCSEL to focus the pulsed light from the second VCSEL onto the second tissue;
a third microlens integrated with the third VCSEL to focus the pulsed light from the third VCSEL onto the first tissue; and
a fourth microlens integrated with the fourth VCSEL to focus the pulsed light from the fourth VCSEL onto the second tissue.

15. The apparatus of claim 10, wherein the second VCSEL and the fourth VCSEL are mounted on a second flexible substrate portion configured to conform to an anatomical shape of the second optically stimulatable target tissue, wherein the first flexible substrate portion is a first flex-cuff ring and the second flexible substrate portion is a second flex-cuff ring.

16. The apparatus of claim 10, wherein the first VCSEL, the second VCSEL, the third VCSEL and the fourth VCSEL are mounted in one or more biocompatible housings having an optical feed through.

17. The apparatus of claim 10, wherein the second VCSEL and the fourth VCSEL are mounted on a second flexible substrate portion configured to conform to an anatomical shape of the second optically stimulatable target tissue.

18. The apparatus of claim 10, wherein the first VCSEL, the second VCSEL, the third VCSEL, and the fourth VCSEL are enclosed in biocompatible material having an optical feed through.

19. The method of claim 2, wherein the second VCSEL and the fourth VCSEL are mounted on a second flexible substrate portion configured to conform to an anatomical shape of the second optically stimulatable target tissue.

20. An apparatus comprising:
a plurality of vertical cavity surface-emitting lasers (VCSELs) including a first VCSEL and a second VCSEL;
means for controlling generation of pulsed light from the first and second VCSELs, wherein the pulsed light from the first and second VCSELs is configured to stimulate nerve-action-potential responses in optically stimulatable target tissue;
flexible means for conforming the plurality of VCSELs to an anatomical shape of a first optically stimulatable target tissue;
means for directing the light from the first VCSEL onto the first tissue but substantially not onto a second optically stimulatable target tissue in order to stimulate nerve-action-potential responses in the first tissue; and
means for directing the light from the second VCSEL onto the second tissue but substantially not onto the first tissue in order to stimulate nerve-action-potential responses in the second tissue.

* * * * *